United States Patent
Arnold et al.

(10) Patent No.: US 12,054,491 B2
(45) Date of Patent: Aug. 6, 2024

(54) SUBSTITUTED BENZO[F]IMIDAZO[1,5-A][1,4]DIAZEPINES AS GABA(A) RECEPTOR MODULATORS

(71) Applicants: UWM Research Foundation, Inc., Milwaukee, WI (US); The Trustees of Columbia University in the City of New York, New York, NY (US)

(72) Inventors: Alexander E. Arnold, Milwaukee, WI (US); Douglas C. Stafford, Stoughton, WI (US); James M. Cook, Milwaukee, WI (US); Charles W. Emala, Woodcliff Lake, NJ (US); Gloria Forkuo, Milwaukee, WI (US); Rajwana Jahan, Milwaukee, WI (US); Revathi Kodali, Milwaukee, WI (US); Guanguan Li, Milwaukee, WI (US); Michael Rajesh Stephen, Milwaukee, WI (US)

(73) Assignees: UWM Research Foundation, Inc., Milwaukee, WI (US); The Trustees of Columbia University in the City of New York, New York, NY (US)

( * ) Notice: Subject to any disclaimer, the term of this patent is extended or adjusted under 35 U.S.C. 154(b) by 168 days.

(21) Appl. No.: 17/886,403

(22) Filed: Aug. 11, 2022

(65) Prior Publication Data
US 2023/0103216 A1  Mar. 30, 2023

Related U.S. Application Data

(60) Division of application No. 16/325,080, filed on Feb. 12, 2019, now Pat. No. 11,447,495, and a continuation of application No. PCT/US2017/047185, filed on Aug. 16, 2017.

(60) Provisional application No. 62/375,694, filed on Aug. 16, 2016, provisional application No. 62/427,771, filed on Nov. 29, 2016.

(51) Int. Cl.
C07D 487/04 (2006.01)
A61P 11/06 (2006.01)
C07D 487/14 (2006.01)

(52) U.S. Cl.
CPC ............ *C07D 487/14* (2013.01); *A61P 11/06* (2018.01); *C07D 487/04* (2013.01)

(58) Field of Classification Search
CPC .................................................. C07D 487/04
USPC ......................................................... 540/579
See application file for complete search history.

(56) References Cited

U.S. PATENT DOCUMENTS

| | | | |
|---|---|---|---|
| 4,125,726 A | 11/1978 | Walser et al. | |
| 4,226,768 A | 10/1980 | Walser | |
| 4,238,610 A | 12/1980 | Field et al. | |
| 4,401,597 A | 8/1983 | Walser et al. | |
| 5,317,018 A | 5/1994 | Walser et al. | |
| 5,693,795 A | 12/1997 | Bender et al. | |
| 6,262,260 B1 | 7/2001 | Dhaon | |
| 8,835,424 B2 | 9/2014 | Cook et al. | |
| 2006/0003995 A1 | 1/2006 | Cook et al. | |
| 2006/0258643 A1 | 11/2006 | Cook et al. | |
| 2010/0261711 A1 | 10/2010 | Cook et al. | |
| 2010/0317619 A1 | 12/2010 | Cook et al. | |
| 2011/0275799 A1 | 11/2011 | Castellin et al. | |
| 2012/0295892 A1 | 11/2012 | Cook et al. | |
| 2015/0011618 A1 | 1/2015 | Ding et al. | |
| 2015/0258128 A1 | 9/2015 | Cook et al. | |

FOREIGN PATENT DOCUMENTS

| | | |
|---|---|---|
| CN | 103319486 A | 9/2013 |
| DE | 2540522 A1 | 4/1976 |
| EP | 135770 A2 | 4/1985 |
| WO | 199615129 A1 | 5/1996 |
| WO | 2000069836 A1 | 11/2000 |
| WO | 2001000625 A1 | 1/2001 |
| WO | 2001002402 A1 | 1/2001 |
| WO | 2003082832 A2 | 10/2003 |
| WO | 2005123686 A1 | 12/2005 |

(Continued)

OTHER PUBLICATIONS

Chemical Abstract Registry No. 1413433-15-4, indexed in the Registry File on STN CAS Online.

(Continued)

*Primary Examiner* — Douglas M Willis
(74) *Attorney, Agent, or Firm* — Michael Best & Friedrich LLP

(57) ABSTRACT

The present invention describes substituted benzo[f]imidazo[1,5-a][1,4]diazepines of the formula (I):

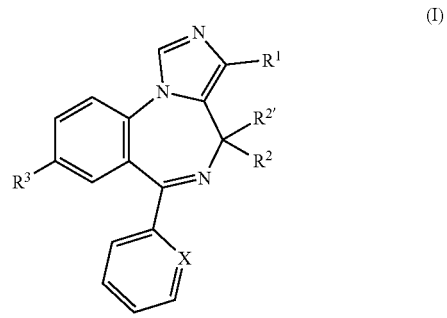

wherein $R^1$, $R^2$, $R^{2'}$, $R^3$, and X are as disclosed herein. These compounds target alpha-4 and alpha-5 GABAa receptors and are useful for the treatment of airway hyperresponsiveness and inflammation in asthma.

12 Claims, 14 Drawing Sheets

(56) References Cited

FOREIGN PATENT DOCUMENTS

| WO | 2009046004 A1 | 4/2009 |
|---|---|---|
| WO | 2012162254 A1 | 11/2012 |
| WO | 2013068554 A1 | 5/2013 |
| WO | 2014047413 A1 | 3/2014 |
| WO | 2017161370 A1 | 9/2017 |

OTHER PUBLICATIONS

Chemical Abstract Registry No. 1413433-11-0, indexed in the Registry File on STN CAS Online.
Chemical Abstract Registry No. 1318262-32-6, indexed in the Registry File on STN CAS Online.
Chemical Abstract Registry No. 1309157-83-2, indexed in the Registry File on STN CAS Online.
Chemical Abstract Registry No. 122384-71-8, indexed in the Registry File on STN CAS Online.
Chemical Abstract Registry No. 1140968-15-5, indexed in the Registry File on STN CAS Online.
Chemical Abstract Registry No. 1140967-94-7, indexed in the Registry File on STN CAS Online.
Canadian Patent Office Action for Application No. 3,033,964, dated Sep. 22, 2023 (5 pages).
Nelson, H. S., et al. (2001) Comparison of inhaled salmeterol and oral zafirlukast in asthmatic patients using concomitant inhaled corticosteroids, MedGenMed 3, 3.
Nozaki, Masakatsu et al., Medicinal Chemistry, Kagaku-Dojin Publishing Company, INC, 1995, 1st edition, pp. 98-99.
Olsen, R. W., et al. (2008) International Union of Pharmacology. LXX. Subtypes of gamma-aminobutyric acid(A) receptors: classification on the basis of subunit composition, pharmacology, and function. Update, Pharmacol Rev 60, 243-260.
Pascual, R. M., et al. (2005) Airway remodeling contributes to the progressive loss of lung function in asthma: an overview, J Allergy Clin Immunol 116, 477-486; quiz 487.
Poe, et al., "Synthesis and Characterization of a Novel γ-Aminobutyric Acid Type A (GABAA) Receptor Ligand that Combines Outstanding Metabolic Stability, Pharmacokinetics, and Anxiolytic Efficacy", J. Med. Chem., 59, (2016).
Richetto et al., "Behavioral Effects of the Benzodiazepine-Positive Modulator SH-053-2'F-S-CH3 in an Immune-Mediated Neurodevelopmental Disruption Model," Int. J. of Neuropsychopharmacology, 1-11 (2015).
Roffel, A. F., et al. (1990) Muscarinic M3 receptors mediate contraction of human central and peripheral airway smooth muscle, Pulm Pharmacol 3, 47-51.
Shen, Y., et al. (2011) Plasticity of GABAA receptors after ethanol pre-exposure in cultured hippocampal neurons, Mol Pharmacol 79, 432-442.
Sholter, D. E., et al. (2000) Adverse effects of corticosteroids on the cardiovascular system, Can J Cardiol 16, 505-511.
Shuto, Satoshi, Theory of Organic Medical Molecule, 2012, pp. 201-218.
Stamenic, T. T., et al. (2016) Ester to amide substitution improves selectivity, efficacy and kinetic behavior of a benzodiazepine positive modulator of GABAA receptors containing the alpha5 subunit, Eur J Pharmacol 791, 433-443.
Tian, J., et al. (2004) Gamma-aminobutyric acid inhibits T cell autoimmunity and the development of inflammatory responses in a mouse type 1 diabetes model, J Immunol 173, 5298-5304.
Trends in Asthma Morbidity and Mortality, American Lung Association Epidemiology & Statistics Unit Research and Program Services.
Tyagi, N., et al. (2007) Differential expression of gamma-aminobutyric acid receptor A (GABA(A)) and effects of homocysteine, Clin Chem Lab Med 45, 1777-1784.
Van Rijt, L. S., et al. (2004) A rapid flow cytometric method for determining the cellular composition of bronchoalveolar lavage fluid cells in mouse models of asthma, J Immunol Methods 288, 111-121.
Vinkers, et al., "GABAA Receptor a Subunits Differentially Contribute to Diazepam Tolerance after Chronic Treatment," Plos One, 7 (8) e43054, 1-11 (2012).
Walser et al., Quinazolines and 1, 4 Benzodiazepines. XCV [1]. Synthesis of 1, 4 Benzodiazepines by Ring Expansion of 2-Chloromethylquinazolines with Carbanions, J. Heterocyclic Chem., 1986, 23(4):1303-1314.
Watjen et al., "Novel Benzodiazepine Receptor Partial Agonists: Oxadiazolylimidazobenzodiazepines", J. Med. Chem., 1989, 32(10):2282-2291.
Xiang et al. (2007) A GABAergic system in airway epithelium is essential for mucus overproduction in asthma, Nat Med 13, 862-867.
Yang et al., An improved process for the synthesis of 4H-imidazo[1,5a][1,4]benzodiazepines. Synthesis 2009, 40.
Yocum, G. T., et al. (2016) Targeting the gamma-Aminobutyric Acid A Receptor alpha4 Subunit in Airway Smooth Muscle to Alleviate Bronchoconstriction, Am J Respir Cell Mol Biol 54, 546-553.
Zhang, L., et al. (2014) Inhaled corticosteroids in children with persistent asthma: effects on growth, Cochrane Database Syst Rev, CD009471.
Chemical Abstract Registry No. 98602-21-2, indexed in the Registry File on STN CAS Online.
Chemical Abstract Registry No. 98602-18-7, indexed in the Registry File on STN CAS Online.
Chemical Abstract Registry No. 98601-98-0, indexed in the Registry File on STN CAS Online.
Chemical Abstract Registry No. 98602-01-8, indexed in the Registry File on STN CAS Online.
Chemical Abstract Registry No. 98601-62-8, indexed in the Registry File on STN CAS Online.
Chemical Abstract Registry No. 98601-59-3, indexed in the Registry File on STN CAS Online.
Chemical Abstract Registry No. 98601-57-1, indexed in the Registry File on STN CAS Online.
Chemical Abstract Registry No. 98601-56-0, indexed in the Registry File on STN CAS Online.
Chemical Abstract Registry No. 98601-55-9, indexed in the Registry File on STN CAS Online.
Chemical Abstract Registry No. 98601-53-7, indexed in the Registry File on STN CAS Online.
Chemical Abstract Registry No. 88437-87-0, indexed in the Registry File on STN CAS Online.
Chemical Abstract Registry No. 68288-21-1, indexed in the Registry File on STN CAS Online.
Chemical Abstract Registry No. 612527-33-0, indexed in the Registry File on STN CAS Online.
Chemical Abstract Registry No. 612526-65-5, indexed in the Registry File on STN CAS Online.
Chemical Abstract Registry No. 59469-56-6, indexed in the Registry File on STN CAS Online.
Chemical Abstract Registry No. 59469-51-1, indexed in the Registry File on STN CAS Online.
Chemical Abstract Registry No. 59469-44-2, indexed in the Registry File on STN CAS Online.
Chemical Abstract Registry No. 59469-24-8, indexed in the Registry File on STN CAS Online.
Chemical Abstract Registry No. 59468-53-0, indexed in the Registry File on STN CAS Online.
Chemical Abstract Registry No. 59468-46-1, indexed in the Registry File on STN CAS Online.
Chemical Abstract Registry No. 59468-45-0, indexed in the Registry File on STN CAS Online.
Chemical Abstract Registry No. 59468-44-9, indexed in the Registry File on STN CAS Online.
Chemical Abstract Registry No. 2095608-41-4, indexed in the Registry File on STN CAS Online.
Chemical Abstract Registry No. 186351-12-2, indexed in the Registry File on STN CAS Online.
Chemical Abstract Registry No. 153874-00-1, indexed in the Registry File on STN CAS Online.

(56) References Cited

OTHER PUBLICATIONS

Chemical Abstract Registry No. 149873-81-4, indexed in the Registry File on STN CAS Online.
Chemical Abstract Registry No. 149873-69-8, indexed in the Registry File on STN CAS Online.
Chemical Abstract Registry No. 1481640-99-6, indexed in the Registry File on STN CAS Online.
Al, J., et al. (2001) Honokiol and magnolol selectively interact with GABAA receptor subtypes in vitro, Pharmacology 63, 34-41.
Akinci, M. K., et al. (1999) Widespread expression of GABA(A) receptor subunits in peripheral tissues, Neuroscience Research 35, 145-153.
Anzini et al., "New Insight into the Central Benzodiazepine Receptor-Ligand Interactions: Design, Synthesis, Biological Evaluation, and Molecular Modeling of 3-Substituted 6-Phenyl-4H-imidazo[1,5-a][1,4]benzodiazepines and Related Compounds", Acs J. Med. Chem., 2011, vol. 54, pp. 5694-5711.
Australian Patent Office Examination Report for Application No. 2017313753 dated Jan. 19, 2021 (9 pages).
Bhat, R., et al. (2010) Inhibitory role for GABA in autoimmune inflammation, Proc Natl Acad Sci U S A 107, 2580-2585.
Bjurstom, H., et al. (2008) GABA, a natural immunomodulator of T lymphocytes, J Neuroimmunol 205, 44-50.
Cates, C. J., et al. (2008) Regular treatment with salmeterol for chronic asthma: serious adverse events, Cochrane Database Syst Rev, CD006363.
Cates, C. J., et al. (2012) Regular treatment with formoterol for chronic asthma: serious adverse events, Cochrane Database Syst Rev, CD006923.
Chauhan, B. F., et al. (2014) Addition to inhaled corticosteroids of long-acting beta2-agonists versus anti-eukotrienes for chronic asthma, Cochrane Database Syst Rev, CD003137.
Chinese Patent Office Action for Application No. 201780063337.9 dated May 17, 2021, (15 pages, statement of relevance included).
Ciriaco, M., et al. (2013) Corticosteroid-related central nervous system side effects, J Pharmacol Pharmacother 4, S94-98.
Clayton, T., et al. (2015) A Review of the Updated Pharmacophore for the Alpha 5 GABA(A) Benzodiazepine Receptor Model, Int J Med Chem 2015, 430248.
Cohn, R. C. (2003) A review of the effects of medication delivery systems on treatment adherence in children with asthma, Current Ther Res Clin Exp 64, 34-44.
Co-Pending U.S. Appl. No. 16/086,053, filed Sep. 18, 2018 by Cook et al.
Dahl, R. Systemic side effects of inhaled corticosteroids in patients with asthma. Respir Med 2006, 100, (8), 1307-17.
Del Pozo et al., "Reactions of 1,4 Benzodiazepinic N-Nitrosoamidines with Tosylmethyl Isocyanide: A Novel Synthesis of Midazolam", Synthesis, 2004, 2004(16):2697-2703.
Dionisio, L., et al. (2011) An intrinsic GABAergic system in human lymphocytes, Neuropharmacology 60, 513-519.
Everard, M. L. (2000) Aerosol therapy past, present, and future: a clinician's perspective, Respir Care 45, 769-776.
Fabbri, L. M., et al. (1996) Oral vs inhaled asthma therapy. Pros, cons and combinations, Drugs 52 Suppl 6, 20-28.
Forkuo et al., "Alleviation of Multiple Asthmatic Pathologic Features with Orally Available and Subtype Selective GABA(A) Receptor Modulators", Molecular Pharmaceutics, 2017, vol. 14, pp. 2088-2098.
Forkuo, G. S., et al. (2016) Development of GABAA Receptor Subtype-Selective Imidazobenzodiazepines as Novel Asthma Treatments, Mol Pharm 13, 2026-2038.
Forkuo, G. S., et al. (2016) PDE4 Inhibitors Attenuate the Asthma Phenotype Produced by beta2-adrenoceptor Agonists in PNMT-KO Mice, Am J Respir Cell Mol Biol.
Gallos, G., et al. (2012) Targeting the restricted alpha-subunit repertoire of airway smooth muscle GABAA receptors augments airway smooth muscle relaxation, Am J Physiol Lung Cell Mol Physiol 302, L248-256.
Gallos, G., et al. (2015) Selective targeting of the alpha5-subunit of GABAA receptors relaxes airway smooth muscle and inhibits cellular calcium handling, Am J Physiol Lung Cell Mol Physiol 308, L931-942.
Garcia-Recio, S., et al. (2015) Biological and Pharmacological Aspects of the NK1-Receptor, Biomed Res Int 2015, 495704.
Gilman et al., "Astropisomers of 1,4-Benzodiazepines. 2. Synthesis and Resolution of Imidazo[1,5,a][1,4] Benzodiazepines", J. Org. Chem., 1993, vol. 58, pp. 3285-3298.
Glaab, T., et al. (2007) Invasive and noninvasive methods for studying pulmonary function in mice, Respir Res 8, 63.
Gosens, R., et al. (2006) Muscarinic receptor signaling in the pathophysiology of asthma and COPD, Respir Res 7, 73.
Guilbert, T. W., et al. (2006) Long-term inhaled corticosteroids in preschool children at high risk for asthma, N Engl J Med 354, 1985-1997.
Han et al., "A study of the structure-activity relationship of GABA(A)-benzodiazepine receptor bivalent ligands by conformational analysis with low temperature NMR and X-ray analysis", Bioorganic & Medicinal Chemistry, 2008, vol. 16, pp. 8853-8862.
Henderson, W. R., Jr., et al. (1996) The importance of leukotrienes in airway inflammation in a mouse model of asthma, J Exp Med 184, 1483-1494.
Indian Patent Office Examination Report for Application No. 201917005915 dated Nov. 23, 2020 (8 pages).
International Preliminary Report on Patentability for Application No. PCT/US2017/047185 dated Feb. 28, 2019 (13 pages).
International Search Report and Written Opinion for Application No. PCT/US2017/047185 dated Dec. 11, 2017 (8 pages).
Jahan, R., et al. (2016) Optimization of Substituted Imidazobenzodiazepines as Novel Asthma Treatments, Eur J Med Chem 126, 550-560.
Japanese Patent Office Action for Application No. 2019-508255 dated Apr. 8, 2021 (18 pages, English translation Included).
Katsifis et al., "Synthesis of Iodine-123 Labelled Analogues of Imidazenil and Ethyl-Imidazenil for Studying Benzodiazepine Receptors Using SPECT", Jounral of Labelled Compounds and Radiopharmaceuticals, 1996, vol. XXXVIII, No. 12, 12 pages.
Kelly, H. W., et al. (2012) Effect of inhaled glucocorticoids in childhood on adult height, N Engl J Med 367, 904-912.
Lee, J. J., et al. (1997) Interleukin-5 expression in the lung epithelium of transgenic mice leads to pulmonary changes pathognomonic of asthma, J Exp Med 185, 2143-2156.
Li, et al., "Development of Selective Ligands for Benzodiazepine Receptor Subtypes by Manipulating the Substituents at Positions –3 and –7 of Optically Active BzR Ligands," Medicinal Chemistry Research, 13, 259-281 (2004).
Lima, J. J., et al. (2006) Influence of leukotriene pathway polymorphisms on response to montelukast in asthma, American Journal of Respiratory and Critical Care Medicine 173, 379-385.
Lipworth, B. J. (1999) Systemic adverse effects of inhaled corticosteroid therapy: A systematic review and meta-analysis, Arch Intern Med 159, 941-955.
Marta et al., "Benzodiazepine-Induced Hyperphagia: Development and Assessment of a 3D Pharmacophore By Computational Methods," Journal of Biomolecular Structure & Dynamics, 2000, 17(5):769-778.
Mizuta, K., et al. (2008) GABAA receptors are expressed and facilitate relaxation in airway smooth muscle, Am J Physiol Lung Cell Mol Physiol 294, L1206-1216.
Montuschi, P., et al. (2010) Leukotriene modifiers for asthma treatment, Clinical and Experimental Allergy 40, 1732-1741.
Mortensen, M., et al. (2011) GABA Potency at GABA(A) Receptors Found in Synaptic and Extrasynaptic Zones, Front Cell Neurosci 6, 1.
Munroe, M. E., et al. (2010) Anti-inflammatory effects of the neurotransmitter agonist Honokiol in a mouse model of allergic asthma, J Immunol 185, 5586-5597.
Nagano, Tetsuo; Natsugari, Hideaki; Hara, Hiroshi; Medicinal Chemistry, Japan, Apr. 10, 2007, 1st edition, 4th impression, pp. 139-140.
Namjoshi et al., "Search for α3β2/3γ2 subtype selective ligands that are stable on human liver microsomes," Bioorg. Med. Chem. 2013, 21, 93-101.

(56) References Cited

OTHER PUBLICATIONS

National Heart, L., and Blood Institute. (Aug. 2007) Guidelines for the Diagnosis and Management of Asthma, Full Report.

SUBSTITUTED BENZO[F]IMIDAZO[1,5-A][1,4]DIAZEPINES AS GABA(A) RECEPTOR MODULATORS

RELATED APPLICATIONS

This patent application is a divisional of U.S. patent application Ser. No. 16/325,080, filed Feb. 12, 2019, which is the United States national stage entry, under 35 U.S.C. § 371, of international application number PCT/US2017/047185, filed Aug. 16, 2017, which claims the benefit of U.S. Provisional Application No. 62/375,694, filed Aug. 16, 2016, and U.S. Provisional Application No. 62/427,771, filed Nov. 29, 2016, the entire contents of which are hereby incorporated by reference.

STATEMENT REGARDING FEDERALLY SPONSORED RESEARCH OR DEVELOPMENT

This invention was made with United States government support under NIH grant numbers R01HL118561, R01MH096463, R01GM065281 and R01HL122340. The United States government has certain rights to this invention.

BACKGROUND

Bronchoconstrictive diseases are major health concerns worldwide. These include asthma, chronic obstructive pulmonary disease (COPD), and bronchopulmonary dysplasia (BPD), and despite existing treatments such as β-adrenergic agonists, inhaled corticosteroids, and inhaled anti-cholinergics, bronchoconstrictive diseases remain highly prevalent. Asthma by itself affects 300 million people worldwide. Since asthma predisposes patients to severe acute airway constriction, novel therapeutic mechanisms capable of promoting airway smooth muscle relaxation would be clinically valuable.

Thus, there continues to be demand for treatment and preventive agents effective against bronchoconstrictive diseases. New pharmacologic approaches to treat these diseases are limited. Therapeutic limitations are especially apparent in medications that promote acute airway smooth muscle relaxation, as β-adrenoceptor agonists and anti-cholinergics remain the only drug classes currently utilized to treat acute airway constriction.

The $GABA_A$ receptors ($GABA_AR$) are ligand-gated chloride ion channels well-known for their suppressive effects in the central nervous system (CNS). $GABA_ARs$ are heteropentamers assembled from 19 different subunits ($\alpha_{1-6}$, $\beta_{1-3}$, $\gamma_{1-3}$, $\delta$, $\epsilon$, $\pi$, $\theta$, $\rho_{1-3}$). Classical $GABA_ARs$ consist of two $\alpha$, two $\beta$, and one $\gamma$, $\delta$, $\epsilon$, $\theta$, or $\pi$ subunit. Compounds that alter the efficacy of function of $GABA_ARs$ have been used extensively as medicaments for disorders of the central nervous system. In addition to neurons, $GABA_AR$ subunits have been identified in airway smooth muscle, airway epithelium, and immune/inflammatory cells. Compounds that selectively react to discrete $GABA_AR$ subtypes on airway smooth muscle cells, epithelia cells and immune cells is important is a heretofore novel approach for treating bronchoconstrictive diseases. Compounds with a preference for the $\alpha_4\beta_3\gamma_2$ $GABA_AR$ or $\alpha_5\beta_3\gamma_2$ $GABA_AR$ have been identified as pharmacologically active in the described models of asthma.

SUMMARY

In one aspect, the invention provides compounds of formula (I), or a pharmaceutically acceptable salt thereof,

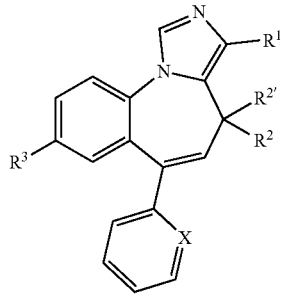

wherein:
$R^1$ is COOH, a carboxylic ester, a carboxylic acid isostere, or a carboxylic ester isostere;
X is C—H, C—F, C—Cl, C—Br, C—I, C—$CF_3$, or N;
$R^2$ and $R^{2'}$ are each independently H, D, $C_{1-4}$ alkyl, $CD_3$, F, Cl, $CF_3$, $CCl_3$, or cyclopropyl; or $R^2$ and $R^{2'}$ together form an optionally substituted ring; and
$R^3$ is H, F, Cl, Br, $CF_3$, $CHF_2$, —$OCF_3$, —$OCHF_2$, CN, OH, —$OC_{1-4}$alkyl, —C≡CH, or cyclopropyl.

Another aspect of the invention provides compounds of formula (II), or a pharmaceutically acceptable salt thereof,

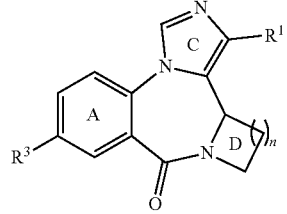

wherein:
$R^1$ is COOH, a carboxylic ester, a carboxylic acid isostere, or a carboxylic ester isostere;
n is 1 or 2; and
$R^3$ is H, F, Cl, Br, $CF_3$, $CHF_2$, —$OCF_3$, —$OCHF_2$, CN, OH, —$OC_{1-4}$alkyl, —C≡CH, or cyclopropyl.

In another aspect, the present invention provides a pharmaceutical composition including a compound of formula (I) or (II), or a pharmaceutically acceptable salt thereof, and a pharmaceutically acceptable carrier. In some embodiments, the composition may be an oral or an aerosol formulation.

In another aspect, the invention provides a method of reducing airway constriction comprising administering an effective amount of a compound or composition of formula (I) or (II), or a pharmaceutically acceptable salt thereof to a subject in need thereof. In some embodiments, compounds of formula (I) or (II) have reduced benzodiazepine-type CNS effects in a subject compared to diazepam at therapeutic doses.

In another aspect, the invention provides a method of reducing lung inflammation comprising administering an effective amount of a compound or composition of formula (I) or (II), or a pharmaceutically acceptable salt thereof to a subject in need thereof. In some embodiments, compounds of formula (I) or (II) have reduced benzodiazepine-type CNS effects in a subject compared to diazepam at therapeutic doses.

In another aspect, the invention provides a method of reducing development of disease in a subject having risk factors associated with lung inflammation comprising administering an effective amount of a compound or composition of formula (I) or (II), or a pharmaceutically acceptable salt thereof to a subject in need thereof. In some embodiments, compounds of formula (I) or (II) have reduced benzodiazepine-type CNS effects in a subject compared to diazepam at therapeutic doses.

In another aspect, the invention provides a method of treating lung disease comprising administering an effective amount of a compound or composition of formula (I) or (II), or a pharmaceutically acceptable salt thereof to a subject in need thereof. In some embodiments, compounds of formula (I) or (II) have reduced benzodiazepine-type CNS effects in a subject compared to diazepam at therapeutic doses.

In some aspects, the compounds of the present invention selectively target the $\alpha_4$ and as subunits of $GABA_AR$s. In some aspects, the compounds of the present invention are allosteric modulators of the $GABA_AR$s that are selective for the $\alpha_4$ and $\alpha_5$ benzodiazepine allosteric modulatory sites on $GABA_AR$s. In some aspects, the compounds of the present invention may have limited inability to cross the blood-brain barrier.

DETAILED DESCRIPTION

Figure 1A:
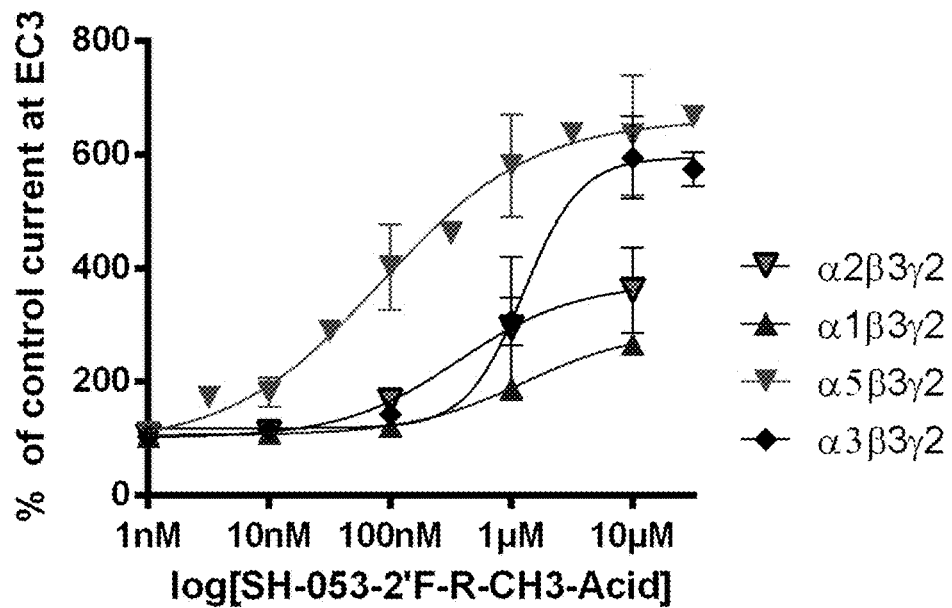
FIG. 1A shows dose dependent modulation of GABA elicited currents by SH-053-2'F—R—CH$_3$-Acid on *Xenopus* oocytes expressing $GABA_A$ receptor subtypes $\alpha1\beta3\gamma2$, $\alpha2\beta3\gamma2$, $\alpha3\beta3\gamma2$, $\alpha4\beta3\gamma2$ and $\alpha5\beta3\gamma2$.

Recent studies have shown the presence of functional gamma-amino butyric acid type A receptors ($GABA_AR$) on the surface of cell types involved in asthmatic lung pathophysiology. Importantly, $GABA_AR$ signaling can influence the contractile state of airway smooth muscle (ASM), inflammatory processes, and proliferation of airway epithelial cells (AEC). Despite the growing appreciation of $GABA_AR$ signaling acting locally in the lung, a strategy that unifies and targets $GABA_AR$ responses has not been developed or exploited therapeutically for asthma treatment. Accordingly, the inventors contemplate the identification of a novel asthma therapy by systematically probing human lung cell types to identify ligands that are suppressive for ASM and immune/inflammatory cells without stimulating AEC hypertrophy.

Activation of endogenous airway smooth muscle $GABA_A$ receptors relaxes cholinergic contraction of airway smooth muscle, and molecular analysis of airway smooth muscle reveals that the $\alpha$-subunit component of these $GABA_A$ receptors is limited to the $\alpha4$ and $\alpha5$.

The present invention provides novel compounds, which may bind to specific ionotropic (ligand-gated) ion channels expressed in immune/inflammatory cells and airway smooth muscle, and consequently relax contraction. This novel finding details a new signaling pathway and protein target for relaxing airway smooth muscle contraction and can potentially be developed into a novel therapeutic against airway constriction, lung inflammation, and inflammation associated with allergic and autoimmune diseases. Thus, among other things, the present invention provides novel compounds that provide a novel therapeutic option against airway constriction, lung inflammation, and inflammation associated with allergic and autoimmune diseases and methods of using these compounds to treat various diseases.

Definitions

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th Edition, John Wiley & Sons, Inc., New York, 2001; Larock, Comprehensive Organic Transformations, VCH Publishers, Inc., New York, 1989; Carruthers, Some Modern Methods of Organic Synthesis, 3rd Edition, Cambridge University Press, Cambridge, 1987; the entire contents of each of which are incorporated herein by reference.

The term "acyl" refers to an alkylcarbonyl, cycloalkylcarbonyl, heterocyclylcarbonyl, arylcarbonyl, or heteroarylcarbonyl substituent. In some embodiments, an acyl may be further substituted (e.g., with one or more substituents). Unless otherwise stated, an acyl is unsubstituted.

The term "alkyl" refers to a straight or branched hydrocarbon chain, containing the indicated number of carbon atoms. For example, $C_1$-$C_{12}$ alkyl indicates that the alkyl group may have from 1 to 12 (inclusive) carbon atoms, and $C_1$-$C_4$ alkyl indicates that the alkyl group may have from 1 to 4 (inclusive) carbon atoms. In some embodiments, an alkyl group may be optionally substituted. Examples of $C_{1-4}$alkyl groups include methyl, ethyl, n-propyl, isopropyl, n-butyl, sec-butyl and tert-butyl. Unless otherwise stated, an alkyl is unsubstituted.

The term "alkenyl" refers to a straight or branched hydrocarbon chain having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. In some embodiments, an alkenyl group may be optionally substituted. Unless otherwise stated, an alkenyl is unsubstituted.

The term "alkynyl" refers to a straight or branched hydrocarbon chain having one or more triple bonds. Examples of alkynyl groups include, but are not limited to, ethynyl, propargyl, and 3-hexynyl. One of the triple bond carbons may optionally be the point of attachment of the alkynyl substituent. In some embodiments, an alkynyl group may be optionally substituted. Unless otherwise stated, an alkynyl is unsubstituted.

The term "aryl" refers to an aromatic carbocyclic monocyclic, bicyclic, or tricyclic hydrocarbon ring system, wherein any ring atom capable of substitution can be substituted (e.g., with one or more substituents). Examples of aryl moieties include, but are not limited to, phenyl, naphthyl, and anthracenyl. Unless otherwise stated, an aryl is unsubstituted.

The term "arylalkyl" refers to an alkyl moiety in which an alkyl hydrogen atom is replaced with an aryl group. Arylalkyl includes groups in which more than one hydrogen atom has been replaced with an aryl group. Examples of arylalkyl groups include benzyl, 2-phenylethyl, 3-phenylpropyl, 9-fluorenyl, benzhydryl, and trityl groups.

The term "cycloalkyl" as used herein refers to a saturated cyclic, bicyclic, tricyclic or polycyclic hydrocarbon groups having 3 to 12 carbons (e.g., 3, 4, 5, 6 or 7 carbon atoms). Any ring atom can be substituted (e.g., with one or more substituents). Cycloalkyl groups can contain fused rings. Fused rings are rings that share one or more common carbon atoms. Examples of monocyclic cycloalkyl groups include, but are not limited to, cyclopropyl, cyclobutyl, cyclopentyl, and cyclohexyl. Examples of bridged cycloalkyl include adamantyl and norbornyl.

The term "halo" or "halogen" as used herein refers to any radical of fluorine, chlorine, bromine or iodine.

The term "haloalkyl" as used herein refers to an alkyl in which one or more hydrogen atoms are replaced with a halogen, and includes alkyl moieties in which all hydrogens have been replaced with halogens (e.g., perfluoroalkyl such as $CF_3$).

The term "heteroaryl" as used herein refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms independently selected from O, N, S, P and Si (e.g., carbon atoms and 1-3, 1-6, or 1-9 heteroatoms independently selected from O, N, S, P and Si if monocyclic, bicyclic, or tricyclic, respectively). Any ring atom can be substituted (e.g., with one or more substituents). Heteroaryl groups can contain fused rings, which are rings that share one or more common atoms. Examples of heteroaryl groups include, but are not limited to, radicals of pyridine, pyrimidine, pyrazine, pyridazine, pyrrole, imidazole, pyrazole, oxazole, isoxazole, furan, thiazole, isothiazole, thiophene, quinoline, isoquinoline, quinoxaline, quinazoline, cinnoline, indole, isoindole, indolizine, indazole, benzimidazole, phthalazine, pteridine, carbazole, carboline, phenanthridine, acridine, phenanthroline, phenazine, naphthyridines and purines.

The term "heterocycle" as used herein refers to a non-aromatic, saturated or partially unsaturated 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, S, Si and P (e.g., carbon atoms and 1-3, 1-6, or 1-9 heteroatoms of O, N, S, Si and P if monocyclic, bicyclic, or tricyclic, respectively). Any ring atom can be substituted (e.g., with one or more substituents). Heterocyclyl groups can contain fused rings, which are rings that share one or more common atoms. Examples of heterocyclyl groups include, but are not limited to, radicals of tetrahydrofuran, tetrahydrothiophene, tetrahydropyran, piperidine, piperazine, morpholine, pyrroline, pyrimidine, pyrrolidine, indoline, tetrahydropyridine, dihydropyran, thianthrene, pyran, benzopyran, xanthene, phenoxathiin, phenothiazine, furazan, lactones, lactams such as azetidinones and pyrrolidinones, sultams, sultones, and the like.

The term "hydroxy" refers to an —OH radical. The term "alkoxy" refers to an —O— alkyl radical. The term "aryloxy" refers to an —O-aryl radical. The term "haloalkoxy" refers to an —O-haloalkyl radical.

The term "substituent" refers to a group "substituted" on an alkyl, alkenyl, alkynyl, cycloalkyl, heterocyclyl, aryl, arylalkyl or heteroaryl group at any atom of that group. Suitable substituents include, without limitation: acyl, acylamido, acyloxy, alkoxy, alkyl, alkenyl, alkynyl, amido, amino, carboxy, cyano, ester, halo, hydroxy, imino, nitro, oxo (e.g., C=O), phosphonate, sulfinyl, sulfonyl, sulfonate, sulfonamino, sulfonamido, thioamido, thiol, thioxo (e.g., C=S), and ureido. In embodiments, substituents on a group are independently any one single, or any combination of the aforementioned substituents. In embodiments, a substituent may itself be substituted with any one of the above substituents.

The above substituents may be abbreviated herein, for example, the abbreviations Me, Et and Ph represent methyl, ethyl and phenyl, respectively. A more comprehensive list of the abbreviations used by organic chemists appears in the first issue of each volume of the Journal of Organic Chemistry; this list is typically presented in a table entitled Standard List of Abbreviations. The abbreviations contained in said list, and all abbreviations used by organic chemists of ordinary skill in the art, are hereby incorporated by reference.

For compounds, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., —CH$_2$O— optionally also recites —OCH$_2$—.

In accordance with a convention used in the art, the group:

is used in structural formulas herein to depict the bond that is the point of attachment of the moiety or substituent to the core or backbone structure.

In the context of treating a disorder, the term "effective amount" as used herein refers to an amount of the compound or a composition comprising the compound which is effective, upon single or multiple dose administrations to a subject, in treating a cell, or curing, alleviating, relieving or improving a symptom of the disorder in a subject. An effective amount of the compound or composition may vary according to the application. In the context of treating a disorder, an effective amount may depend on factors such as the disease state, age, sex, and weight of the individual, and the ability of the compound to elicit a desired response in the individual. In an example, an effective amount of a compound is an amount that produces a pharmacologically useful change in a given parameter as compared to a control, such as in cells (e.g., a culture of cells) or a subject not treated with the compound.

A therapeutic window over benzodiazepine-type CNS effects refers to having a desired therapeutic effect at a target organ (e.g., lung) at a dose or range of doses where benzodiazepine-type CNS effects (e.g., sedation) are at an acceptable level in the context of the particular therapeutic treatment. For example, in the context of asthma treatment acceptable levels of CNS effects include no CNS effects or mild CNS effects. For example, in some embodiments, the therapeutic index is 10 or more. In some embodiments, the therapeutic index is 20 or more. In some embodiments, the therapeutic index is 24 or more. Reduced benzodiazepine-type CNS effects includes reduced benzodiazepine-type CNS effects in a subject compared to diazepam at therapeutic doses. For example, in some embodiments, benzodiazepine-type CNS effects are reduced by 10-fold or more compared to diazepam at therapeutic doses. In some embodiments, benzodiazepine-type CNS effects are reduced by 20-fold or more compared to diazepam at therapeutic doses. In some embodiments, benzodiazepine-type CNS effects are reduced by 24-fold or more compared to diazepam at therapeutic doses.

It is specifically understood that any numerical value recited herein (e.g., ranges) includes all values from the lower value to the upper value, i.e., all possible combinations of numerical values between the lowest value and the highest value enumerated are to be considered to be expressly stated in this application. For example, if a concentration range is stated as 1% to 50%, it is intended that values such as 2% to 40%, 10% to 30%, or 1% to 3%, etc., are expressly enumerated in this specification. These are only examples of what is specifically intended.

Compounds

In a first aspect are provided compounds of formula (I), or a pharmaceutically acceptable salt thereof. Embodiments of formula (I) include the following descriptions of X, $R^1$, $R^2$, $R^{2'}$, and $R^3$, and any combinations thereof.

In some embodiments of formula (I), $R^3$ is OH when $R^1$ is a carboxylic ester or a carboxylic ester isostere; and/or $R^1$ is not a carboxylic ester or a carboxylic ester isostere when $R^3$ is H, F, Cl, Br, —OC$_{1-4}$alkyl, —C≡CH, or cyclopropyl; and/or $R^1$ is not a carboxylic amide, a carboxylic thioester

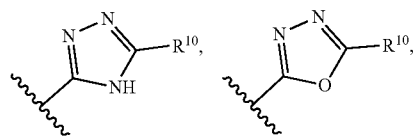

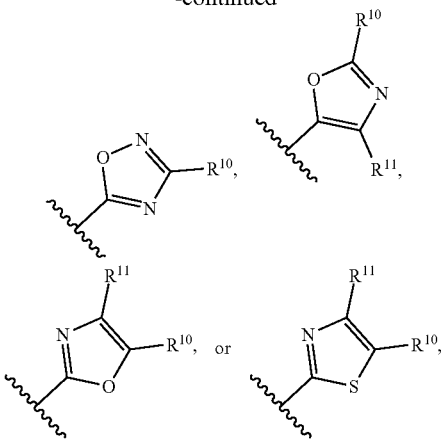

wherein $R^{10}$ and $R^{11}$ are independently H or $C_{1-6}$alkyl, when $R^3$ is —C≡CH; and/or $R^1$ is not COOH when $R^3$ is —C≡CH; and/or $R^1$ is not COOH, a carboxylic ester, a carboxylic amide, or a carboxylic thioester when $R^2$ and $R^{2'}$ are both H; X is C—H, C—F, C—Br, or C—I; and $R^3$ is H, F, Cl, or Br. In some embodiments, the compound of formula (I) is not (R)-8-ethynyl-6-(2-fluorophenyl)-4-methyl-4H-benzo[f]imidazo[1,5-a][1,4]diazepine-3-carboxylic acid. In some embodiments, $R^1$ is not COOH when $R^3$ is —C≡CH and $R^2$ or $R^{2'}$ are independently H or $C_{1-4}$alkyl.

In embodiments of formula (I), as described herein, X is C—H, C—F, C—Cl, C—Br, C—I, C—CF$_3$, or N. In further embodiments, X is C—H, C—F, C—Cl, C—Br, C—I, or N. In further embodiments, X is C—H, C—F, C—Cl, C—Br, or N.

In embodiments of formula (I), as described herein, $R^2$ and $R^{2'}$ are each independently H, D, $C_{1-4}$ alkyl, CD$_3$, F, Cl, CF$_3$, CCl$_3$, or cyclopropyl; or $R^2$ and $R^{2'}$ together form an optionally substituted ring. In further embodiments, $R^2$ and $R^{2'}$ are each independently H, $C_{1-4}$ alkyl, F, Cl, CF$_3$, CCl$_3$, or cyclopropyl; or $R^2$ and $R^{2'}$ together form a ring. In further embodiments, $R^2$ and $R^{2'}$ are each independently H, $C_{1-4}$ alkyl, F, Cl, CF$_3$, or CCl$_3$; or $R^2$ and $R^{2'}$ together form a ring. In still further embodiments, $R^2$ and $R^{2'}$ are each independently H, D, CH$_3$, CD$_3$, CF$_3$, or cyclopropyl; or $R^2$ and $R^{2'}$ together form a $C_{3-6}$cycloalkyl (e.g., cyclopropyl). In still further embodiments, $R^2$ and $R^{2'}$ together form a $C_{3-6}$cycloalkyl optionally substituted with 1-4 substituents independently selected from the group consisting of CH$_3$, F, OH, OCH$_3$, oxo, and CF$_3$.

In embodiments of formula (I), as described herein, $R^3$ is H, F, Cl, Br, CF$_3$, CHF$_2$, —OCF$_3$, —OCHF$_2$, CN, OH, —OC$_{1-4}$alkyl, —C≡CH, or cyclopropyl. In further embodiments, $R^3$ is H, F, Cl, Br, OH, OCH$_3$, —C≡CH, or cyclopropyl. In further embodiments, $R^3$ is H, F, Cl, OCH$_3$, or —C≡CH. In still further embodiments, $R^3$ is OH, wherein X, $R^1$, $R^2$, and $R^{2'}$, and combinations thereof, are as described herein. In some embodiments, $R^3$ is OH.

In further embodiments, $R^3$ is OH; X is C—H, C—F, C—Cl, C—Br, C—I, or N; and $R^2$ and $R^{2'}$ are each independently selected from $C_{1-4}$alkyl, F, Cl, CF$_3$, CCl$_3$, or cyclopropyl, or together form a ring; and $R^1$ is defined herein. In still further embodiments, $R^2$ and $R^{2'}$ together form a $C_{3-6}$cycloalkyl optionally substituted with 1-4 substituents independently selected from the group consisting of CH$_3$, F, OH, OCH$_3$, oxo, and CF$_3$. In some embodiments, one or more hydrogens may be replaced with a deuterium.

Suitably, the compound may be the S-isomer. Alternatively, the compound may be the R-isomer.

Embodiments of formula (I) include compounds of formula (I-A)

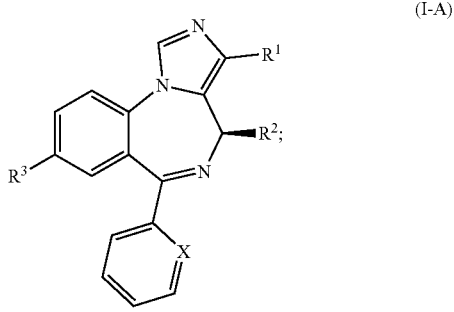

(I-A)

wherein $R^2$ is D, $C_{1-4}$ alkyl, $CD_3$, F, Cl, $CF_3$, $CCl_3$, or cyclopropyl, and combinations with X, $R^1$, and $R^3$ are as described herein. In some of the embodiments of formula (I-A), $R^2$ is D, $CH_3$, $CD_3$, $CF_3$, or cyclopropyl. In some embodiments of formula (I-A) according to the foregoing, $R^3$ is OH.

Embodiments of formula (I) include compounds of formula (I-B)

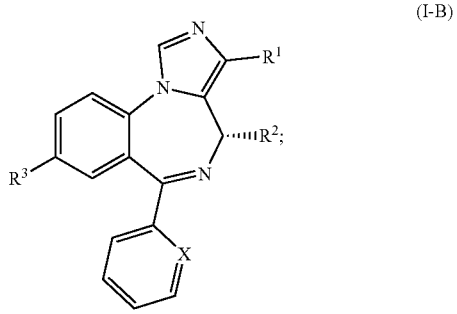

(I-B)

wherein $R^{2'}$ is D, $C_{1-4}$ alkyl, $CD_3$, F, Cl, $CF_3$, $CCl_3$, or cyclopropyl, and combinations with X, $R^1$, and $R^3$ are as described herein. In some of the embodiments of formula (I-B), $R^{2'}$ is D, $CH_3$, $CD_3$, $CF_3$, or cyclopropyl. In some embodiments of formula (I-B) according to the foregoing, $R^3$ is OH.

Embodiments of formula (I) include compounds of formula (I-C)

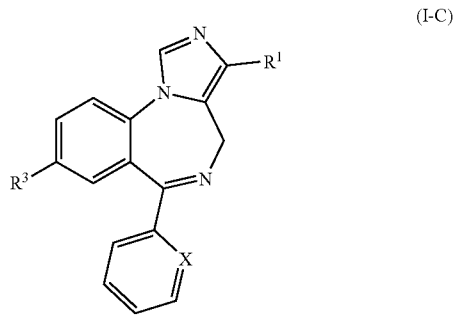

(I-C)

wherein X, $R^1$, and $R^3$ and combinations thereof, are as described herein. In some embodiments of formula (I-C) according to the foregoing, $R^3$ is OH.

In some combinations of X, $R^2$, $R^{2'}$, and $R^3$, X is C—H, C—F, C—Cl, C—Br, C—I, or N; $R^2$ is $C_{1-4}$ alkyl, $CD_3$, F, Cl, $CF_3$, $CCl_3$, or cyclopropyl; $R^{2'}$ is H or D; and $R^3$ is H, F, Cl, Br, OH, $OCH_3$, —C≡CH, or cyclopropyl. In some of the embodiments, $R^2$ is $C_{1-4}$ alkyl (e.g., $CH_3$). In further embodiments, $R^3$ is H, F, Cl, Br, OH, $OCH_3$, or cyclopropyl, and $R^2$ is $C_{1-4}$ alkyl. In further combinations with the foregoing, $R^1$ is COOH.

In some embodiments, the invention provides a compound according to formula (I) wherein $R^1$ is a carboxylic acid isostere; X is C—H, C—F, C—Cl, C—Br, C—I, or N; $R^2$ and $R^{2'}$ are independently selected from H, $C_{1-4}$ alkyl, F, Cl, $CF_3$, $CCl_3$, or cyclopropyl, or together form a ring; and $R^3$ is selected from H, F, Cl, Br, OMe, —C≡CH, or cyclopropyl. In still further embodiments, $R^2$ and $R^{2'}$ together form a $C_{3-6}$cycloalkyl optionally substituted with 1-4 substituents independently selected from the group consisting of $CH_3$, F, OH, $OCH_3$, oxo, and $CF_3$. In embodiments, $R^2$ and $R^{2'}$ are H and (R)-Me, or H and (S)-Me, or $R^2$ and $R^{2'}$ are both H. In some embodiments, one or more hydrogens may be replaced with a deuterium. Suitably, the compound may be the S-isomer. Alternatively, the compound may be the R-isomer.

In another embodiment of formula (I), $R^1$ is COOH; X is C—H, C—F, C—Cl, C—Br, C—I, or N; $R^2$ and $R^{2'}$ are independently selected from $C_{1-4}$ alkyl, F, Cl, $CF_3$, $CCl_3$, or cyclopropyl, or together form a ring; and $R^3$ is selected from H, F, Cl, Br, OMe, —C≡CH, Br, or cyclopropyl. In still further embodiments, $R^2$ and $R^{2'}$ together form a $C_{3-6}$cycloalkyl optionally substituted with 1-4 substituents independently selected from the group consisting of $CH_3$, F, OH, $OCH_3$, oxo, and $CF_3$. In some embodiments, one or more hydrogens may be replaced with a deuterium. Suitably, the compound may be the S-isomer. Alternatively, the compound may be the R-isomer.

In another aspect are provided compounds of formula (II), or a pharmaceutically acceptable salt thereof. Embodiments of formula (II) include the following descriptions of X, $R^1$, and $R^3$, and combinations thereof.

In some embodiments of formula (II), $R^3$ is OH when $R^1$ is COOH, a carboxylic ester, a carboxylic amide, or a carboxylic thioester. In other embodiments, $R^3$ is OH when $R^1$ is COOH. In other embodiments, $R^1$ is not a carboxylic ester, a carboxylic amide, or a carboxylic thioester. In other embodiments, $R^1$ is not a carboxylic ester, a carboxylic amide, or a carboxylic thioester when $R^3$ is —$OC_{1-4}$alkyl or OH. In some embodiments, the compound of formula (II) is not ethyl (S)-7-hydroxy-9-oxo-11,12,13,13a-tetrahydro-9H-benzo[e]imidazo[5,1-c]pyrrolo[1,2-a][1,4]diazepine-1-carboxylate.

In embodiments of formula (II), as described herein, $R^3$ is H, F, Cl, Br, $CF_3$, $CHF_2$, —$OCF_3$, —$OCHF_2$, CN, OH, —$OC_{1-4}$alkyl, —C≡CH, or cyclopropyl. In further embodiments, $R^3$ is H, F, Cl, Br, OH, —$OCH_3$, —C≡CH, or cyclopropyl. In further embodiments, $R^3$ is H, F, Cl, Br, —$OCH_3$, or —C≡CH. In further embodiments, $R^3$ is H, F, Cl, —$OCH_3$, or —C≡CH. In still further embodiments, $R^3$ is OH. In further embodiments, $R^3$ is OH, wherein X and $R^1$, and combinations thereof, are as described herein.

In certain combinations, $R^1$ is a carboxylic acid isostere and $R^3$ is H, F, Cl, Br, $CF_3$, $CHF_2$, —$OCF_3$, —$OCHF_2$, CN, —$OC_{1-4}$alkyl, —C≡CH, or cyclopropyl. In other combinations, $R^1$ is COOH, a carboxylic ester, a carboxylic acid isostere, or a carboxylic ester isostere; and $R^3$ is OH.

Embodiments of formula (II) include compounds of formula (II-A)

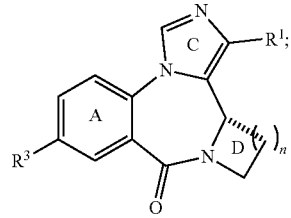
(II-A)

wherein X, R¹, and R³ are as described herein. In some of the embodiments of formula (II-A) according to the foregoing, R³ is OH. In certain combinations, R¹ is a carboxylic acid isostere and R³ is H, F, Cl, Br, CF₃, CHF₂, —OCF₃, —OCHF₂, CN, —OC$_{1-4}$alkyl, —C≡CH, or cyclopropyl. In certain combinations, R¹ is a carboxylic acid isostere and R³ is H, F, Cl, Br, OH, —OCH₃, —C≡CH, or cyclopropyl. In other combinations, R¹ is COOH, a carboxylic ester, a carboxylic acid isostere, or a carboxylic ester isostere; and R³ is OH.

Embodiments of formula (II) include compounds of formula (II-B)

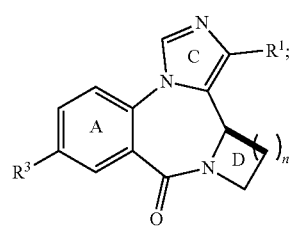
(II-B)

wherein X, R¹, and R³ are as described herein. In some of the embodiments of formula (II-B) according to the foregoing, R³ is OH. In certain combinations, R¹ is a carboxylic acid isostere and R³ is H, F, Cl, Br, CF₃, CHF₂, —OCF₃, —OCHF₂, CN, —OC$_{1-4}$alkyl, —C≡CH, or cyclopropyl. In certain combinations, R¹ is a carboxylic acid isostere and R³ is H, F, Cl, Br, OH, —OCH₃, —C≡CH, or cyclopropyl. In other combinations, R¹ is COOH, a carboxylic ester, a carboxylic acid isostere, or a carboxylic ester isostere; and R³ is OH.

Unless otherwise stated, the embodiments described herein include further embodiments wherein R¹ is COOH. Unless otherwise stated, the embodiments described herein include further embodiments wherein R¹ is a carboxylic ester. In some embodiments, the carboxylic ester is —C(O)OC$_{1-6}$alkyl or —C(O)OC$_{3-6}$cycloalkyl. Unless otherwise stated, the embodiments described herein include further embodiments wherein R¹ is carboxylic acid isostere. Unless otherwise stated, the embodiments described herein include further embodiments wherein R¹ is a carboxylic ester isostere.

Included in the embodiments described herein, are still further embodiments wherein R¹ is

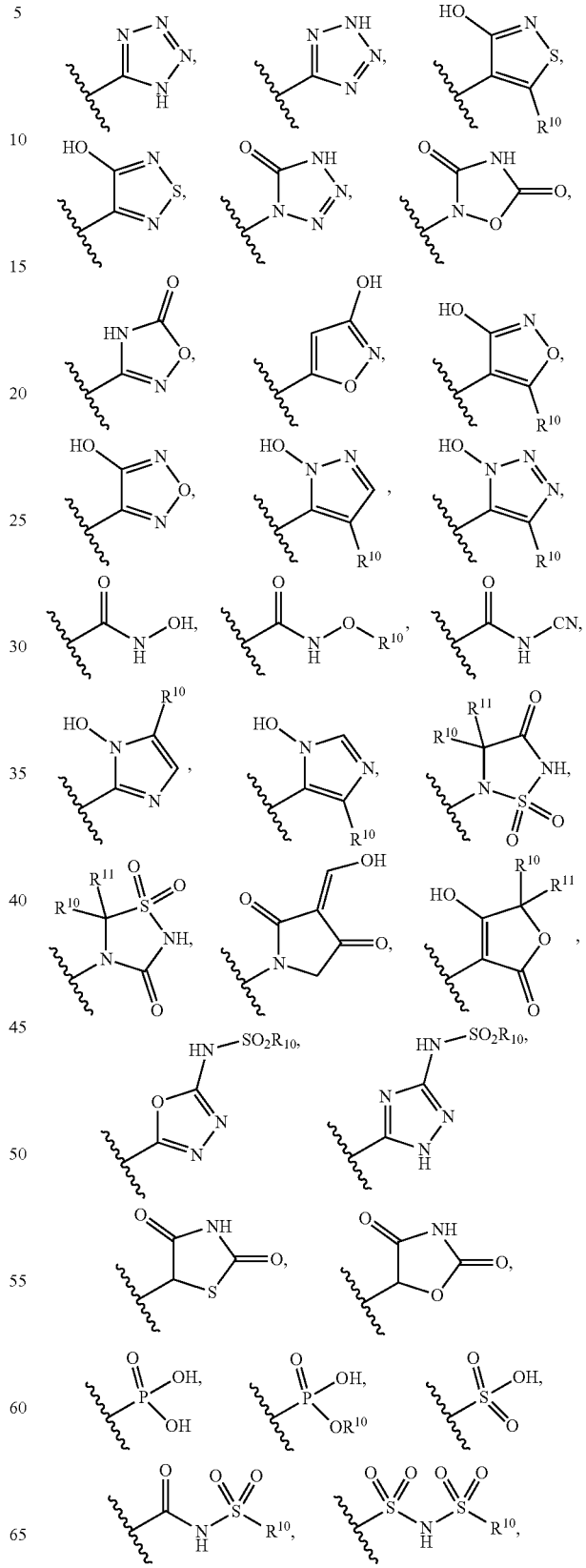

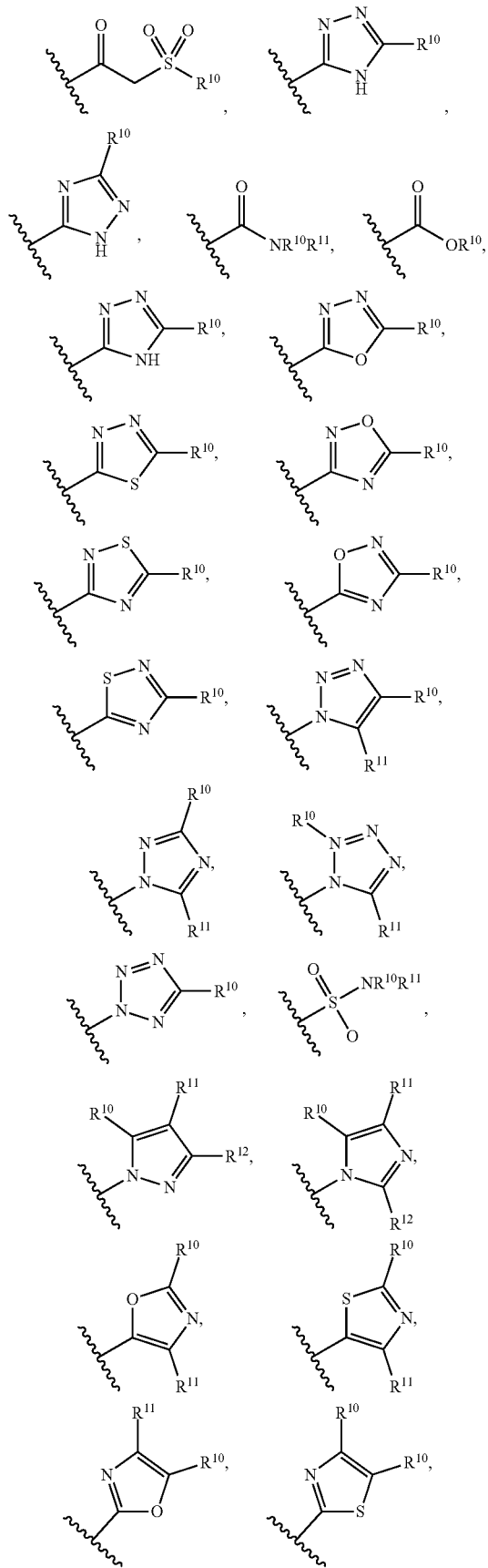
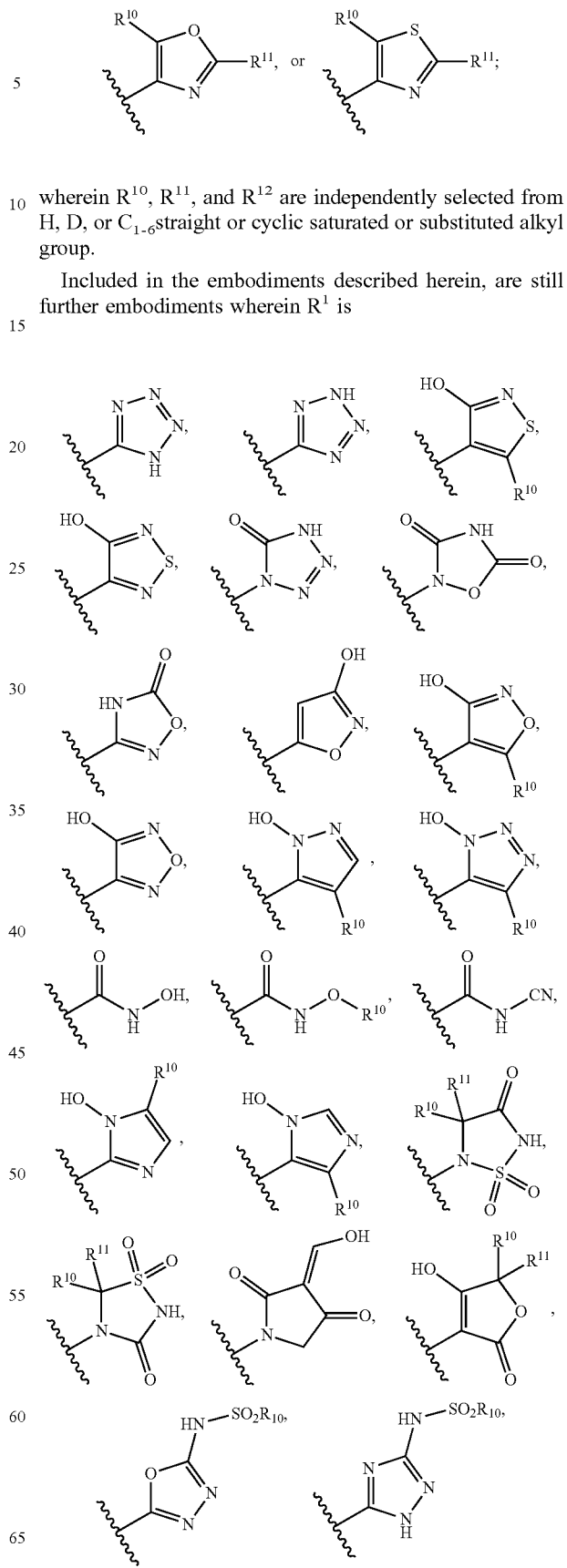
wherein $R^{10}$, $R^{11}$, and $R^{12}$ are independently selected from H, D, or $C_{1-6}$ straight or cyclic saturated or substituted alkyl group.
Included in the embodiments described herein, are still further embodiments wherein $R^1$ is -continued

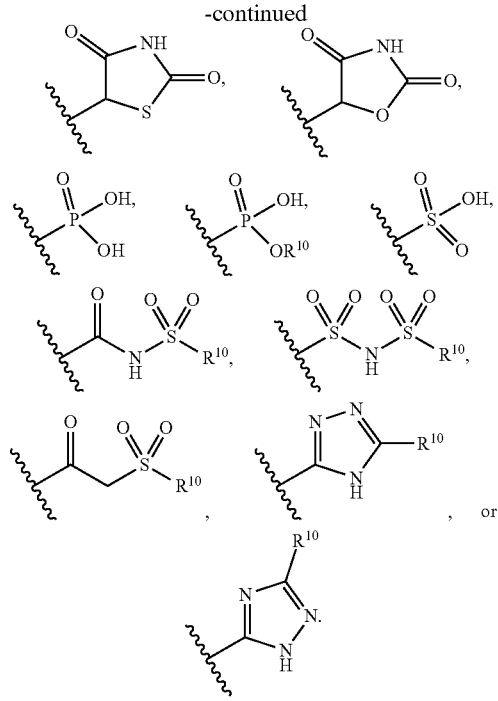

The foregoing $R^1$ group members are included in the term "carboxylic acid isostere." In further embodiments, $R^1$ is

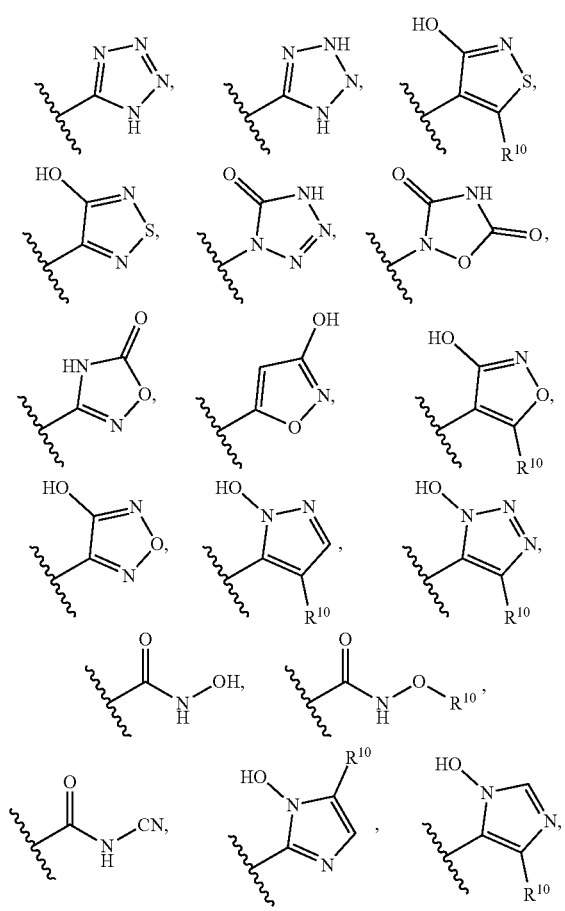

-continued

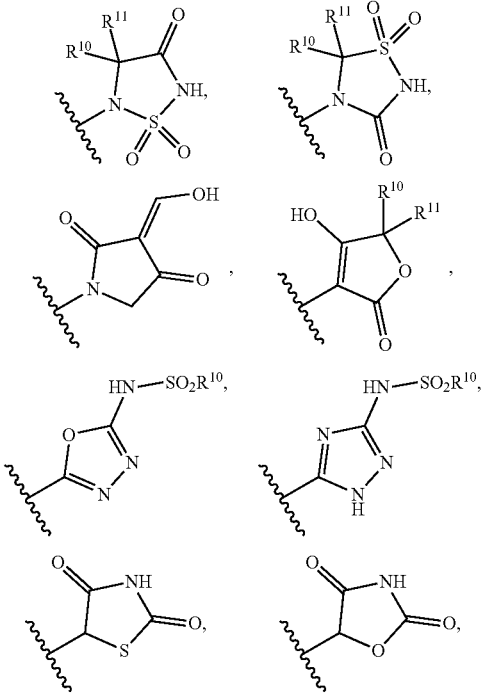

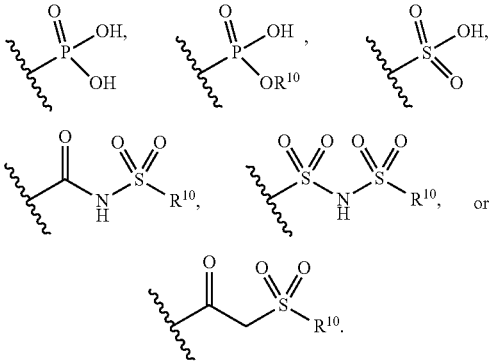

In still further embodiments, and combinations, $R^{10}$, $R^{11}$, and $R^{12}$ are independently H, D, $C_{1-6}$alkyl, or $C_{3-6}$cycloalkyl.

In still further embodiments, $R^1$ is a tetrazole

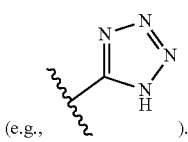

(e.g., ).

According to the foregoing, a carboxylic ester isostere includes

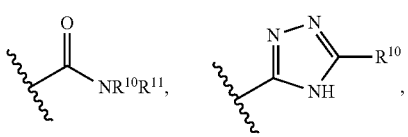

In another aspect, the invention provides a compound selected from the group consisting of:

- (R)-8-ethynyl-6-(2-fluorophenyl)-4-methyl-4H-benzo[f]imidazo[1,5-a][1,4]diazepine-3-carboxylic acid (SH-053-2'F—R—CH₃ Acid);
- (R)-8-bromo-6-(2-fluorophenyl)-4-methyl-4H-benzo[f]imidazo[1,5-a][1,4]diazepine-3-carboxylic acid (GL-II-93);
- (R)-8-cyclopropyl-6-(2-fluorophenyl)-4-methyl-4H-benzo[f]imidazo[1,5-a][1,4]diazepine-3-carboxylic acid (GL-III-43);
- (R)-8-chloro-6-(2-fluorophenyl)-4-methyl-4H-benzo[f]imidazo[1,5-a][1,4]diazepine-3-carboxylic acid (GL-III-54);
- (R)-8-bromo-4-methyl-6-(pyridin-2-yl)-4H-benzo[f]imidazo[1,5-a][1,4]diazepine-3-carboxylic acid (GL-II-51);
- (R)-8-ethynyl-4-methyl-6-(pyridin-2-yl)-4H-benzo[f]imidazo[1,5-a][1,4]diazepine-3-carboxylic acid (GL-II-30);
- (S)-7-methoxy-1-(1H-tetrazol-5-yl)-11,12,13,13a-tetrahydro-9H-benzo[e]imidazo[5,1-c]pyrrolo[1,2-a][1,4]diazepin-9-one (RJ-03-57);
- (S)—N,7-dimethoxy-9-oxo-11,12,13,13a-tetrahydro-9H-benzo[e]imidazo[5,1-c]pyrrolo[1,2-a][1,4]diazepine-1-carboxamide (MRS-III-87);
- (S)—N-cyano-7-methoxy-9-oxo-11,12,13,13a-tetrahydro-9H-benzo[e]imidazo[5,1-c]pyrrolo[1,2-a][1,4]diazepine-1-carboxamide (MRS-III-90);
- ethyl (S)-7-hydroxy-9-oxo-11,12,13,13a-tetrahydro-9H-benzo[e]imidazo[5,1-c]pyrrolo[1,2-a][1,4]diazepine-1-carboxylate (RJ-02-50);
- (S)-7-hydroxy-9-oxo-11,12,13,13a-tetrahydro-9H-benzo[e]imidazo[5,1-c]pyrrolo[1,2-a][1,4]diazepine-1-carboxylic acid (RJ-03-90);
- (S)-7-hydroxy-1-(oxazol-5-yl)-11,12,13,13a-tetrahydro-9H-benzo[e]imidazo[5,1-c]pyrrolo[1,2-a][1,4]diazepin-9-one (RJ-03-30); and
- tert-butyl (S)-7-hydroxy-9-oxo-11,12,13,13a-tetrahydro-9H-benzo[e]imidazo[5,1-c]pyrrolo[1,2-a][1,4]diazepine-1-carboxylate (RJ-02-67);

or a pharmaceutically acceptable salt thereof.

In another aspect, the invention provides a compound selected from the group consisting of:

- 5-(8-ethynyl-6-(pyridin-2-yl)-4H-benzo[f]imidazo[1,5-a][1,4]diazepin-3-yl)oxazole (KRM-II-81);
- 5-(8-ethynyl-6-phenyl-4H-benzo[f]imidazo[1,5-a][1,4]diazepin-3-yl)oxazole (KRM-II-82);
- 5-(8-ethynyl-6-(2-fluorophenyl)-4H-benzo[f]imidazo[1,5-a][1,4]diazepin-3-yl)oxazole (KRM-II-18B);
- methyl (R)-8-ethynyl-6-(2-fluorophenyl)-4-methyl-4H-benzo[f]imidazo[1,5-a][1,4]diazepine-3-carboxylate (MP-III-004);
- (R)-8-ethynyl-6-(2-fluorophenyl)-N,4-dimethyl-4H-benzo[f]imidazo[1,5-a][1,4]diazepine-3-carboxamide (MP-III-022);
- ethyl-1,1-d₂ 8-ethynyl-6-(pyridin-2-yl)-4H-benzo[f]imidazo[1,5-a][1,4]diazepine-3-carboxylate (MP-III-068);
- 5-(8-ethynyl-6-(pyridin-2-yl)-4H-benzo[f]imidazo[1,5-a][1,4]diazepin-3-yl)-3-methyl-1,2,4-oxadiazole (MP-III-085);
- 3-ethyl-5-(8-ethynyl-6-(pyridin-2-yl)-4H-benzo[f]imidazo[1,5-a][1,4]diazepin-3-yl)-1,2,4-oxadiazole (MP-III-080);
- ethyl 8-ethynyl-6-phenyl-4H-benzo[f]imidazo[1,5-a][1,4]diazepine-3-carboxylate (XHe-II-053);
- ethyl 8-ethynyl-6-(pyridin-2-yl)-4H-benzo[f]imidazo[1,5-a][1,4]diazepine-3-carboxylate (HZ-166); and
- ethyl 8-ethynyl-6-(2-fluorophenyl)-4H-benzo[f]imidazo[1,5-a][1,4]diazepine-3-carboxylate (JY-XHe-053);

or a pharmaceutically acceptable salt thereof.

For compounds according to the present invention, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., —CH$_2$O— optionally also recites —OCH$_2$—.

Compounds according to the present invention include compounds that differ only in the presence of one or more isotopically enriched atoms. For example, compounds may have the present structures except for the replacement of hydrogen by deuterium or tritium, or the replacement of a carbon by a $^{13}$C- or $^{14}$C-enriched carbon.

A compound according to the present invention can be in the form of a salt, e.g., a pharmaceutically acceptable salt. The term "pharmaceutically acceptable salt" includes salts of the active compounds that are prepared with relatively nontoxic acids or bases, depending on the particular substituents found on the compounds. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulfuric acid, methanesulfonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts, alkaline earth metal salts, e.g. calcium or magnesium salts; and salts formed with suitable organic ligands, e.g. quaternary ammonium salts.

Neutral forms of the compounds may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure.

In addition to salt forms, the present invention may also provide compounds according to the present invention in a prodrug form. Prodrugs of the compounds are those compounds that readily undergo chemical changes under physiological conditions to provide the active compounds. Prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Compounds described herein may exist as stereoisomers wherein asymmetric (or chiral) centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

Compounds according to the present invention can be, for example, an enantiomerically enriched isomer of a stereoisomer described herein. Enantiomer, as used herein, refers to either of a pair of chemical compounds whose molecular structures have a mirror-image relationship to each other. For example, a compound may have an enantiomeric excess of at least about 10%, 15%, 20%, 25%, 30%, 35%, 40%, 45%, 50%, 55%, 60%, 65%, 70%, 75%, 80%, 85%, 90%, 95%, 96%, 97%, 98%, or 99%.

A preparation of a compound according to the present invention may be enriched for an isomer of the compound having a selected stereochemistry, e.g., R or S, corresponding to a selected stereocenter. For example, the compound may have a purity corresponding to a compound having a selected stereochemistry of a selected stereocenter of at least about 60%, 65%, 70%, 75%, 80%, 85%, 90%, 95%, 96%, 97%, 98%, or 99%. A compound can, for example, include a preparation of a compound disclosed herein that is enriched for a structure or structures having a selected stereochemistry, e.g., R or S, at a selected stereocenter.

In some embodiments, a preparation of a compound according to the present invention may be enriched for isomers (subject isomers) which are diastereomers of the compound. Diastereomer, as used herein, refers to a stereoisomer of a compound having two or more chiral centers that is not a mirror image of another stereoisomer of the same compound. For example, the compound may have a purity corresponding to a compound having a selected diastereomer of at least about 60%, 65%, 70%, 75%, 80%, 85%, 90%, 95%, 96%, 97%, 98%, or 99%.

When no specific indication is made of the configuration at a given stereocenter in a compound, any one of the configurations or a mixture of configurations is intended. The formulae within this specification can represent only one of the possible tautomeric forms. It is to be understood that encompassed herein are any tautomeric form, and mixtures thereof, and is not to be limited merely to any one tautomeric form utilized within the naming of the compounds or formulae Compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. The enantiomers also may be obtained from kinetic resolution of the racemate of corresponding esters using lipase enzymes.

A compound according to the present invention can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include, but are not limited to, esterification with polyethylene glycols, derivatization with pivolates or fatty acid substituents, conversion to carbamates, hydroxylation of aromatic rings, and heteroatom substitution in aromatic rings.

The compounds of the present invention may also be adapted as "soft drugs". A soft drug may be defined as a biologically active compound having predictable and controllable in vivo metabolism to inert species after it achieves its desired therapeutic effect. That is, the compounds of the present invention may contain a moiety which allows for rapid metabolism of the compounds in the lung or other target tissue. In lungs, several cytochrome isoforms are found, as well as other biotransformation enzymes such as sulfotransferases, UDP glucuronosyl transferases, glutathione S-transferases, esterases, peptidases, cyclo-oxygenases, and flavine mono-oxygenases. The wide range of biotransformation enzymes enables metabolism of a broad spectrum of chemically different substrates, for example compounds with a labile ester function. Soft drugs would have shorter systemic half-life than compounds without the moiety and may limit undesirable systemic effects (such a distribution to CNS tissues).

Synthesis of Compounds

Compounds of formulae (I) and (II) may be synthesized using commercially available starting materials. Exemplary syntheses are summarized in Schemes 1-5 and in (Cook, J. M, Zhou, H., Huang S., Sarma, P. V. V. S., Zhang, C., 2009. *Stereospecific anxiolytic and anticonvulsant agents with reduced muscle-relaxant, sedative hypnotic and ataxic effects*, PCTWO2006/004945A1, U.S. Pat. No. 7,618,958).

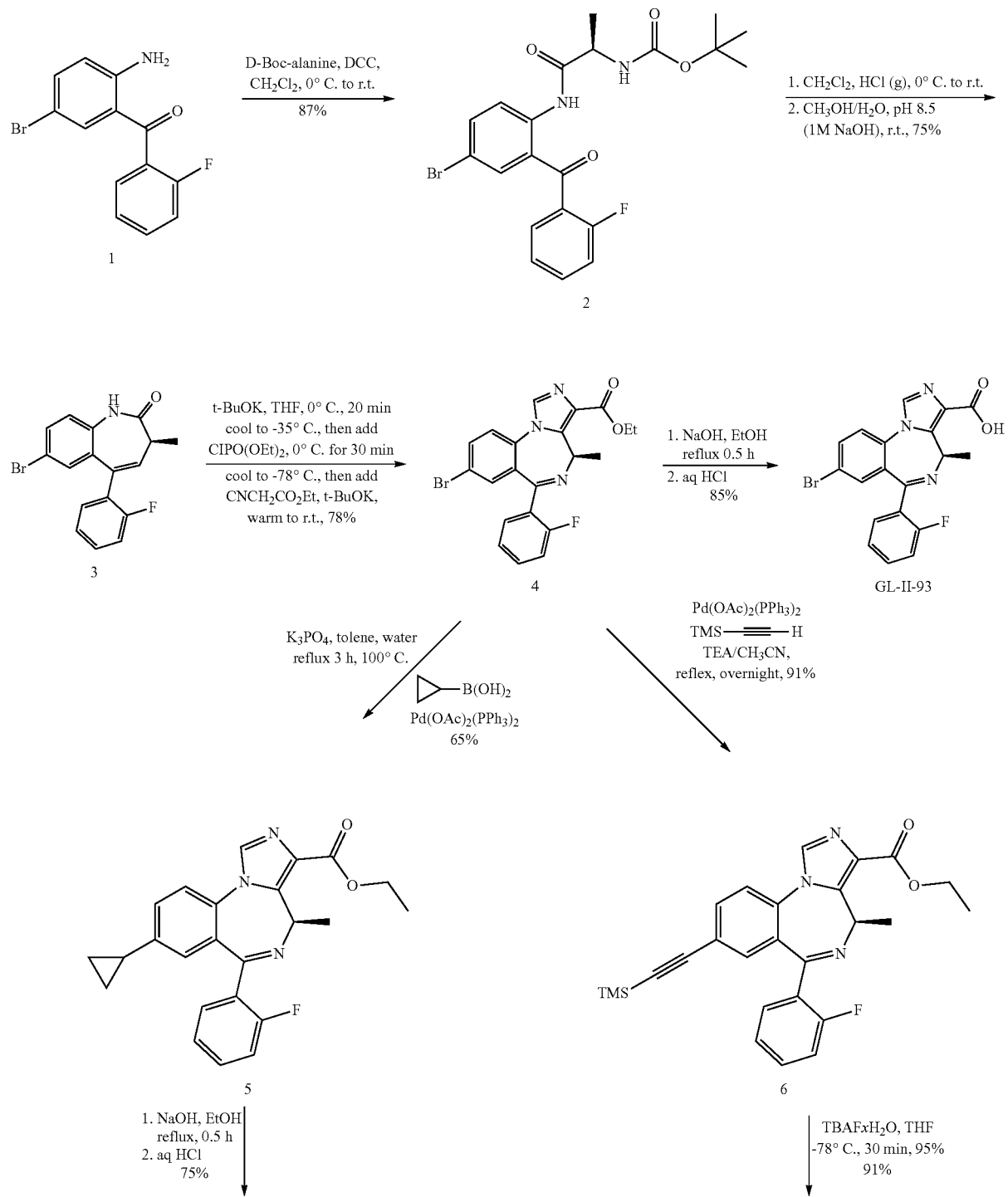

Scheme 1. Synthesis of compounds with formulae (I) part I.

-continued
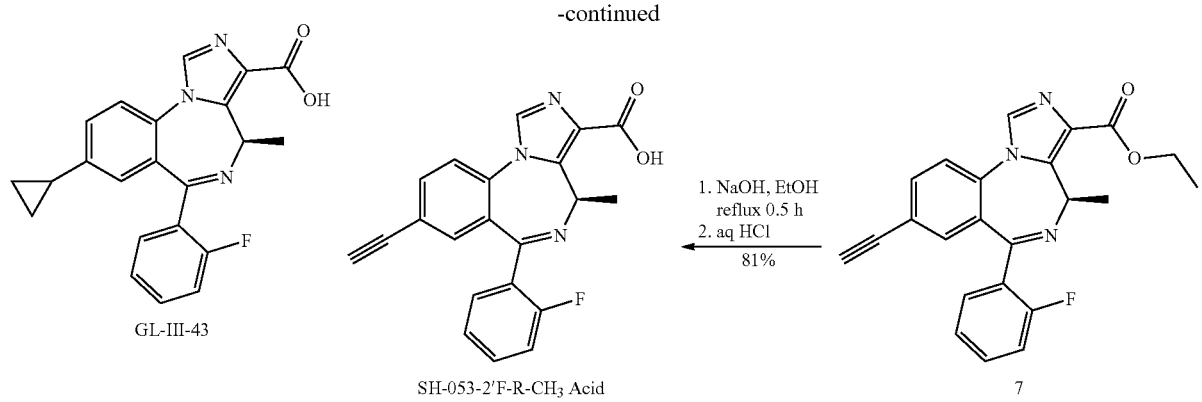
GL-III-43
SH-053-2′F-R-CH₃ Acid
Scheme 2. Synthesis of compounds with formulae (I) part II.
Scheme 3. Synthesis of compounds with formulae (I) part III.
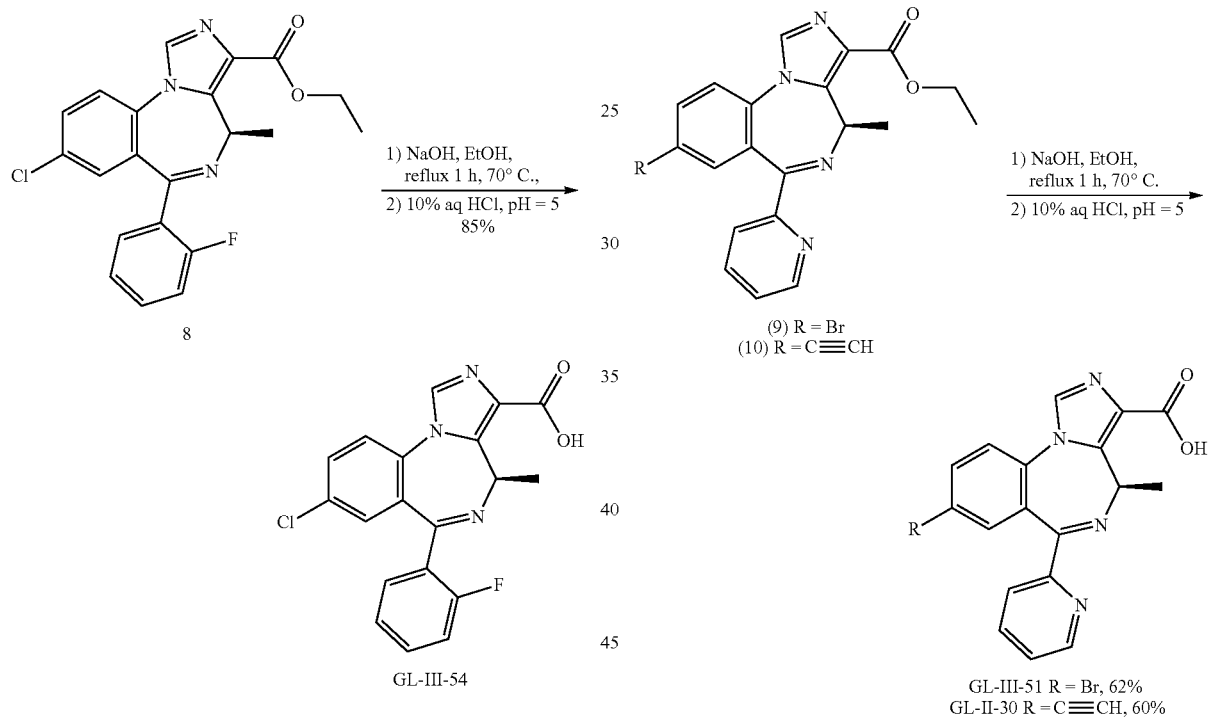
GL-III-54
GL-III-51 R = Br, 62%
GL-II-30 R = C≡CH, 60%
Scheme 4. Synthesis of compounds with formulae (II).
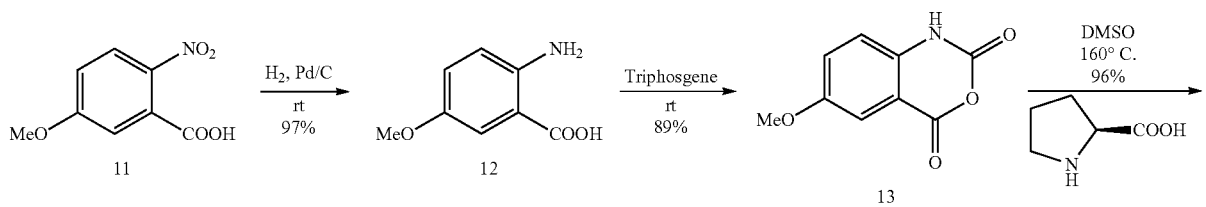

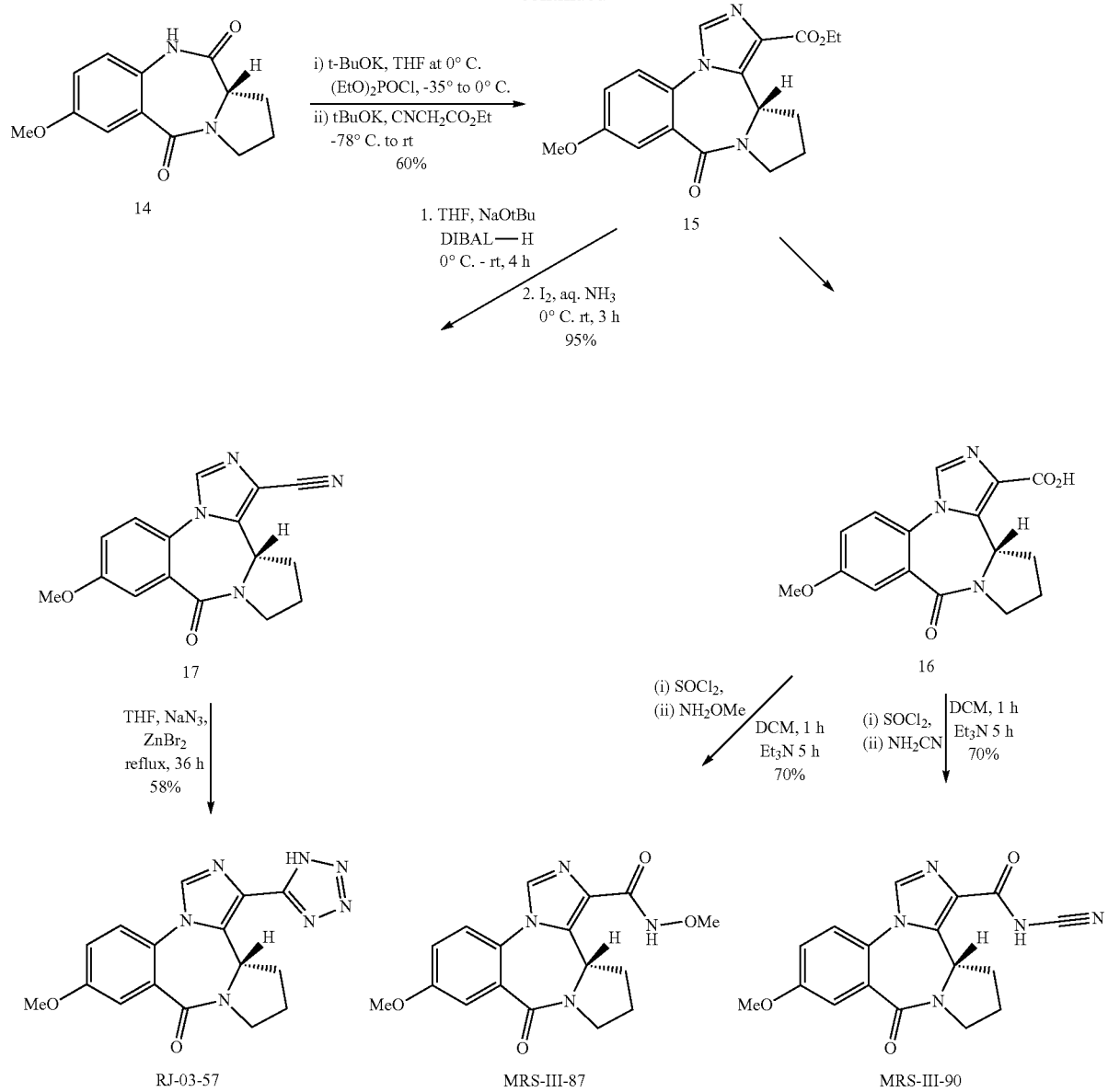
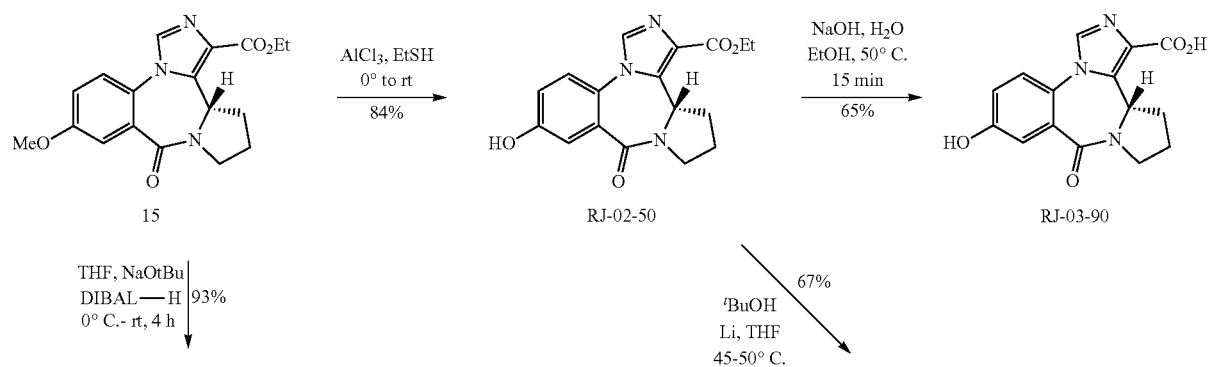
Scheme 5. Synthesis of compounds with formulae (II).

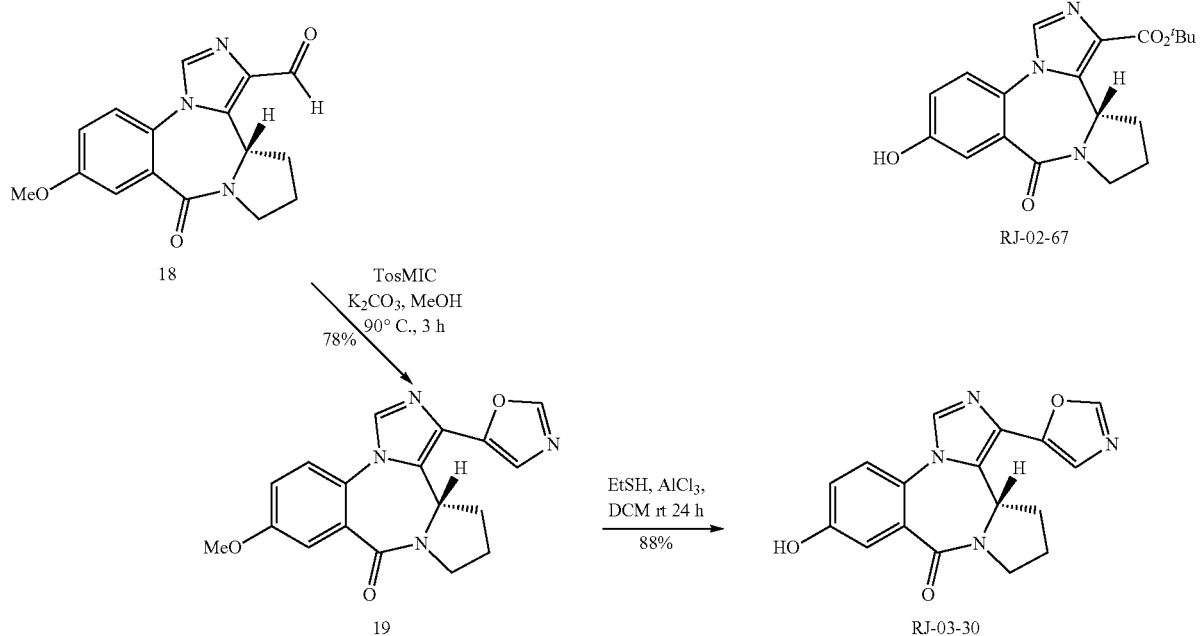

Compounds of formulae (II) may be synthesized using commercially available starting materials. Exemplary syntheses are illustrated in the Exhibits hereto and in (Jahan et al. *European J. Med Chem.* 2017, 126, 550-560).

Other methods of synthesizing the compounds of the formulae herein will be evident to those of ordinary skill in the art. Synthetic chemistry transformations and protecting group methodologies (protection and deprotection) useful in synthesizing the compounds are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Evaluation of Compounds

Compounds may be analyzed using a number of methods, including receptor binding studies and in vivo methods.

For example, the $GABA_A$ subunit selectivity of compounds can be evaluated, for example, using competitive binding assays. Such assays have been described (Choudhary et al. *Mol Pharmacol.* 1992, 42, 627-33; Savić et al. *Progress in Neuro-Psychopharmacology & Biological Psychiatry*, 2010, 34, 376-386). The assays involve the use of a radiolabeled compound known to bind to $GABA_A$ receptors, such as [$^3$H]flunitrazepam. Membrane proteins can be harvested and incubated with the radiolabeled compound, and non-specific binding can be evaluated by comparing binding of the radiolabeled compound to another, non-labeled compound (e.g., diazepam). Bound radioactivity can be quantified by liquid scintillation counting. Membrane protein concentrations can be determined using commercially available assay kits (e.g., from Bio-Rad, Hercules, CA).

Compounds can also be evaluated in electrophysiological assays in *Xenopus* oocytes or HEK293T cells that overexpress a particular $GABA_AR$ subtype. Compounds can be pre-applied to cells before the addition of GABA, which can then be co-applied with the compounds until a peak response is observed. Between applications, cells can be washed to ensure full recovery from desensitization. For current measurements, cells can be impaled with microelectrodes, and recordings performed using voltage clamps.

Compounds described herein may be $GABA_A$ receptor ligands which bind to endogenous airway smooth muscle $GABA_A$ receptors and potentiate relaxation of cholinergic airway smooth muscle contraction. This is due to increased targeting for the benzodiazepine allosteric modulatory sites at the α4 and α5 subunits. The compounds may possess at least 2-fold, suitably at least 5-fold, and advantageously at least a 10-fold, selective efficacy for the $GABA_A$/α4 and/or $GABA_A$/α5 allosteric modulatory sites relative to those $GABA_A$/α1, $GABA_A$/α2, and $GABA_A$/α3. However, compounds which are not selective for the benzodiazepine allosteric modulatory binding sites on $GABA_A$/α4 and/or $GABA_A$/α5 receptors are also encompassed within the scope of the present invention. Such compounds will desirably exhibit functional selectivity by demonstrating decreased efficacy at the benzodiazepine allosteric modulatory sites of other $GABA_A$ receptors.

A selective or preferential therapeutic agent has less binding affinity or efficacy to the other benzodiazepine allosteric modulatory sites on $GABA_A$ receptors as compared to the benzodiazepine allosteric modulatory sites on the $GABA_A$/α4 or $GABA_A$/α5 subunits. Alternatively, the agent targets benzodiazepine allosteric modulatory sites on all $GABA_A$ receptors with a comparable affinity but exerts preferential efficacy for the benzodiazepine allosteric modulatory sites on $GABA_A$/α$_4$ and $GABA_A$/α$_5$ receptors compared to those on other $GABA_A$ receptors. A selective agent of the present invention can also have a greater or lesser ability to bind benzodiazepine allosteric modulatory sites on other $GABA_A$ receptors relative to $GABA_A$/α$_2$ and $GABA_A$/α$_3$ receptors.

Other methods for evaluating compounds are known to those skilled in the art. To assess a compound's undesirable side effects (toxicity), animals may monitored for overt signs of impaired neurological or muscular function. In mice, the rotarod procedure (Dunham, M. S. et al. *J. Amer. Pharm. Ass. Sci. Ed.* 1957, 46, 208-209) is used to disclose minimal muscular or neurological impairment. When a mouse is placed on a rod that rotates at a speed of 6 revolutions-per-minute (rpm), the animal can maintain its equilibrium for long periods of time. The compound is considered toxic if it falls off this rotating rod three times during a 1-minute period. In rats, minimal motor deficit is indicated by ataxia, which is manifested by an abnormal, uncoordinated gait. Rats used for evaluating toxicity are examined before the test drug is administered, since individual animals may have peculiarities in gait, equilibrium, placing response, etc., which might be attributed erroneously to the test substance. Animals may exhibit a circular or zigzag gait, abnormal body posture and spread of the legs, tremors, hyperactivity, lack of exploratory behavior, somnolence, stupor, catalepsy, loss of placing response and changes in muscle tone.

Compounds described herein may reduce airway hyper-responsiveness in animal models of asthma. Therefore, mice may be sensitized three times with intra-peritoneal (i.p.) injections of 2 mg/kg/d of ovalbumin (Ova) emulsified in 2 mg on days 0, 7 and 14 in a total volume of 100 µL. In addition, mice may be challenged intra-nasally (i.n.) with 1 mg/kg/d Ova for 5 days from days 23-27. Control mice may be sensitized with Ova and challenged with saline. The airway hyperresponsiveness measurements may be carried out with DSI's Buxco® FinePointe Non-Invasive Airway Mechanics (NAM) instrument consisting of a nasal chamber in combination with the thoracic chamber that allows the computation of specific airway resistance (sRaw). Treated conscious, spontaneously breathing Ova S/C mice may be exposed to aerosolized phosphate buffered saline (PBS) (for the baseline measurement) or methacholine (1.5625-12.5 mg/mL) for 1 minute and readings (sRaw) may be taken and averaged for 3 minutes after each nebulization.

The change of the number of specific immune cells caused by compounds may be investigated in the broncho-alveolar lavage fluid (BALF) of Ova S/C mice. Therefore, a bronchoalveolar lavage may be carried out followed by the lysis of red blood cells. Incubation of cell-type specific antibodies with BALF may allow the quantification of leukocytes such as eosinophils and $CD4^+$ T-lymphocytes using flow cytometry.

Direct interaction between compounds and $CD4^+$ T cells may be investigated by electrophysiology. Therefore, $CD4^+$ T cells may be isolated from the spleen of asthmatic mice and treated with compounds during an automated patch clamp experiment.

The change of cytokine expression caused by compounds may be investigated in the lung of Ova S/C mice. Therefore, lungs of treated and non-treated asthmatic mice may be harvested, homogenized and cleared by centrifugation. Cytokines may be identified and quantified with specific antibodies and flow cytometry.

The pharmacokinetic properties of compounds may be investigated in animals. Therefore, animals may be exposed to compounds for different time intervals. Quantification of compounds concentrations may occur for blood, lung and brain using specific preparation protocols followed by quantification using mass spectrometry.

The cytotoxicity of compounds may be evaluated by treating HEK293 human embryonic kidney cells with increasing concentrations of compounds for 24-48 hours followed by the quantification of living cells using Cell-Titer Glo (Promega).

Compositions and Routes of Administration

In another aspect, the invention provides pharmaceutical compositions comprising one or more compounds of this invention in association with a pharmaceutically acceptable carrier. Such compositions may be in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. It is also envisioned that compounds may be incorporated into transdermal patches designed to deliver the appropriate amount of the drug in a continuous fashion. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Suitable dosage level is about 0.01 to 250 mg/kg per day, about 0.05 to 100 mg/kg per day, or about 0.05 to 5 mg/kg per day. The compounds may be administered on a regimen of 1 to 4 times per day, or on a continuous basis via, for example, the use of a transdermal patch.

Pharmaceutical compositions for enteral administration, such as nasal, buccal, rectal, sub-lingual or, especially, oral administration, and for parenteral administration, such as intravenous, intramuscular, subcutaneous, peridural, epidural or intrathecal administration, are suitable. The pharmaceutical compositions comprise from approximately 1% to approximately 95% active ingredient, or from approximately 20% to approximately 90% active ingredient.

For parenteral administration including intracoronary, intracerebrovascular, or peripheral vascular injection/infusion preference is given to the use of solutions of the subunit selective GABAA receptor agonist, and also suspensions or dispersions, especially isotonic aqueous solutions, dispersions or suspensions which, for example, can be made up shortly before use. The pharmaceutical compositions may be sterilized and/or may comprise excipients, for example preservatives, stabilizers, wetting agents and/or emulsifiers, solubilizers, viscosity-increasing agents, salts for regulating osmotic pressure and/or buffers and are prepared in a manner known per se, for example by means of conventional dissolving and lyophilizing processes.

For oral pharmaceutical preparations suitable carriers are especially fillers, such as sugars, for example lactose, saccharose, mannitol or sorbitol, cellulose preparations and/or calcium phosphates, and also binders, such as starches, cellulose derivatives and/or polyvinylpyrrolidone, and/or, if desired, disintegrators, flow conditioners and lubricants, for example stearic acid or salts thereof and/or polyethylene glycol. Tablet cores can be provided with suitable, optionally enteric, coatings. Dyes or pigments may be added to the tablets or tablet coatings, for example for identification purposes or to indicate different doses of active ingredient. Pharmaceutical compositions for oral administration also include hard capsules consisting of gelatin, and also soft, sealed capsules consisting of gelatin and a plasticizer, such as glycerol or sorbitol. The capsules may contain the active ingredient in the form of granules, or dissolved or suspended in suitable liquid excipients, such as in oils.

Transdermal application is also considered, for example using a transdermal patch, which allows administration over an extended period of time, e.g. from one to twenty days.

Methods of Use

The present invention provides a method of reducing airway constriction comprising administering an effective amount of a compound or composition of formulae (I) or (II), or a salt thereof. In some embodiments, compounds of formula (I) or (II) have reduced benzodiazepine-type CNS effects in a subject compared to diazepam at therapeutic doses. In some embodiments, airway constriction occurs during anesthesia.

The present invention further provides a method of reducing lung inflammation comprising administering an effective amount of a compound or composition of formula (I) or (II), or a pharmaceutically acceptable salt thereof to a subject in need thereof. In some embodiments, compounds of formula (I) or (II) have reduced benzodiazepine-type CNS effects in a subject compared to diazepam at therapeutic doses. In some embodiments, the lung inflammation is associated with asthma, chronic obstructive pulmonary disease, emphysema, cystic fibrosis, pulmonary fibrosis, bronchiectasis, fibrosing alveolitis, Wegener's granulomatosis, intrinsic alveolitis or infection. The infection is suitably caused by viral, bacterial and/or fungal agents.

Lung inflammation may be evidenced in a patient by impaired pulmonary function, shortness of breath, especially with exertion or exercise, coughing, or labored breathing. A wide variety of diagnostic tools, including chest x-rays, CT scans, and pulmonary function tests are used to diagnose inflammatory lung disease. Pulmonary function and exercise tests may be used to determine lung capacity impaired by inflammation. Tissue samples from the lungs can be obtained for more definite diagnosis of inflammation. This can be obtained with a bronchoscopy (transbronchial biopsy) or bronchoalveolar lavage or surgical lung biopsy. Histologically, inflammation may reveal increased numbers of macrophages, lymphocytes, or polymorphonuclear cells in sputum and bronchoalveolar lavage fluid or lung parenchema or airways. Migration and activation of immune/inflammatory cells to the lung is regulated by a variety of different mediators, including proteases, cytokines, and chemokines secreted by a variety of inflammatory and resident cells.

In another aspect, the present invention provides a method of reducing the development of disease in subjects having risk factors associated with lung inflammation comprising administering an effective amount of a compound or composition of formula (I) or (II), or a pharmaceutically acceptable salt thereof to a subject in need thereof. In some embodiments, compounds of formula (I) or (II) have reduced benzodiazepine-type CNS effects in a subject compared to diazepam at therapeutic doses.

A number of factors may increase the likelihood of developing inflammatory lung diseases: low birth weight, having a blood relative with a condition such as asthma (thus a genetic predisposition), the presence of specific gene mutations (such as in cystic fibrosis transmembrane conductor regulator (CFTR) genes), obesity, smoking or exposure to smoke (including in-utero exposure), exposure to exhaust fumes or other types of environmental pollution, or exposure industrial or agricultural chemicals.

In some embodiments, the lung inflammation is associated with asthma, chronic obstructive pulmonary disease, emphysema, cystic fibrosis, pulmonary fibrosis, bronchiectasis, fibrosing alveolitis, Wegener's granulomatosis, intrinsic alveolitis or infection. The infection is suitably caused by viral, bacterial and/or fungal agents.

The present invention further provides a method of reducing inflammation in a subject having an autoimmune disease comprising administering an effective amount of a compound or composition of formula (I) or (II), or a pharmaceutically acceptable salt thereof to a subject in need thereof. In some embodiments, compounds of formula (I) or (II) have reduced benzodiazepine-type CNS effects in a subject compared to diazepam at therapeutic doses. In some embodiments, the autoimmune disease is selected from arthritis, diabetes, lupus, and Crohn's disease.

The following non-limiting examples are intended to be purely illustrative of some aspects and embodiments, and show specific experiments that were carried out in accordance with the disclosure.

EXAMPLES

Example 1. Synthesis of (R)-8-ethynyl-6-(2-fluorophenyl)-4-methyl-4H-benzo[f]imidazo[1,5-a][1,4]diazepine-3-carboxylic acid (SH-053-2'F—R—CH3-Acid)

Compound 7 (2.0 g, 5.16 mmol) was stirred in ethanol (100 mL) and 3 M sodium hydroxide (20 mL, 60 mmol) was added and the solution was heated and refluxed for 1 hour. The reaction solution was then cooled to room temperature and diluted with water (100 mL). The solution was placed under reduced pressure until half of the solvent remained. The remaining reaction mixture was stirred at room temperature and hydrochloric acid (1 M) was added dropwise at room temperature until the product precipitated out. The product was filtered, rinsed with water and dried to afford pure acid SH-053-2'F—R—CH3-Acid as a white solid (81% yield): $^1$H NMR (300 MHz, DMSO-$d_6$) δ 8.42 (s, 1H), 7.94

(d, 1H, J=8.4 Hz), 7.82 (d, 1H, J=8.2 Hz), 7.56 (dt, 2H, J=7.8, 6.5 Hz), 7.33 (t, 1H, J=7.4 Hz), 7.22 (t, 2H, J=9.3 Hz), 6.53 (d, 1H, J=7.1 Hz), 2.51 (s, 1H), 1.16 (d, 3H, J=6.8 Hz); $^{13}$C NMR (75 MHz, DMSO-d$_6$) δ 164.76, 162.81, 158.19, 140.57, 136.57, 135.54, 134.74, 133.18, 132.65, 131.88, 129.88, 129.35, 125.17, 123.98, 121.09, 116.53, 116.25, 83.42, 82.01, 49.79, 15.08; HRMS (LCMS-IT-TOF) Calc. for $C_{21}H_{14}FN_3O_2$ (M+H)+ 360.1143, found 360.1140.

Example 2. Synthesis of (R)-8-Bromo-6-(2-fluorophenyl)-4-methyl-4H-benzo[f]imidazo[1,5-a][1,4]diazepine-3-carboxylic acid (GL-II-93)

Compound 4 (5.1 g, 11.5 mmol) was dissolved in EtOH (150 mL), after which solid NaOH (0.9 g, 23 mmol) was added to the solution. This reaction mixture was heated to 70° C. for 1 hour and the EtOH was removed under reduced pressure. The remaining aqueous solution was stirred at 0° C. for 10 minutes and then 10% aqueous HCl was added dropwise to the solution until the pH was 5 (pH paper). A pale white precipitate which formed, was left in the solution for 10 minutes and was then collected by filtration. The solid was washed with cold water and the aqueous layer also allowed to stand at room temperature for 10 hours to yield additional acid. The combined solids were dried in a vacuum oven at 80° C. for 7 hours to provide pure GL-II-93 as a white powder (4 g, 9.7 mmol, 85.2%): $^1$H NMR (500 MHz, CDCl$_3$): δ 8.12 (s, 1H), 7.73 (d, J=7.6 Hz, 1H), 7.63 (s, 1H), 7.55 (d, J=8.3 Hz, 1H), 7.50-7.37 (m, 2H), 7.25 (t, J=7.3 Hz, 1H), 7.07-6.99 (m, 1H), 6.78 (q, J=7.2 Hz, 1H), 1.27 (d, J=6.3 Hz, 3H); $^{13}$C NMR (126 MHz, CDCl$_3$): δ 164.94, 162.87, 161.09, 159.09, 141.28, 135.04, 134.91, 133.59, 133.08, 132.51, 132.12, 131.34, 131.11, 129.38, 128.16, 124.57, 123.91, 120.40, 116.30, 116.13, 49.83, 14.91; HRMS (LCMS-IT-TOF) Calc. for $C_{19}H_{13}N_3O_2FBr$ (M+H)+ 414.0248, found 414.0235.

Example 3. Synthesis of (R)-8-Cyclopropyl-6-(2-fluorophenyl)-4-methyl-4H-benzo [f]imidazo[1,5-a][1,4]diazepine-3-carboxylic acid (GL-III-43)

Compound 4 (2.1 g, 4.8 mmol) was dissolved in toluene (20 mL). The cyclopropylboronic acid (1.0 g, 12.0 mmol) and water (1.5 mL) were added to the mixture. A reflux condenser was attached and the mixture was degassed under vacuum with argon; this process was repeated four times. The bis(triphenylphosphine)-palladium (II) acetate (0.72 g, 0.96 mmol) and K$_3$PO$_4$ were added to the reaction mixture which was degassed with argon/vacuum for another four times. Then the reaction mixture was heated to reflux under argon and allowed to stir for 3 hours. The reaction mixture was quenched by addition of cold water and extracted with ethyl acetate. The organic layers were combined and washed with brine (2×150 mL), dried Na$_2$SO$_4$ and the solvent was removed under reduced pressure to afford a brown solid. The crude solid was purified by column chromatography (silica gel, ethyl acetate/hexanes 5:5) to provide pure compound 5 as an off-white solid (1.2 g, 3.0 mmol, 65%): $^1$H NMR (500 MHz, CDCl$_3$) δ 7.88 (s, 1H), 7.55 (t, J=7.1 Hz, 1H), 7.44 (d, J=8.3 Hz, 1H), 7.39 (dd, J=13.3, 5.8 Hz, 1H), 7.19 (dd, J=12.9, 6.1 Hz, 2H), 6.98 (dd, J=18.9, 9.9 Hz, 2H), 6.64 (q, J=7.2 Hz, 1H), 4.45-4.25 (m, 2H), 1.91-1.78 (m, 1H), 1.38 (t, J=7.1 Hz, 3H), 1.24 (d, J=7.3 Hz, 3H), 1.04-0.88 (m, 2H), 0.59 (m, 2H); $^{13}$C NMR (126 MHz, CDCl$_3$): δ 164.17, 163.12, 161.12, 159.12, 143.88, 141.58, 134.85, 132.09, 131.65, 131.21, 129.16, 129.04, 128.47, 127.87, 124.33, 121.95, 116.08, 115.91, 60.59, 50.05, 15.04, 14.64, 14.44, 9.91, 9.89; HRMS (LCMS-IT-TOF) Calc. for $C_{24}H_{22}N_3O_2F$ (M+H)+ 404.1769, found 404.1763.

GL-III-43 was prepared from compound 5 following the general procedure outlined for GL-II-93 in the previous procedure and obtained GL-III-43 as a white solid (0.62 g, 1.7 mmol, 75%): 1H NMR (500 MHz, DMSO-d$_6$) δ 8.34 (s, 1H), 7.77 (d, J=7.2 Hz, 1H), 7.58-7.49 (m, 2H), 7.32 (m, 2H), 7.21 (t, J=8.8 Hz, 1H), 6.94 (s, 1H), 6.50 (q, J=5.2 Hz, 1H), 1.93 (m, J=4.1 Hz, 1H), 1.13 (d, J=6.4 Hz, 3H), 0.95 (d, J=7.7 Hz, 2H), 0.61 (m, 2H); HRMS (LCMS-IT-TOF) Calc. for $C_{22}H_{18}N_3O_2F$ (M+H)+ 376.1456, found 376.1453.

Example 4. Synthesis of (R)-8-Chloro-6-(2-fluorophenyl)-4-methyl-4H-benzo[f]imidazo[1,5-a][1,4]diazepine-3-carboxylic acid (GL-III-54)

GL-III-54 was prepared from compound 8 following the general procedure reported above and obtained as a white solid (0.93 g, 2.5 mmol, 85%): $^1$H NMR (500 MHz, DMSO-d6) δ 8.41 (s, 1H), 7.97 (d, J=8.4 Hz, 1H), 7.84 (t, J=10.0 Hz, 1H), 7.65-7.52 (m, 2H), 7.34 (t, J=7.4 Hz, 1H), 7.27-7.14 (m, 2H), 6.56 (q, J=7.0 Hz, 1H), 1.17 (d, J=6.9 Hz, 3H); HRMS (LCMS-IT-TOF) Calc. for $C_{19}H_{13}N_3O_2FCl$ (M+H)+ 370.0753, found 370.0752.

Example 5. Synthesis of (R)-8-Bromo-4-methyl-6-(pyridin-2-yl)-4H-benzo[f]imidazo[1,5-a][1,4]diazepine-3-carboxylic acid (GL-II-51)

GL-II-51 was prepared from compound 9 following the general procedure reported above and obtained as a white solid (0.87 g, 2.2 mmol, 62%): $^1$H NMR (500 MHz, DMSO-d6) δ 8.51 (s, 1H), 8.38 (s, 1H), 8.01 (d, J=7.5 Hz, 1H), 7.98-7.89 (m, 2H), 7.84 (d, J=7.6 Hz, 1H), 7.47 (m, 2H), 6.54 (d, J=5.3 Hz, 1H), 1.17 (d, J=6.4 Hz, 3H); HRMS (LCMS-IT-TOF) Calc. for $C_{18}H_{13}N_4O_2Br$ (M+H)+ 397.0295, found 397.0299.

Example 6. Synthesis of (R)-8-Ethynyl-4-methyl-6-(pyridin-2-yl)-4H-benzo[f]imidazo[1,5-a][1,4]diazepine-3-carboxylic acid (GL-II-30)

GL-II-30 was prepared from compound 10 following the general procedure reported above and obtained as a white solid (1.06 g, 3.1 mmol, 60%): 1H NMR (500 MHz, DMSO-d6) δ 8.57 (d, J=3.8 Hz, 1H), 8.02 (dd, J=27.8, 13.9 Hz, 2H), 7.84 (t, J=6.6 Hz, 1H), 7.69 (d, J=8.0 Hz, 1H), 7.57 (d, J=8.2 Hz, 1H), 7.42 (s, 1H), 7.40-7.31 (m, 1H), 6.72 (q, J=7.0 Hz, 1H), 3.15 (s, 1H), 1.25 (d, J=7.0 Hz, 3H); HRMS (LCMS-IT-TOF) Calc. for $C_{20}H_{14}N_4O_2$ (M+H)+ 343.1190, found 343.1188.

Example 7. Synthesis of (S)-7-methoxy-1-(1H-tetrazol-5-yl)-11,12,13,13a-tetrahydro-9H-benzo[e]imidazo[5,1-c]pyrrolo[1,2-a][1,4]diazepin-9-one (RJ-03-57)

DIBAL-H (1.2 M, 6.2 mL, 7.4 mmol) was added at 0° C. to a solution of sodium tert-butoxide (0.76 g, 7.9 mmol) in 20 mL of dry tetrahydrofuran. The resulting mixture was stirred for 1 hour at room temperature under argon atmosphere. Compound 15 (1.5 g, 4.4 mmol) was then added to the above solution at 0° C. and stirred for 3 hours (or until the complete consumption of 15) at room temperature under argon atmosphere. After that, concentrated NH$_3$ (28%, 20 mL) and I$_2$ (4.57 g, 18.0 mmol) were added at 0° C. and the resulting mixture was stirred at room temperature for 3 hours. After complete disappearance of the aldehyde intermediate, the reaction mixture was treated with a saturated solution of sodium thiosulfate (~10 mL) and extracted with ethyl acetate (3×30 mL). The combined organic layers were washed with brine, dried over $Na_2SO_4$ and solvent was evaporated under reduced pressure. The residue was purified with silica gel flash column chromatography (70% ethyl acetate in hexanes) to furnish the nitrile 17 as white solid, 1.225 g, 95%. At this point, to a solution of the nitrile 17 (0.295 g, 1.0 mmol) in 30 mL of tetrahydrofuran, $ZnBr_2$ (0.34 g, 1.50 mmol) and $NaN_3$ (78 mg, 1.20 mmol) were added and the mixture was heated to reflux for 36 hours (or until the complete consumption of 17). The solution was treated with 1M HCl to dissolve the solid material and bring the pH of the solution to 1. The solution was extracted with ethyl acetate (4×40 mL). The solvent was evaporated under reduced pressure and the residue was passed through a short pad of silica with 7% methanol in dichloromethane to furnish 196 mg of RJ-03-57, 58%. $^1H$ NMR (300 MHz, DMSO-$d_6$): δ 1.96-2.14 (m, 2H), 2.23-2.40 (m, 1H), 3.40-3.50 (m, 1H), 3.5-3.66 (m, 1H), 3.89 (s, 3H), 3.96-4.10 (m, 1H), 4.95 (d, 1H, J=8.34 Hz), 7.31-7.38 (m, 1H), 7.43 (d, 1H, J=2.8 Hz), 7.69 (d, 1H, J=8.8 Hz), 8.60 (s, 1H); $^{13}C$ NMR (75 MHz, DMSO-$d_6$): δ 24.7, 27.9, 46.6, 52.3, 56.3, 115.1, 119.2, 123.5, 126.0, 126.5, 130.9, 137.7, 155.4, 159.3, 163.3; HRMS (ESI) (M−H), calcd for $C_{16}H_{16}N_7O_2$ 336.1360; found 336.1357.

Example 8. Synthesis of (S)—N,7-Dimethoxy-9-oxo-11,12,13,13a-tetrahydro-9H-benzo[e]imidazo[5,1-c]pyrrolo[1,2-a][1,4]diazepine-1-carboxamide (MRS-III-87)

A mixture of compound 16 (0.15 g), thionyl chloride (1 mL) and dry $CH_2Cl_2$ (8 mL) was added to an oven dried round bottomed flask under argon. This suspension was allowed to reflux at 52° C. (the outside oil bath temperature was at 60° C.) for 1 hour under an atmosphere of argon. The solution became a clear yellow color. The absence of the starting material was confirmed by the examination of the solution by thin-layer chromatography (TLC) (silica gel). The organic solvent and excess thionyl chloride were removed under reduced pressure. This flash evaporation with dry dichloromethane (5 mL) was repeated two times to remove excess thionyl chloride and any HCl. The yellow residue, which was obtained, was dissolved in dry $CH_2Cl_2$ (10 mL) and cooled to 0° C. for 10 minutes under argon. Then methyl hydroxylamine hydrochloride (2.5 equivalents), followed by triethylamine (5 equivalents) was added to the reaction mixture at 0° C. and the mixture was then allowed to warm to room temperature and stirred for 4 hours. After the completion of the reaction (TLC, silica gel), the solvent was removed under reduced pressure and acetone (4 mL) was added to the residue. The salt was removed by filtration and the solvent was removed under reduced pressure to provide MRS-II-87 in 70% yield: $^1H$ NMR (300 MHz, CDCl$_3$) δ 2.14-2.22 (m, 2H), 2.30-2.39 (m, 1H), 3.08-3.10 (m, 1H), 3.51-3.57 (m, 1H), 3.75-3.80 (m, 1H), 3.88 (s, 3H), 3.91 (s, 3H), 4.72 (d, 1H, J=8.8 Hz), 7.28 (d, 1H, J=8.8 Hz), 7.58 (d, 1H, J=2.7 Hz), 7.69 (s, 1H), 9.84 (bs, 1H); LCMS (ESI, m/z, relative intensity (ESI), calcd. for $C_{17}H_{17}N_4O_4$ (M−H)+ 341.35; Found 341.00.

Example 9. Synthesis of (S)—N-Cyano-7-methoxy-9-oxo-11,12,13,13a-tetrahydro-9H-benzo[e]imidazo[5,1-c]pyrrolo[1,2-a][1,4]diazepine-1-carboxamide (MRS-III-90)

A mixture of compound 16 (0.15 g), thionyl chloride (1 mL) and dry $CH_2Cl_2$ (8 mL) were added to an oven dried round bottomed flask under argon. This suspension was allowed to reflux at 52° C. (the outside oil bath temperature was at 60° C.) for 1 hour under an atmosphere of argon. The solution became a clear yellow color. The absence of the starting material was confirmed by the examination of the solution by TLC (silica gel). The organic solvent and excess thionyl chloride were removed under reduced pressure. This evaporation was repeated a couple of times with dry $CH_2Cl_2$ (5 mL) to remove excess thionyl chloride and any HCl. The yellow residue, which was obtained, was dissolved in dry $CH_2Cl_2$ (10 mL) and cooled to 0° C. for 10 minutes under argon. The methyl cyanamide (2.5 equivalents), followed by triethylamine (5 equivalents) were added to the reaction mixture at 0° C. and the mixture was then allowed to warm to room temperature and stirred for 5 hours. After the completion of the reaction (TLC, silica gel), the solvent was removed under reduced pressure and acetone (4 mL) was added to the residue. The salt was filtered off and the solvent was removed under reduced pressure to obtain MRS-III-90 in 70% yield. $^1H$ NMR (300 MHz, DMSO-d6) δ 2.10-2.13 (m, 2H), 3.34-3.58 (m, 3H), 3.88 (s, 3H), 3.91 (s, 3H), 4.73 (d, 1H, J=7.5 Hz, major rotamer 83%), 4.84 (d, J=7.5 Hz, minor rotamer, 17%), 7.27-7.29 (m, 1H, major rotamer), 7.31-7.33 (m, minor rotamer), 7.38 (d, 1H, J=2.0 Hz, major rotamer), 7.41 (d, J=2.5 Hz, minor rotamer), 7.57 (d, 1H, J=8.5 Hz, major rotamer), 7.64 (d, J=9.0 Hz, minor rotamer), 8.00 (s, 1H, major rotamer), 8.21 (s, minor rotamer), 9.49-10.11 (bs, 1H); LCMS (ESI, m/z, relative intensity (ESI), calcd. for $C_{17}H_{14}N_5O_3$ (M−H)+ 336.33; Found 336.00.

Example 10. Synthesis of (S)-Ethyl-7-hydroxy-9-oxo-11,12,13,13a-tetrahydro-9H-benzo[e]imidazo[5,1-c]pyrrolo[1,2-a][1,4]diazepine-1-carboxylate (RJ-02-50)

In an oven dried round bottom flask, dry $CH_2Cl_2$ (50 ml) was added and cooled to 0° C. Then $AlCl_3$ (3 g, 22.8 mmol) and ethanethiol (4.5 ml, 60.8 mmol) were added to the above flask slowly at 0° C. The ice bath was removed and the reaction was allowed to warm up to room temperature. After the $AlCl_3$ dissolved completely, ester 15 (2.6 g, 7.62 mmol) was added to the mixture at room temperature and it was stirred for 24-36 hours under Ar. After completion of the reaction (TLC, silica gel), the solution was poured onto ice and was acidified using an aq 2N HCl solution. The solution was extracted 5-7 times with $CH_2Cl_2$ and 3-4 times with ethyl acetate separately. The combined organic layer was washed with brine and dried ($Na_2SO_4$). The solvent was removed under reduced pressure and the residue was purified by flash column chromatography on [silica gel, 4% methanol in $CH_2Cl_2$] to furnish RJ-02-50 as a solid (2.1 g) in 84% yield: M.p=>260° C. (decomp.); $^1H$ NMR (300 MHz, CDCl$_3$) δ 1.44 (t, 3H, J=7.1 Hz), 2.19-2.42 (m, 3H), 3.55-3.64 (m, 2H), 3.81-3.89 (m, 1H), 4.42 (q, 2H, J=7.1 Hz), 4.82 (d, 1H, J=7.3 Hz), 7.13 (dd, 1H, J=8.7 Hz, 2.6 Hz), 7.27-7.31 (m, 1H), 7.85 (s, 1H), 7.91 (d, 1H, J=2.6 Hz), 9.22 (s, 1H); $^{13}C$ NMR (75 MHz, CDCl$_3$) δ 14.3, 24.4, 28.4, 46.9, 53.8, 61.2, 117.5, 120.8, 124.9, 125.2, 127.7, 129.5, 136.0, 137.2, 157.6, 162.8, 164.6; HRMS (ESI) (M+H)+, calcd. for $C_{17}H_{18}N_3O_4$ 328.1292; Found 328.1293.

Example 11. Synthesis of (S)-7-hydroxy-9-oxo-11,12,13,13a-tetrahydro-9H-benzo[e]imidazo[5,1-c]pyrrolo[1,2-a][1,4]diazepine-1-carboxylic acid (RJ-03-90)

RJ-02-50 (1.52 g, 4.6 mmol) was dissolved in a mixture of ethanol (4 mL) and $H_2O$ (3 mL) after which solid NaOH (1.0 g, 25.0 mmol) was added to the solution. This reaction mixture was heated to 50° C. for 15 minutes and the ethanol was removed under reduced pressure. The remaining aqueous solution was stirred at 0° C. for 10 minutes and then concentrated HCl was added dropwise to the solution until the pH was 3-4 (pH paper). A pale yellow precipitate which formed was left in the solution and the mixture was allowed to stir at room temperature for 2 hours. The precipitate was collected by filtration, washed with cold water (2-5 mL) and the aqueous layer also was allowed to stand at room temperature for 10 hours to obtain additional RJ-03-90. The combined solids were dried in a vacuum oven at 80° C. for 7 hours to get pure RJ-03-90 in 65% yield $^1$H NMR (300 MHz, CD$_3$OD): δ 2.14-2.29 (m, 3H), 3.50-3.63 (m, 2H), 3.70-3.78 (m, 1H), 4.95 (d, 1H, merged with solvent peak), 7.15 (d, 1H, J=8.7 Hz, 3.0 Hz), 7.38-7.43 (m, 1H), 7.53 (d, 1H, J=8.76 Hz), 8.48 (m, 1H); $^{13}$C NMR (75 MHz, CD$_3$OD) δ 24.0, 27.7, 46.2, 53.4, 116.2, 119.8, 124.5, 125.4, 128.4, 130.2, 136.2, 137.5, 158.2, 162.5, 164.4; HRMS (ESI) (M+H)+, calcd. for C$_{15}$H$_{14}$N$_3$O$_4$ 300.0979; Found 300.0990.

Example 12. Synthesis of (S)-tert-Butyl-7-hydroxy-9-oxo-11,12,13,13a-tetrahydro-9H-benzo[e]imidazo[5,1-c]pyrrolo[1,2-a][1,4]diazepine-1-carboxylate (RJ-02-67)

A flame dried round bottom flask was charged with dry tetrahydrofuran (30 mL) and lithium rod (excess, cut into small pieces) was added. Dry tert-butanol (2.6 mL, 27.1 mmol) was added to the above flask at room temperature and the mixture which resulted was heated to 45-50° C. under Ar until the tert-butanol reacted completely. This freshly prepared lithium tert-butoxide solution was transferred carefully with a cannula to another flame dried round bottom flask charged with RJ-02-50 (1.0 g, 2.71 mmol) and stirred at 50° C. under Ar for 30 minutes. After the completion of the reaction (TLC, silica gel), the flask was cooled to room temperature and the tetrahydrofuran removed under reduced pressure. Ice water (10 mL) was added to the residue and it was then extracted with ethyl acetate. The organic layer was washed with water (2×10 mL) and brine (15 mL). The solvent was removed under reduced pressure and the residue was purified by flash column chromatography [silica gel, ethyl acetate/hexane (7:3)] to yield RJ-02-67 as a solid (0.72 g) in 65% yield. M.p=174-175° C.; $^1$H NMR (300 MHz, CDCl$_3$) δ 1.63 (s, 9H), 2.09-2.34 (m, 3H), 3.50-3.62 (m, 2H), 3.77-3.85 (m, 1H), 4.79 (d, 1H, J=7.1 Hz), 7.10 (dd, 1H, J=8.6 Hz, 2.2 Hz), 7.23-7.28 (m, 1H), 7.77 (bs, 1H), 7.85 (s, 1H), 9.75 (bs, 1H); $^{13}$C NMR (75 MHz, CDCl$_3$) δ 24.4, 28.2, 28.3, 46.9, 53.7, 82.0, 117.4, 120.7, 124.9, 125.1, 129.1, 129.6, 135.8, 136.2, 157.7, 162.3, 164.6; HRMS (ESI) (M+H)+, calcd. for C$_{19}$H$_{22}$N$_3$O$_4$ 356.1605; Found 356.1615.

Example 13. Synthesis of (S)-7-hydroxy-1-(oxazol-5-yl)-11,12,13,13a-tetrahydro-9H-benzo[e]imidazo[5,1-c]pyrrolo[1,2-a][1,4]diazepin-9-one (RJ-03-30)

DIBAL-H (1M, 20.4 mL, 20.4 mmol) was added at 0° C. to a solution of sodium tert-butoxide (2.02 g, 21.02 mmol) in 30 mL of dry tetrahydrofuran. The resulting mixture was stirred for 1 hour at room temperature under argon atmosphere. Compound 15 (4 g, 11.72 mmol) was then added to the above solution at 0° C. and stirred for 3 hours (or until the complete consumption of 15) at room temperature under argon atmosphere. After completion of the reaction, excess DIBAL-H was quenched by careful addition of methanol (~15 mL), followed by 5% aqueous HCl (20-30 mL) at 0° C. After this the resulting mixture was allowed to warm to room temperature. The aqueous layer was extracted with CH$_2$Cl$_2$ (2×50 mL). The combined organic layers were washed with brine and dried (Na$_2$SO$_4$). The solvent was removed under reduced pressure to afford the crude aldehyde. This residue was purified by flash chromatography (2:1 ethyl acetate/hexane) to afford the pure diazepine aldehyde 18 as a white solid, (3.325 g, 93%).

Toluenesulfonylmethyl isocyanide, TosMIC (3.28 g, 16.8 mmol) was placed in a dry two neck round bottom flask and dissolved in dry methanol (40 mL) under an argon atmosphere. At room temperature, K$_2$CO$_3$ (4.64 g, 33.57 mmol) was added as well as aldehyde 18 (3.325 g, 11.18 mmol) to the reaction mixture, which was heated to reflux for 3 hours. After completion of the reaction as indicated by TLC (silica gel ethyl acetate), the reaction mixture was quenched with cold water. After this, ⅓ of the solvent was removed under reduced pressure and extracted with ethyl acetate (3×20 mL). The combined organic layers were washed with water and brine successively and dried (Na$_2$SO$_4$). The solvent was then removed under reduced pressure and the residue was purified by silica gel flash chromatography to give the pure oxazole 19 as white solid (2.83 g, 75%).

In an oven dried round bottom flask, dry CH$_2$Cl$_2$ (50 mL) was taken and cooled to 0° C. Then AlCl$_3$ (3.33 g, 24.97 mmol) and ethanethiol (5.0 ml, 67.52 mmol) were added to the above flask slowly at 0° C. The ice bath was removed and the reaction was allowed to warm up to room temperature. After AlCl$_3$ dissolved completely, 19 (2.8 g, 8.32 mmol) was added to the mixture at room temperature and stirred for 24-36 hours under Ar. After completion of the reaction (TLC, silica gel), the solution was poured to ice and was acidified using 2N HCl solution. The solution was extracted 5-7 times with CH$_2$Cl$_2$ and 3-4 times with ethyl acetate separately. The combined organic layers were washed with brine and dried over Na$_2$SO$_4$. The solvent was removed under reduced pressure and the residue was purified by flash column chromatography on [silica gel, 4% methanol in CH$_2$Cl$_2$] to furnish RJ-03-30 as a solid (2.36 g) in 88% yield. $^1$H NMR (500 MHz, CDCl$_3$): δ 1.97-2.08 (m, 2H), 2.25-2.35 (m, 1H), 2.65-2.73 (m, 1H), 3.63-3.71 (m, 1H), 3.76-3.84 (m, 1H), 4.84-4.88 (m, 1H), 7.10 (dd, 1H, J=8.6, 2.2 Hz), 7.30 (d, 1H, J=5.3 Hz), 7.40 (s, 1H), 7.75 (d, 1H, J=1.9 Hz), 7.95 (s, 1H), 8.02 (s, 1H), 9.85 (s, 1H); $^{13}$C NMR (125 MHz, CDCl$_3$): δ 23.9, 27.8, 47.2, 52.8, 117.6, 120.8, 123.5, 124.7, 125.3, 126.2, 129.3, 131.9, 136.5, 145.4, 150.9, 157.5, 164.8; HRMS (ESI) (M+H)+, calcd. for C$_{17}$H$_{15}$N$_4$O$_3$ 323.1139; Found 323.1130.

Example 14. Determination of GABA$_A$R Subtypes Selectivity

Compounds having selective activity bias for α4 and α5-GABA$_A$R can be identified. Patch clamp assays are used to quantify chloride flux induced inward currents resulting from agonism of GABA$_A$R containing single α-subunits. These results can demonstrate the ability to finely discriminate functional activity of GABA$_A$R receptor-ligand interactions. For electrophysiological experiments with *Xenopus* oocytes (Ramerstorfer et al. *European journal of pharmacology* 2010, 636, 8-27) mature female *Xenopus laevis* (Nasco, Fort Atkinson, WI, USA) were anaesthetized in a bath of ice-cold 0.17% Tricain (Ethyl-m-aminobenzoate) before decapitation and transfer of the frog's ovary to ND96 medium (96 mM NaCl, 2 mM KCl, 1 mM MgCl2, 5 mM HEPES; pH 7.5). Following incubation in 1 mg/ml collagenase (Sigma-Aldrich, St. Louis, MO, USA) for 30 minutes, stage 5 to 6 oocytes were singled out of the ovary and defolliculated using a platinum wire loop. Oocytes were stored and incubated at 18° C. in NDE medium (96 mM NaCl, 2 mM KCl, 1 mM MgCl2, 5 mM HEPES, 1.8 mM CaCl2); pH 7.5) that was supplemented with 100 U·mL-1 penicillin, 100 μg·mL-1 streptomycin and 2.5 mM pyruvate. Oocytes were injected with an aqueous solution of mRNA. A total of 2.5 ng of mRNA per oocyte was injected. Subunit ratio was 1:1:5 for αxβ3γ2 (x=1, 2, 3, 5) and 3:1:5 for α4β3γ2 receptors. Injected oocytes were incubated for at least 36 hours before electrophysiological recordings. Oocytes were placed on a nylon-grid in a bath of NDE medium. For current measurements, the oocytes were impaled with two microelectrodes (2-3 MΩ), which were filled with 2M KCl. The oocytes were constantly washed by a flow of 6 mL·min-1 NDE that could be switched to NDE containing GABA and/or drugs. Drugs were diluted into NDE from dimethylsulfoxide (DMSO) solutions resulting in a final concentration of 0.1% DMSO. Maximum currents measured in mRNA injected oocytes were in the microampere range for all receptor subtypes. To test for modulation of GABA induced currents by compounds, a GABA concentration that was titrated to trigger 3-5% of the respective maximum GABA-elicited current of the individual oocyte (EC3-5) was applied to the cell together with various concentrations of tested compounds. All recordings were performed at room temperature at a holding potential of −60 mV using a Warner OC-725C TEV (Warner Instrument, Hamden, CT, USA) or a Dagan CA-1B Oocyte Clamp or a Dagan TEV-200A TEV (Dagan Corporation, Minneapolis, MN, USA). Data were digitized using a Digidata 1322A or 1550 data acquisition system (Axon Instruments, Union City, CA, USA), recorded using Clampex 10.5 software (Molecular Devices, Sunnyvale, CA, USA), and analyzed using Clampfit 10.5 and GraphPad Prism 6.0 (La Jolla, CA, USA) software. Concentration-response data were fitted using the Hill equation. Data are given as mean±SEM from at least three oocytes of two batches. Alternatively, compound selectivity for α4 and α5-$GABA_AR$ can be identified by automated patch clamp assay. Therefore, Patch clamp assay: HEK293T stably expressing α1β3γ2 GABAAR or α4β3γ2 were maintained RPMI 1640 medium with L-glutamine supplemented with 10% (v/v) fetal bovine serum and 1% penicillin/streptomycin (Forkuo et al., Molecular Pharmaceutics 2016, 13, 2026-38). Briefly, the IonFlux plate layout consists of units of 12 wells: two wells contain intracellular solution (ICS containing 140 mM CsCl, 1 mM $CaCl_2$), 1 mM $MgCl_2$, 11 mM EGTA, 10 mM HEPES, pH 7.2 with CsOH), one contains cells diluted in extracellular solution (ECS containing 140 mM NaCl, 5.4 mM KCl, 1 mM $CaCl_2$), 10 mM D-glucose monohydrate, and 10 mM HEPES, pH 7.4 with NaOH), eight contain different concentration of 1 in the presence of GABA ($EC_{20}$ concentration) at 0.1% DMSO. Well 1 is for waste collection. Cells are captured from suspension by applying suction to microscopic channels in ensemble recording arrays. Once the array is fully occupied, the applied suction breaks the membranes of captured cells, which establishes whole cell voltage clamp. For compound applications, pressure is applied to the appropriate compound wells, which introduces the compound into the extracellular solution rapidly flowing over the cells. For recording $GABA_AR$ induced currents, cell arrays were voltage clamped at a hyperpolarizing holding potential of −80 mV. Prior to use on the automated patch clamp, cells were centrifuged at 380 g for 5 minutes and resuspended gently in ECS. This was repeated two more times before the cells were dispensed into the plate. All compound application were carried out for 3 seconds followed by a 5 second washout.

Figure 1B:
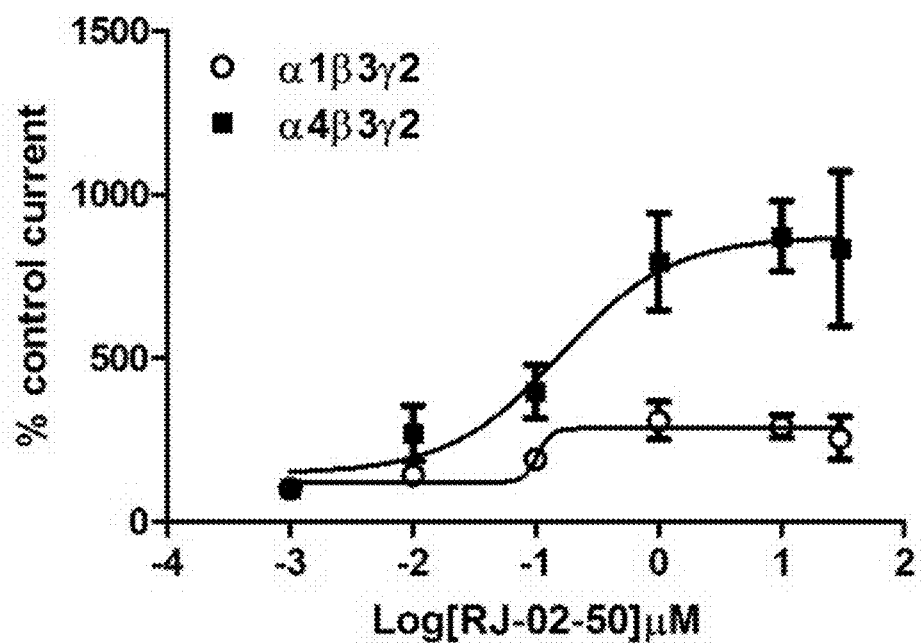
FIG. 1B shows automated patch clamp with RJ-02-50 using $\alpha1\beta3\gamma2$ or $\alpha4\beta3\gamma2 GABA_A$ receptor expressing HEK293T cells.

FIGS. 1A and 1B show $GABA_A$ receptor subtype selectivity. In FIG. 1A, dose dependent modulation of GABA (EC3-5 concentration) elicited currents by SH-053-2'F—R—$CH_3$-Acid on Xenopus oocytes expressing $GABA_A$ receptor subtypes α1β3γ2, α2β3γ2, α3β3γ2, α4β3γ2 and α5β3γ2. Data points represent means±SEM from 2-8 oocytes from 2 batches, normalized to control currents (100%) in the absence of compound. SH-053-2'F—R—$CH_3$-Acid is a positive α5β3γ2-selective $GABA_A$ receptor modulator. FIG. 1B shows automated patch clamp with RJ-02-50. Concentration-dependent negative current responses in the presence of $EC_{20}$ concentration of GABA and increasing concentration of compound 1 applied together for 3 seconds using α1β3γ2 or α4β3γ2GABAAR expressing HEK293T cells. Negative current readings were normalized to $EC_{20}$ concentration of GABA response set as 100% (n=16). RJ-02-50 is a positive α4β3γ2-selective $GABA_A$ receptor modulator.

Example 15. Determination of Cytotoxicity of Compounds

Compounds with increased cytotoxicity can be identified using an in vitro cytotoxicity assay. Therefore, human embryonic kidney 293T (HEK293T) cell lines were purchased (ATCC) and cultured in 75 cm2 flasks (CellStar). Cells were grown in DMEM/High Glucose (Hyclone, #SH3024301) media to which non-essential amino acids (Hyclone, #SH30238.01), 10 mM HEPES (Hyclone, #SH302237.01), 5×106 units of penicillin and streptomycin (Hyclone, #SV30010), and 10% of heat inactivated fetal bovine serum (Gibco, #10082147) were added. Cells were harvested using 0.05% Trypsin (Hyclone, #SH3023601). The cell viability assay was evaluated using CellTiter-Glo™ Luminescent Cell Viability Assay Kit (Promega, Madison, WI), which contains luciferase and all its substrate except ATP. The controls for the cytotoxicity assay used were (E)-10-(bromotriphenylphosphoranyl)decyl 4-(4-(tert-butyl)phenyl)-4-oxobut-2-enoate (400 μM in DMSO, positive control) and DMSO (negative control). All luminescence readings were performed on a Tecan Infinite M1000 plate reader. Small volume transfers were performed on the Tecan Freedom EVO liquid handling system with a 100 nL pin tool transfer (V&P Scientific). Serial dilutions were done in 96-well polypropylene plates (Corning, #3365) and assays were conducted in 384-well white optical bottom plates. The assays were carried out in quadruplet in three independent runs. The data were normalized to the controls and if possible analyzed by nonlinear regression (GraphPad Prism).

TABLE 1

Cytotoxicity of compounds determined in the presence of human kidney and liver cells. None of the investigated compounds induced cytotoxicity up to a concentration of 100 μM. For the majority of compounds, no toxicity was observed at a concentration of 400 μM

| Compound | $LD_{50}$ HEK293 (μM) (Kidney) | $LD_{50}$ HEPG2 (μM) (Liver) |
|---|---|---|
| RJ-03-57 | >200 | >200 |
| SH-053-2'F-R-$CH_3$-acid | >400 | >400 |
| GL-II-93 | >400 | >400 |

TABLE 1-continued

Cytotoxicity of compounds determined in the presence of human kidney and liver cells. None of the investigated compounds induced cytotoxicity up to a concentration of 100 µM. For the majority of compounds, no toxicity was observed at a concentration of 400 µM

| Compound | $LD_{50}$ HEK293 (µM) (Kidney) | $LD_{50}$ HEPG2 (µM) (Liver) |
| --- | --- | --- |
| RJ-02-50 | >400 | >400 |
| RJ-02-67 | >400 | >400 |
| RJ-03-30 | >400 | >400 |

Example 16. Rotarod Assay, to Determine Induced CNS Effects by Compounds

Figure 2:
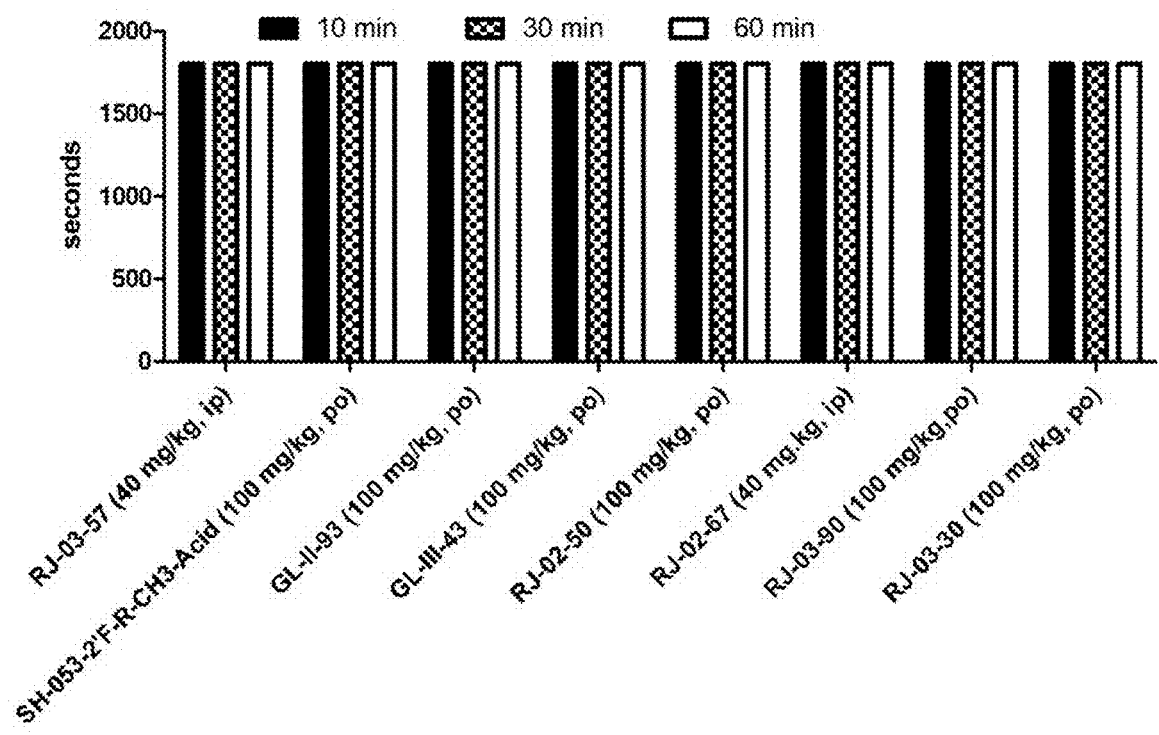
FIG. 2 shows the effect of compounds on sensorimotor coordination in a rotarod test.

Compounds with the ability to cross the blood brain barrier and induce CNS effects modulating the sensorimotor skills of mice can be identified with the rotarod. Female Swiss Webster mice were trained to maintain balance at a constant speed of 15 rpm on the rotarod apparatus (Omnitech Electronics Inc., Nova Scotia, Canada) until mice could perform for three minutes at three consecutive time points. Separate groups of mice received intraperitoneal (i.p.) injections of compounds in vehicle (10% DMSO, 40% propylene glycol and 50% PBS) or oral gavage (p.o.) in vehicle (2% hydroxypropyl methylcellulose and 2.5% polyethylene glycol) in an approximate volume of 100 µl. Ten, thirty, and sixty minutes after each injection, mice were placed on the rotarod for three minutes. In case that mice fell from the rotarod prior to 3 minutes the time was noted and averaged for the group of mice. An unpaired t-test (GraphPad Prism) was used to determine significance for *p<0.05, p<0.01, and *p<0.001. FIG. 2 shows the effect of compounds on sensorimotor coordination. Swiss Webster mice were tested on a rotarod at 15 rpm for 3 minutes at 10, 30, and 60 min following compound exposure. Mice (N=10) received a single injection (i.p. or p.o.) of test compound. The time of fall was recorded if it occurred prior to 3 minutes. Data are expressed as mean±SEM (N=10). Student's t-test was used to calculate significance: * (p<0.05),  (p<0.01) or * (p<0.001) significance compared to vehicle-treated mice. None of the investigated compounds induced any sensorimotor impairments at the concentration tested.

Example 17. Microsomal Stability of Compounds

The metabolic stability of compounds in vivo can be estimated with the stability of compounds in the presence of liver microsomes. Therefore, 4 µL of 1 mM DMSO solution of test compound at a final concentration of 10 µM were preincubated at 37° C. for 5 minutes on a digital heating shaking dry bath (Fischer scientific, Pittsburgh, PA) in a mixture containing 282 µL of water, 80 µL of phosphate buffer (0.5 M, pH 7.4) 20 µL of NADPH Regenerating System Solution A (BD Bioscience, San Jose, CA) and 4 µL of NADPH Regenerating System Solution B (BD Bioscience, San Jose, CA) in a total volume of 391.2 µL. Following preincubation, the reaction was initiated by addition of 8.8 µL of either human liver microsomes (BD Gentest, San Jose, CA) or mouse liver microsomes (Life technologies, Rockford, IL) at a protein concentration of 0.5 mg/mL. Aliquots of 50 µL were taken at time intervals of 0 (without microsomes), 10, 20, 30, 40, 50 and 60 minutes. Each aliquot was added to 100 µL of cold acetonitrile solution containing 1 µM of verapamil HCL as internal standard. This was followed by sonication for 10 seconds and centrifugation at 10,000 rpm for 5 minutes. 100 µL of the supernatant was transferred into Spin-X HPLC filter tubes (Corning Incorporated, NY) and centrifuged at 13,000 rpm for 5 minutes. The filtrate was diluted 100-fold and subsequently analyzed by LC-MS/MS with Shimadzu LCMS 8040, (Shimadzu Scientific Instruments, Columbia, MD). The ratio of the peak areas of the internal standard and test compound was calculated for every time point and the natural log of the ratio were plotted against time to determine the linear slope (k). The metabolic rate (k*C0/C), half-life (0.693/k), and internal clearance (V*k) were calculated, where k is the slope, C0 is the initial concentration of test compound, C is the concentration of microsomes, and V is the volume of incubation in µL per microsomal protein in mg. All experiments were repeated two time in triplicates.

TABLE 2

Microsomal stability of compounds was tested with human and mouse liver microsomes. The majority of compounds exhibited a similar stability in the presence of human and mouse liver microsomes except compound RJ-02-67. More than 90% of all other compounds was observed after 60 minutes, when incubated with human and mouse liver microsomes.

| Compound | HLM % remaining after 60 min | MLM % remaining after 60 min |
| --- | --- | --- |
| RJ-03-57 | 94.3 ± 0.1 | 98.3 ± 0.2 |
| SH-053-2'F-R-CH$_3$-Acid | 92.0 ± 0.2 | 89.0 ± 0.3 |
| RJ-02-50 | 91.7 ± 0.2 | 91.1 ± 0.1 |
| RJ-02-67 | 90.6 ± 0.2 | 46.6 ± 0.3 |
| RJ-03-30 | 91.8 ± 0.2 | 80.0 ± 0.3 |

Example 18. Relaxation of Guinea Pig Airway Smooth Muscle by Compounds

Figure 3A:
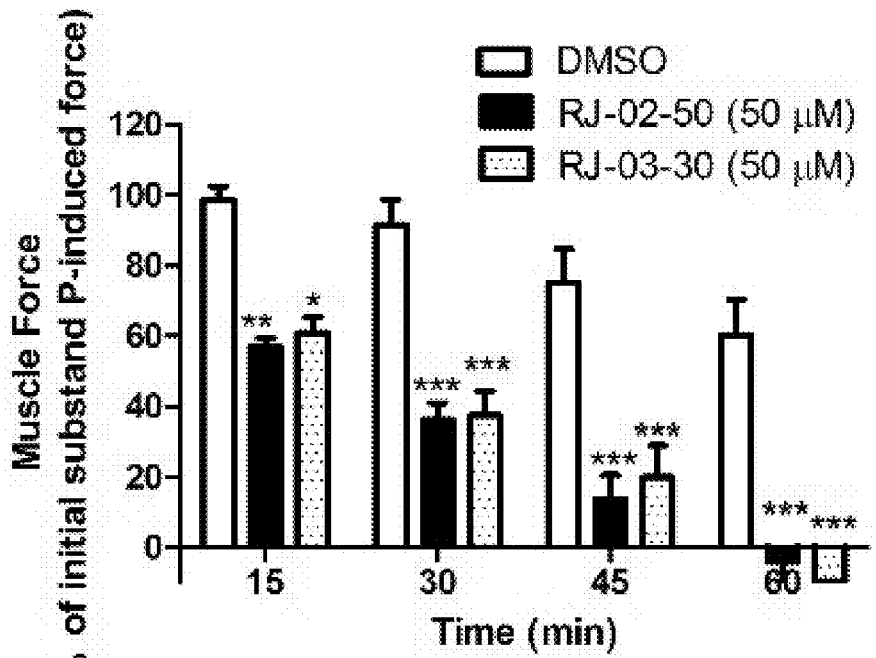
FIG. 3A shows effects on airway smooth muscle contractile force in guinea pig tracheal rings for RJ-02-50 and RJ-03-30.
Figure 3B:
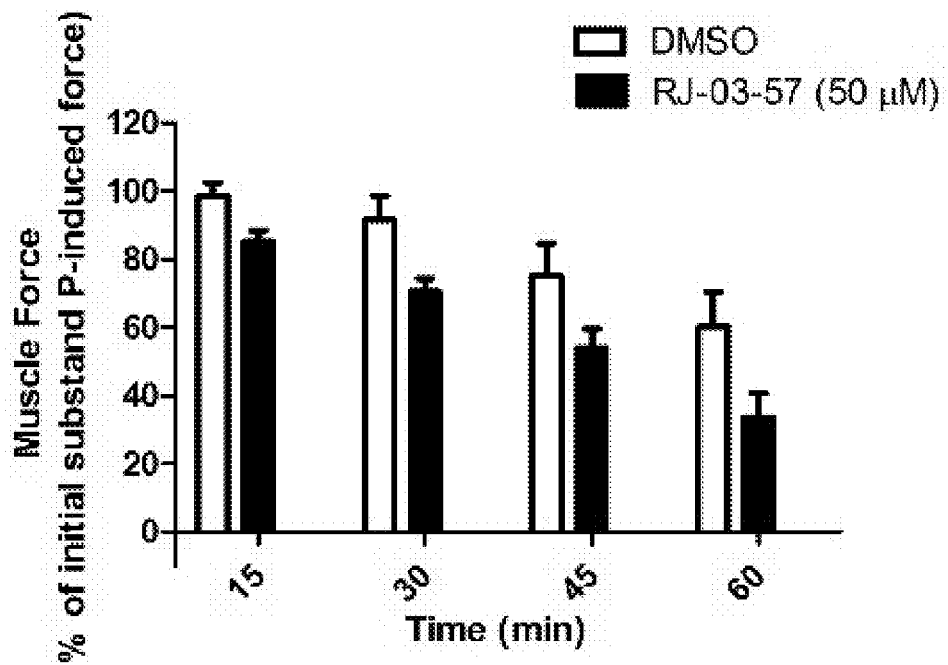
FIG. 3B shows effects on airway smooth muscle contractile force in guinea pig tracheal rings for RJ-03-57.
Figure 3C:
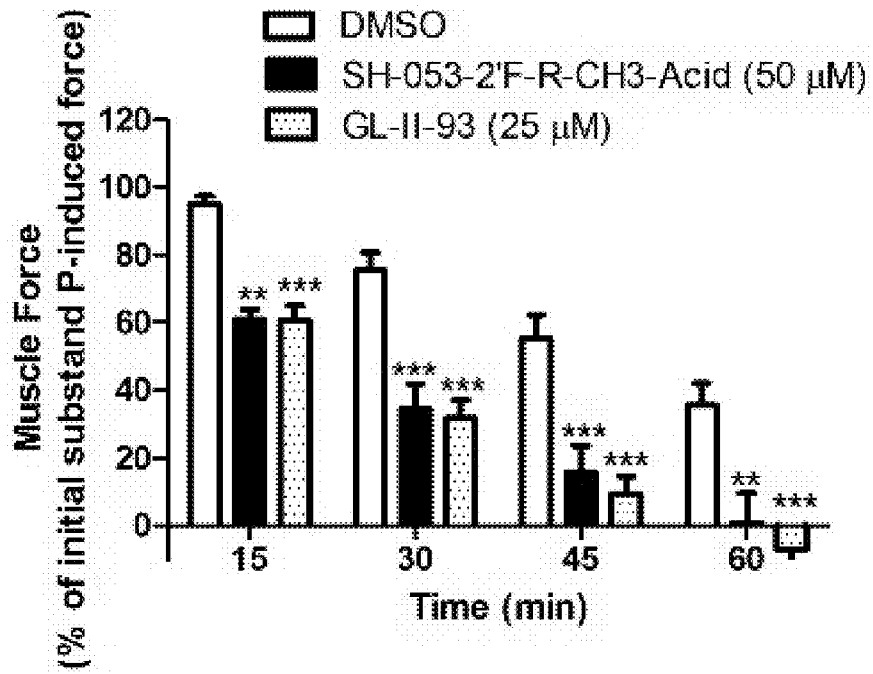
FIG. 3C shows effects on airway smooth muscle contractile force in guinea pig tracheal rings for SH-053-2'F—R—CH3 Acid and GL-II-93.

All studies were conducted after approval of the Columbia University IACUC. Adult male Hartley guinea pigs were euthanized by intraperitoneal pentobarbital (100 mg/kg). The tracheas were surgically removed and transected into cross-sections containing two cartilaginous rings. The rings are washed for one hour with at least five buffer exchanges to remove any pentobarbital. After the epithelium was removed with a cotton swab, the rings were suspended from two silk threads in a 4 mL jacketed organ bath (Radnoti Glass Technology), with one thread attached to a Grass FT03 force transducer (Grass-Telefactor) coupled to a computer via Biopac hardware and Acknowledge 7.3.3 software (Biopac Systems) for continuous digital recording of muscle tension. The rings were bathed in 4 ml of KH buffer solution (composition in mM: 118 NaCl, 5.6 KCl, 0.5 CaCl$_2$), 0.2 MgSO$_4$, 25 NaHCO$_3$, 1.3 NaH$_2$PO$_4$, 5.6 D-glucose) with 10 µM indomethacin (DMSO vehicle final concentration of 0.01%), which was continuously bubbled with 95% O2 and 5% CO$_2$ at pH 7.4, 37° C. The rings were equilibrated at 1 g of isotonic tension for 1 hour with new KH buffer added every 15 minutes. All rings were precontracted with 10 µM N-vanillylnonanamide (capsaicin analog) and then two cycles of cumulatively increasing concentrations of acetylcholine (0.1-100 µM) with extensive buffer washes between and after those two cycles with resetting of the resting tension to 1.0 g. Tetrodotoxin (1 µM) and pyrilamine (10 µM) were added to the buffer in the baths to eliminate the confounding effects of airway nerves and histamine receptors. After a stable baseline at 1.0 g resting tension was established, tracheal rings were contracted with 1 µM of substance P. After the peak contraction was reached, indicated concentrations of compounds or vehicle (0.1% DMSO) was added to the bath. The percentage of initial contraction remaining at indicated time points after compound exposure was expressed as a percentage of the remaining contractile force in vehicle-treated tissues and compared between groups. FIGS. 3A-3C show airway smooth muscle contractile force in guinea pig tracheal rings. Tracheal rings were contracted with 1 mM substance P and then treated with 50 mM of compounds or vehicle control (0.1% DMSO). The percent of remaining contractile force was measured at various time points and expressed as a percent of the initial substance P induced contractile force. (N>6) A 2way ANOVA was used to calculate significance with *(p<0.05), (p<0.01) or *(p<0.001) p-values are given for each condition. All investigated compounds except RJ-03-57 reduced the constriction of airway smooth muscle after 15 minutes for a period of at least 60 minutes.

Example 19. Relaxation of Human Airway Smooth Muscle by Compounds

Figure 4:
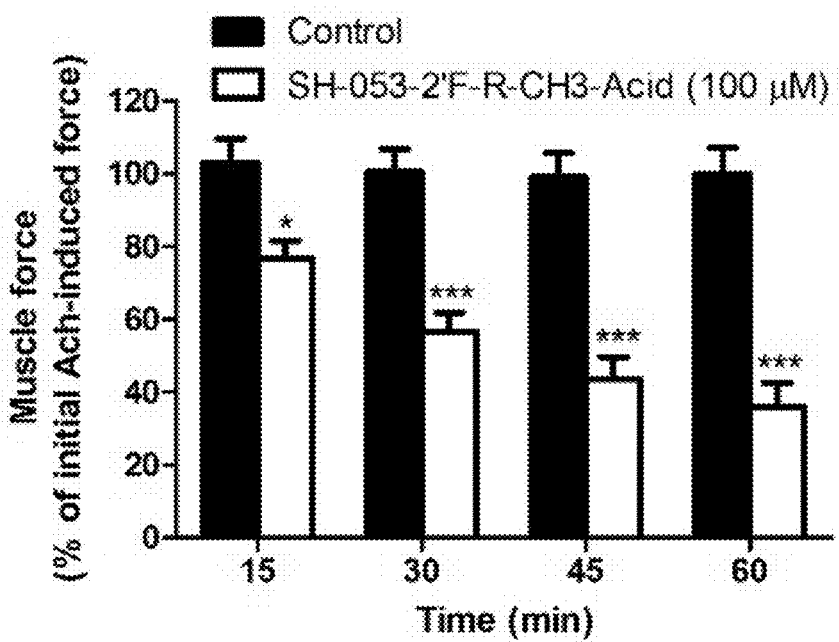
FIG. 4 shows effects of SH-053-2'F—R—CH3 Acid on human airway smooth muscle contractile force.
Figure 5A:
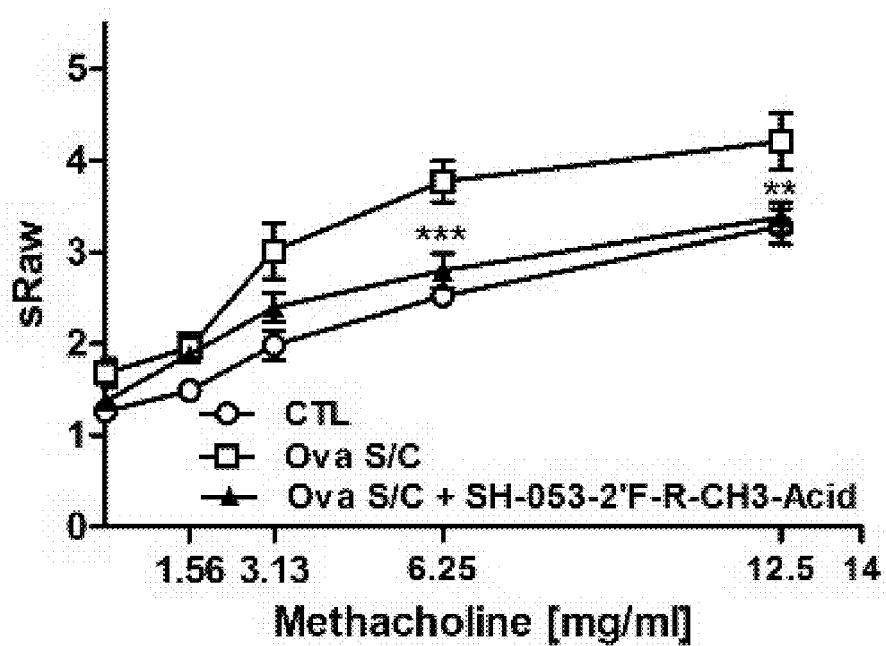
FIGS. 5A-5F show compound effects on airway hyper-responsiveness.
Figure 5B:
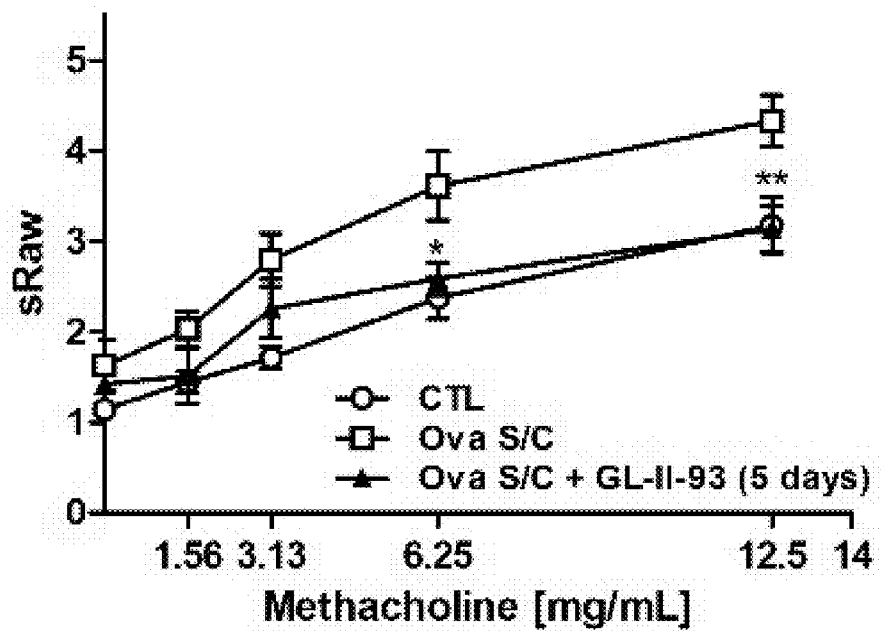
Figure 5C:
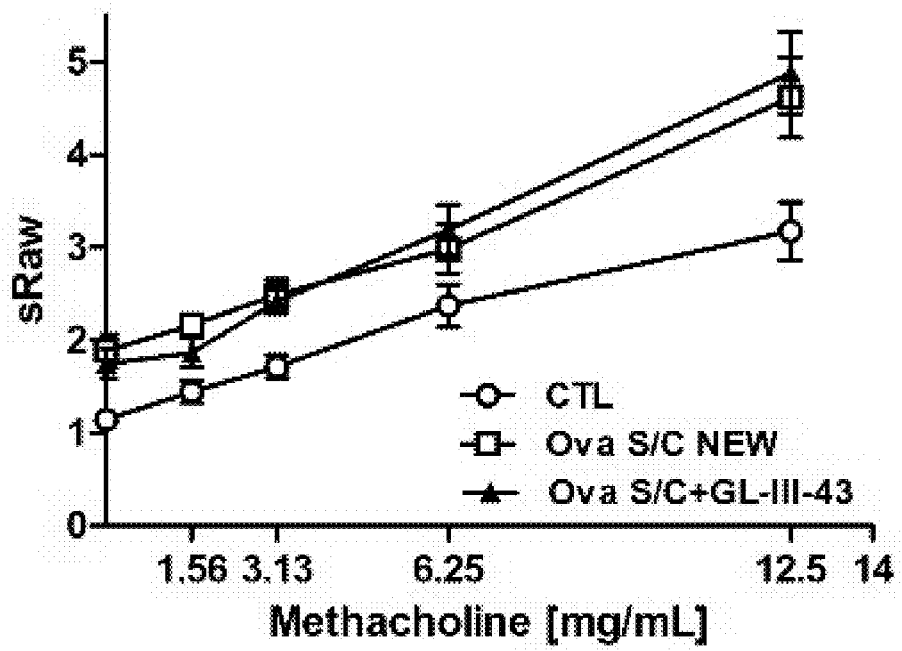
Figure 5D:
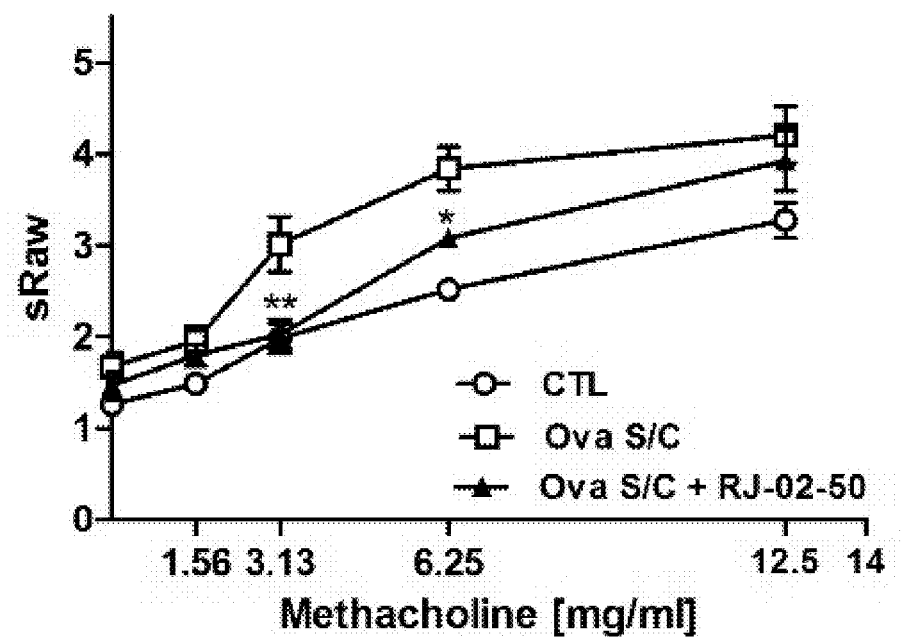
Figure 5E:
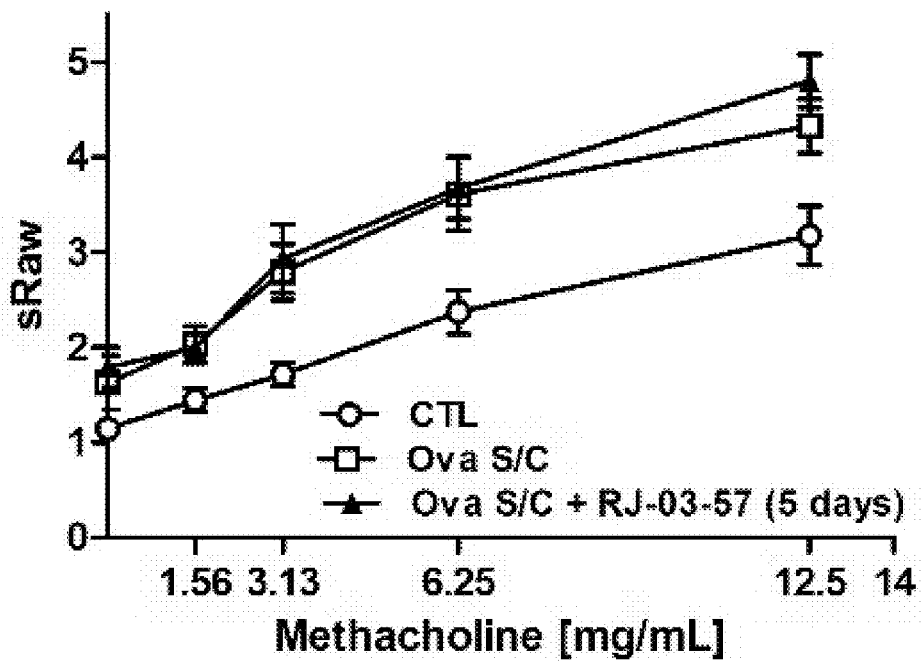
Figure 5F:
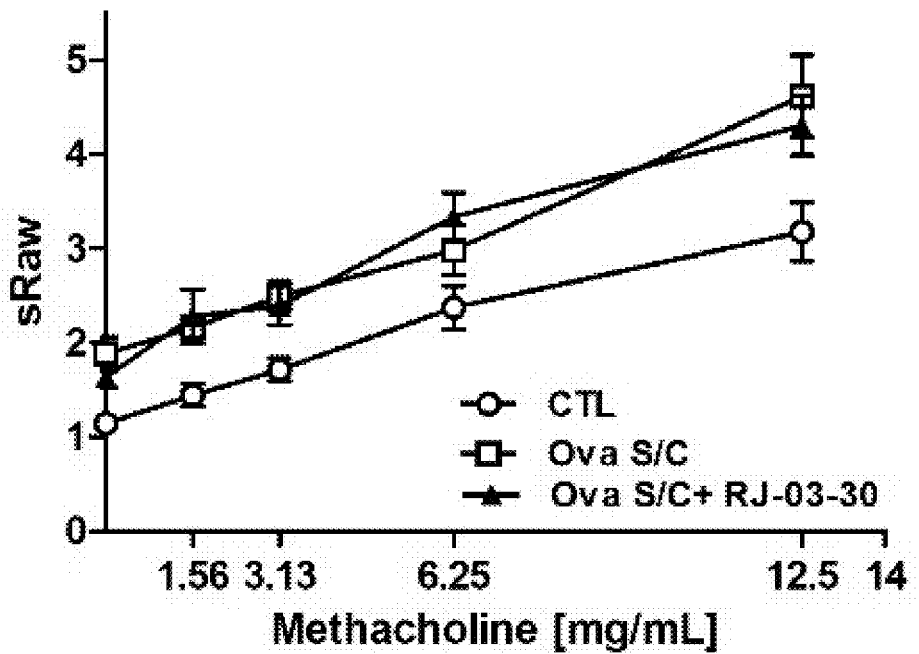
Figure 6A:
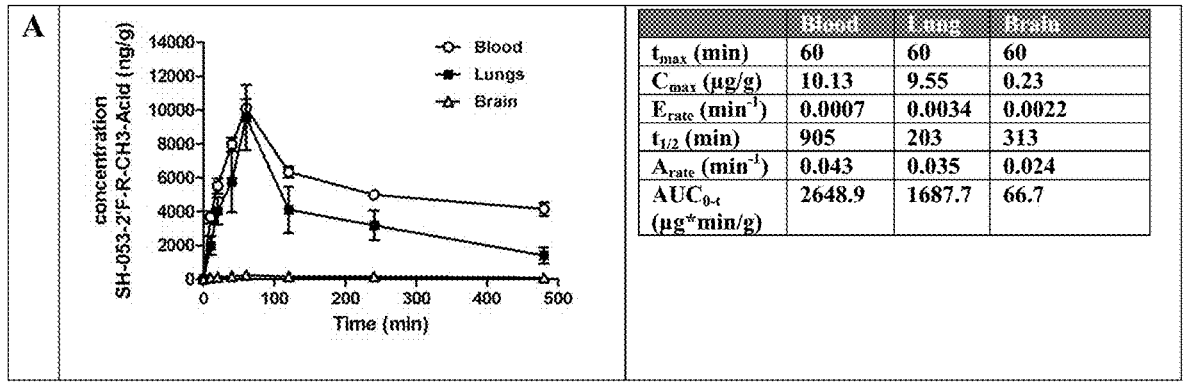
FIGS. 6A-6D show pharmacokinetic profiles of compounds in mice blood, lungs, and brain.
Figure 6B:
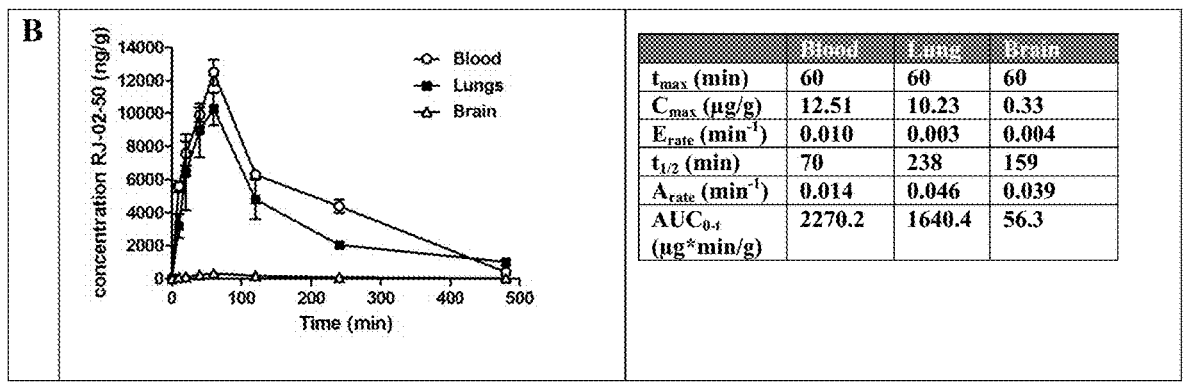
Figure 6C:
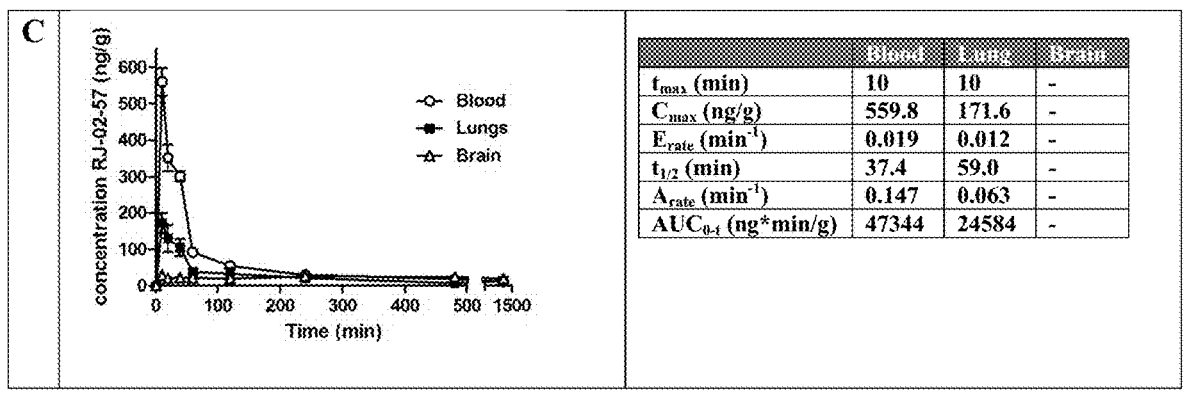
Figure 6D:
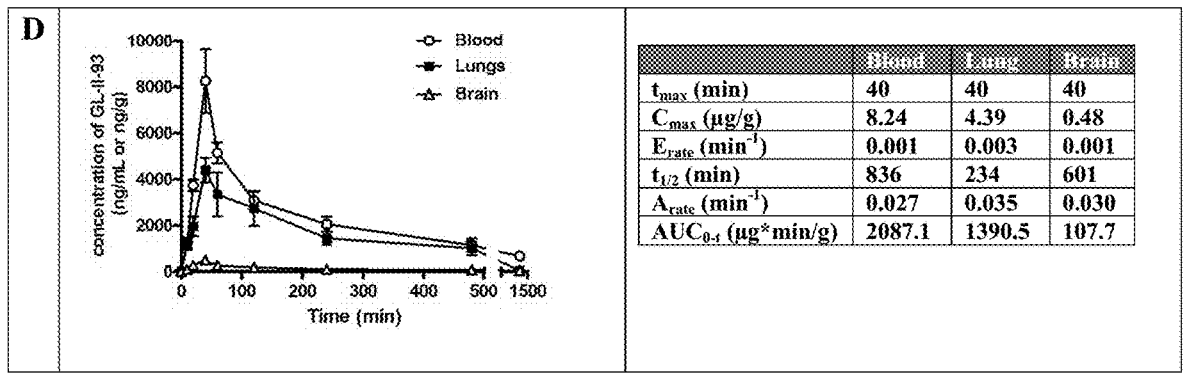

Human airway smooth muscle strips were dissected from human trachea obtained from healthy donor lungs incidental to lung transplantations. Studies were reviewed by the Columbia University Institutional Review Board (IRB) and deemed not to be human subject research. Strips were suspended as above in organ baths in oxygenated KH buffer at 37° C. at 1.5 g of resting tension. Following equilibration for 1 hour with buffer exchanges every 15 minutes, strips were contracted with 3 cycles of increasing concentrations of acetylcholine (100 nM-1 mM) will extensive buffer exchanges between and after these pre-contractile challenges. MK571 (10 μM), pyrilamine (10 μM) and tetrodotoxin (1 μM) were added to the buffer before each strip was contracted to its individually calculated $EC_{50}$ concentration of acetylcholine. When a plateau in the increase in contractile force was achieved (typically 15 minutes) 100 μM of compound or its vehicle (0.2% ethanol) was added to the buffer and the maintenance of contractile force was continuously measured over 1 hour. The remaining contractile force at 15, 30, 45 and 60 minutes was expressed as a percentage of the initial acetylcholine-induced contractile force. FIG. 4 shows airway smooth muscle contractile force in human airway smooth muscle. Human tracheal airway smooth muscle strips were contracted with an $EC_{50}$ concentration of acetylcholine (Ach) and then treated with 100 μM of SH-053-2F'F—R—CH3-Acid or the vehicle 0.2% ethanol. Muscle force was measured at 15, 30, 45, and 60 minutes after addition of compound. Data are expressed as the percent of the initial Ach-induced contractile force. Individual muscle strips from at least seven humans were used. A 2way ANOVA was used to calculate significance with *(p<0.05), (p<0.01) or *(p<0.001) p-values are given for each condition. SH-053-2F'F—R—CH3-Acid reduced the constriction of human airway smooth muscle after 15 minutes for a period of at least 60 minutes.

Example 20. Compound Effects on Allergen-Induced Mouse Asthma Model

Drug treatment protocol: Sterile solutions of compounds were prepared in 2% hydroxypropyl methylcellulose solution (Sigma-Aldrich, St. Louis, MO) and 2.5% polyethylene glycol (Sigma Aldrich, St. Louis, MO) for oral administration in a biological safety cabinet. A fine suspension was obtained by grinding the mixture with a mortar and pestle. Drugs were administered individually at 100 mg/kg by oral gavage (200 ul) with 20 G gavage needles (Kent Scientific Corporation, Torrington CT) to groups of ova s/c BALB/c twice daily for 5 days during the ova challenge period. Mice received a single p.o. dose of the compounds just before airway parameter measurements. Compounds for i.p. injection were prepared in 10% DMSO, 40% propylene glycol, and 50% PBS and given as 100 ul injection. Mice were monitored daily after drug administration. Assessment of Airway hyper-responsiveness: Airway hyper-responsiveness to methacholine in conscious, spontaneously breathing animals was measured by DSI's Buxco® FinePointe Non-Invasive Airway Mechanics (NAM) instrument. Before measurements were taken, mice were acclimated to the chambers 15 minutes daily for 5 days. In addition, an ovalbumin sensitization and challenge protocol consists of randomized male BALB/c mice that were sensitized three times with intra-peritoneal (i.p.) injections of 2 mg/kg/d of ovalbumin (Ova) (Sigma-Aldrich, St. Louis, MO) emulsified in 2 mg of Alum (Imject Alum; Thermo Scientific, Pierce, Rockford, IL) on days 0, 7 and 14 in a total volume of 100 μL. The mice were then challenged intra-nasally (i.n.) with 1 mg/kg/d Ova for 5 days from days 23-27. Control mice were sensitized with Ova and challenged with saline. The chambers were also calibrated each time before data collection. Briefly, the nasal chamber in combination with the thoracic chamber allows the computation of specific airway resistance (sRaw). The FinePointe software computes specific airway resistance (sRaw) with all other ventilatory parameters derived by the NAM analyzer. Mice were exposed to aerosolized PBS (for the baseline measurement) or methacholine (1.5625-12.5 mg/mL) for 1 minute and readings were taken and averaged for 3 minutes after each nebulization. Data obtained were presented as sRaw versus the methacholine concentration (mg/mL) used to generate the aerosol. FIG. 5A-5F show compound effects on airway hyperresponsiveness. Specific airway resistance (sRaw) was measured at increasing dosages of methacholine by a DSI's Buxco FinePointe non-invasive airway mechanics instrument. Ova s/c BALB/c mice were administered all compounds via oral gavage, 100 mg/kg twice daily for 5 days. Data represent mean±SEM from 10 mice in each group. *, , and * indicate p<0.05, p<0.01, p<0.001 significance, respectively, compared to vehicle treated ova s/c BALB/c mice. Compounds RJ-03-57, RJ-03-30 and GL-III-43 were not able to alleviate airway hyperresponsiveness. However, compounds SH-053-2F'F—R—CH3-Acid, GL-II-93 and RJ-02-50 reduced airway hyperresponsiveness at one or multiple concentrations of methacholine.

Example 21. Pharmacokinetic Analysis of Compounds

Determination of pharmacokinetic parameters in mice. Female Swiss Webster mice received intra-gastric gavage of vehicle or compound formulated in 2% hydroxypropyl methylcellulose solution and 2.5% polyethylene glycol at a dose of 25 mg/kg. At 10, 20, 40 60, 120, 240, 480 and 1440 minutes, the blood (collected into heparinized tubes), lungs and brain were harvested and samples stored in liquid nitrogen until analysis. Sample preparation and LC/MS: Blood samples were thawed on ice, vortexed for 10 seconds, and a 100 μL aliquot was taken and added to 400 μL cold acetonitrile containing [100 nM 4,5-diphenyl imidazole, 100 nM HZ-166, RJ-02-50 or SH-053-2'RCH3-Acid] internal standard (I.S.). Samples were vortexed for 30 seconds and centrifuged at 10,000 RPM for 10 minutes. The supernatant layer was then transferred to clean tubes and evaporated using Speedvac concentrator. The residue was reconstituted with 400 μL of mobile phase and spin-filtered through 0.22 m nylon centrifugal filter units (Costar). After reconstitution, the samples are properly diluted, verapamil or 4,5-diphenyl imidazole was added and 5 μL of the sample was injected to the LC-MS/MS. Brain and lung tissue samples were thawed, weighed, and homogenized directly into 400 μL acetonitrile containing I.S. using a Cole Palmer LabGen 7B Homogenizer. Samples were centrifuged for 10 minutes at 10,000 RPM. The supernatant was then retrieved, and prepared in the same manner as the blood samples for LC-MS/MS analysis. High performance liquid chromatography (HPLC) was performed with Shimadzu Nexera X2 LC30AD series pumps (Shimadzu, Kyoto, Japan). Analytes were separated by a Restek Pinnacle II C18 column (2.1 mm×100 mm, 5 μm particle size, Restek, California, US) under gradient elution at a flow rate of 0.5 mL/minute (SH-053-2'R—CH3-Acid), 0.4 mL/minute (RJ-02-50), and 0.6 mL/min (RJ-03-57 and GL-II-93). The mobile phase was acetonitrile or methanol and water (both containing 0.1% formic acid). Time program: 20% B→70% B (3 minutes)→99% B (5 minutes), hold at 99% B (8 minutes), return to 10% B (9 minutes), hold (9.5 minutes) (SH-053-2'R-acid), 70% B→70% B (6 minutes) (Isocratic for SH-053-2'F—R—CH3-Acid), 20% B→70% B (2 min)→99% B (4 min), hold at 99% B (4.5 min), return to 20% B (4.75 min), hold (5 min) (RJ-03-57) and 20% B→70% B (2 min)→99% B (5 min), hold at 99% B (5.5 min), return to 20% B (5.75 min), hold (6 min) (GL-II-93) at a column temperature: 40° C. Analytes were monitored under positive mode by Shimadzu 8040 triple quadrupole mass analyzer (Shimadzu, Kyoto, Japan) electrospray and atmospheric pressure ionization run in dual (DUIS) mode. The following transitions are monitored in multiple reaction monitoring (MRM) mode. Ion pairs for RJ-02-50 are m/z 327.85>281.95, m/z 327.85>264.05, m/z 327.85>254.10, m/z 327.85>236.80 and m/z 327.85>212.75. Transition ion pairs for SH-053-2'F—R—CH3-Acid are m/z 360.0>342.10, m/z 360.0>316.00, m/z 360.0>301.10, m/z 360.0>249.05 and m/z 360.0>219.90. Transition pairs for HZ-166 are m/z 356.90>311.15, m/z 356.90>283.15, and m/z 356.90>282.15. Transition pairs for 4,5-diphenyl imidazole are m/z 220.80>193, m/z 220.80>167, m/z 220.80>151.95 and m/z 220.80>115 transition pairs for verapamil (internal standard) are m/z 454.70>165.05, m/z 454.70>150 and m/z 454.70>303.0. Transition pairs for RJ-03-57 are m/z 337.85>265.95, m/z 337.85>252.05, m/z 337.85>238.0, 337.83>224.95 and m/z 337.85>209.85. Transition pairs for GL-II-93 are m/z 413.90>396, m/z 413.90>368, m/z 413.90>355.05, m/z 413.90>302.95, m/z 413.90>326.80, m/z 413.90>276.05, and m/z 413.90>248.20. Collision energy is optimized for each transition to obtain optimal sensitivity. The mass spectrometer was operated with the heat block temperature of 400° C., drying gas flow of 15 L/minute, desolvation line temperature of 250° C., nebulizing gas flow of 1.5 L/minute, and both needle and interface voltages of 4.5 kV. The response acquisition was performed using LabSolutions software. Standard curves were fitted by a linear regression and the validation samples were calculated back by the calibration curve of that day. The mean and the coefficient of variance (CV) were calculated accordingly. Accuracy was calculated by comparing calculated concentrations to corresponding nominal. Pharmacokinetic parameters were calculated with PK solutions software 2.0 and fitted to the following equation: $c = A \cdot e^{-at} + B \cdot e^{-bt} + C \cdot e^{-ct}$. FIGS. 6A-6D show pharmacokinetic profiles of compounds in mice blood, lungs, and brain. Time-dependent systemic distribution of compounds administered at 25 mg/kg via oral gavage. RJ-02-50, SH-053-2'F—R—CH3-Acid, and GL-II-93 exhibit excellent bioavailability in mouse, whereas RJ-03-57 has a moderate absorption and fast clearance.

Example 22. Changes of Inflammatory Cell Numbers in Mouse BALF by Compounds

Figure 7A:
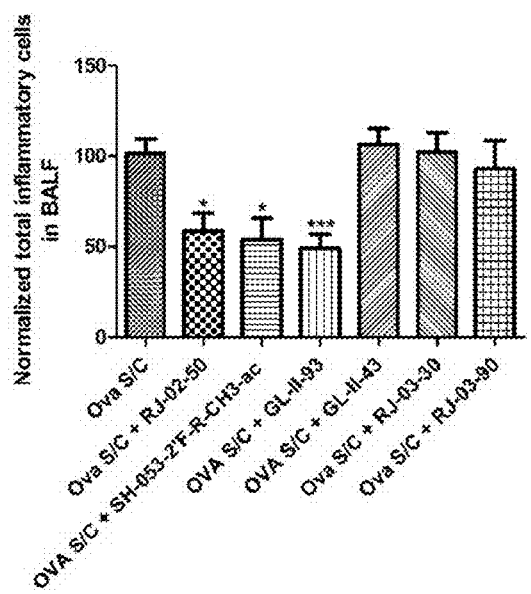
FIGS. 7A-7C show effects of compounds on inflammatory cells.
Figure 7B:
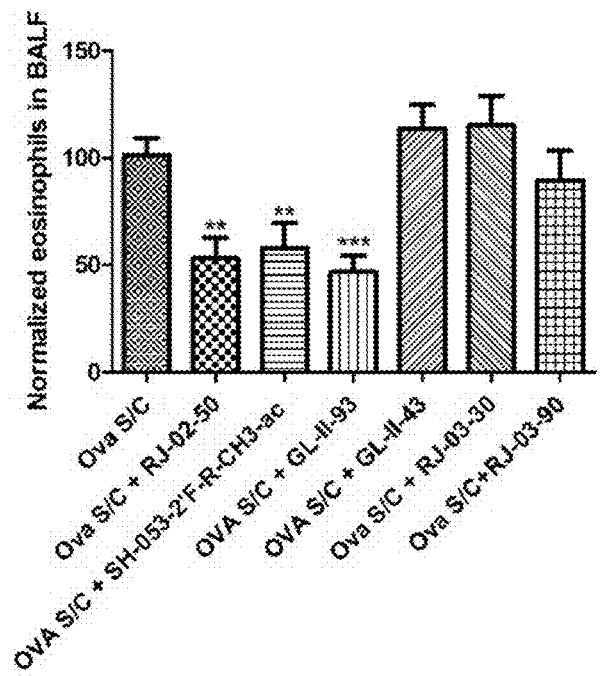
Figure 7C:
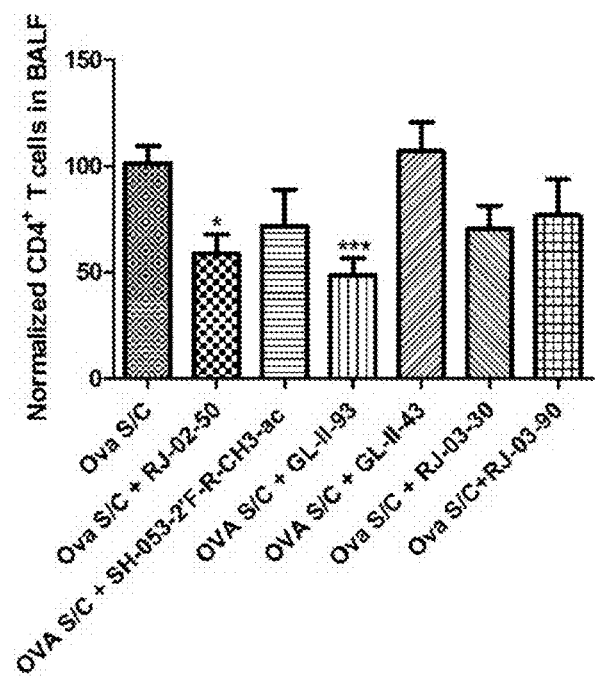

Determination of anti-inflammatory properties of compounds were investigated in an allergen induced mouse model of asthma. At the day of analysis, bronchoalveolar lavage (BAL) was performed with 1 mL of Ca2+ and Mg2+ free PBS. Red blood cells (RBCs) were lysed using BD red blood cell lysis buffer (BD Pharmingen, San Jose, CA). BALF was split into four different tubes and non-specific binding to Fc receptors was blocked for 5 minutes using 6 μg/mL of 2.4 G2 mouse BD Fc Block™ (BD Pharmingen, San Jose, CA). BALF cells were stained for 30 minutes at 4° C. in the dark with 100 μL BSA stain buffer (BD Pharmingen, San Jose, CA) containing the final concentrations of the following antibodies: anti-mouse CD45 APC (1:1000, 30-F11, Affymetrix eBiosciences, San Diego, CA), FITC rat anti-mouse CD4 (1:500, RM4-5, BD Pharmingen, San Jose, CA), PE Rat Anti-Mouse Siglec F (1:500, E50-2440, BD Pharmingen, San Jose, CA) and mouse CCR3 PE-conjugated antibody (1:40, 83101, R&D systems Inc, Minneapolis, MN). Flow cytometric studies were done using the BD FACS Calibur (BD Pharmingen, San Jose, CA) and data analyzed subsequently using Cell Quest pro software (BD Pharmingen, San Jose, CA). General gating for immune cells were followed. Total inflammatory cell count was obtained by running all samples on high (60 μL/min) for 180 seconds. The gated anti-mouse CD45 positive events in the fourth channel (FL4) were used to calculate the total inflammatory cell count as cells/mL. The frequencies of CCR3+/Siglec F were used for quantification of eosinophils and CD4+ for CD4+ T cell populations in their respective gates were multiplied by the total inflammatory cell count (cells/mL) to obtain the differential cell population. Statistical analysis: Data were analyzed using GraphPad Prism 4 (GraphPad Software, San Diego, CA) and expressed as mean±SEM. One-way analysis of variance (ANOVA) with Dunnet post hoc test or two-way ANOVA with Bonferroni post hoc test were performed for statistical difference for multiple groups. FIGS. 7A-7C show effects of compounds on inflammatory cells. Groups of 10 ova s/c BALB/c mice were administered compounds at 100 mg/kg twice daily for 5 days. BALF was harvested from each animal and used for (A) quantification of total inflammatory cells; (B) eosinophils; (C) $CD_4^+$ T cells. Cells were stained with mouse $CD45^+$ APC antibody, and samples were analyzed with BD FACS Calibur on high flow rate (60 μl/minute) for 180 seconds. The gated positive events in the fourth channel (FL4) were used to calculate the total inflammatory cell count as cells/ml. Quantification of specific leukocyte population (B) eosinophils (C) $CD4^+$ T cell populations were stained with specific antibodies and detected by flow cytometry. Data represent mean±SEM from 10 mice in each group. *, , and * indicate $p<0.05$, $p<0.01$, and $p<0.001$ significance, respectively, compared to vehicle treated ova s/c BALB/c mice. Compounds GL-II-43, RJ-03-30, RJ-03-90 did not modulate the numbers of inflammatory cells. However, RJ-02-50 and GL-II-93 did reduce the numbers of eosinophils and $CD4^+$ T cells in the asthmatic mouse lung.

SH-053-2'F'F—R—CH3-Acid reduced the numbers of eosinophils but not CD4+ T cells.

Figure 8:
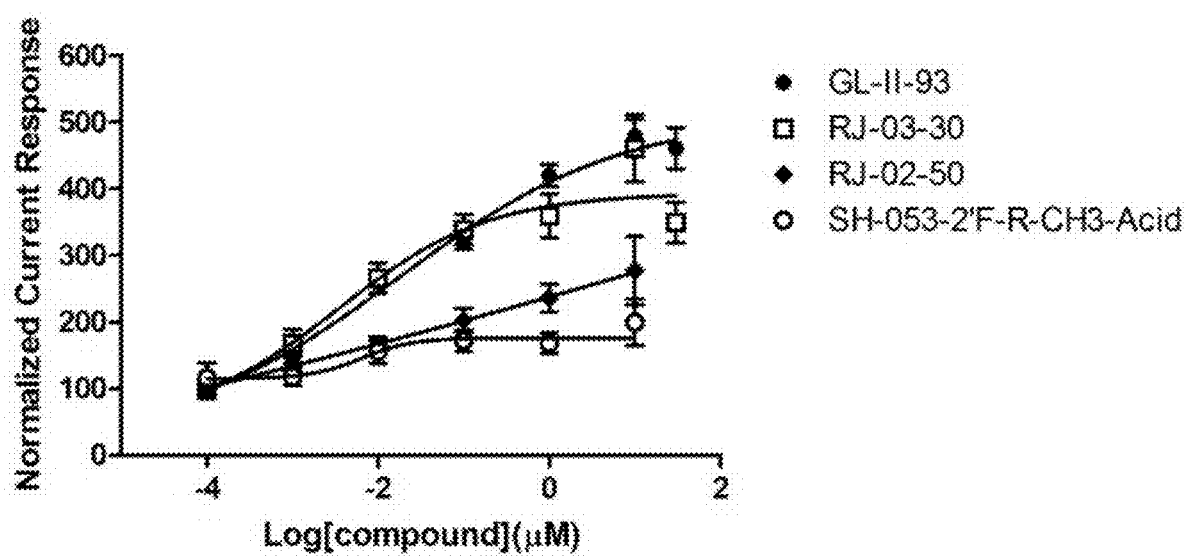
FIG. 8 shows current recordings in the presence of 600 nM GABA and increasing concentrations of compounds applied together for 3 seconds using CD4+ T-cells isolated from ova s/c BALB/c mice spleen.

Example 23. Electrophysiological Measurement of CD4+ T Lymphocytes in the Presence of Compounds To determine the effect of compounds on lymphocytes, CD4+ T cells from Ova S/C mice were isolated and their interaction with compounds was measured by automated patch clamp. Splenocytes from ova s/c BALB/c mice were prepared following BD Biosciences instructions for preparation of murine splenocytes and red blood cell lysed using BD Pharm Lyse™ lysing solution (BD Biosciences, San Jose, CA). Cells were maintained in suspension in RPMI 1640 medium with L-glutamine (Thermo Fisher Scientific Inc., Rockford, IL) supplemented with 10% (v/v) fetal bovine serum, 10 μM 2-mercaptoethanol and 1% penicillin/streptomycin in the presence or absence of 100 μg/mL ovalbumin. The cells were maintained in 5% $CO_2$, 95% humidified air at 37° C. for 48 hours. The IonFlux plate layout consists of units of 12 wells: two wells contain intracellular solution (ICS containing 346 mM CsCl, 1 mM $CaCl_2$, 1 mM $MgCl_2$, 11 mM EGTA, 10 mM HEPES, pH 7.2 with CsOH), one contains cells diluted in extracellular solution (ECS containing 140 mM NaCl, 5 mM 349 KCl, 2 mM $CaCl_2$), 1 mM $MgCl_2$, 5 mM D-glucose monohydrate, and 10 mM HEPES, pH 7.4 with NaOH), eight contain the compounds of interest diluted in ECS, and one well is for waste collection. Cells are captured from suspension by applying suction to microscopic channels in ensemble recording arrays. Once the array is fully occupied, the applied suction breaks the membranes of captured cells, which establishes whole cell voltage clamp. For compound applications, pressure is applied to the appropriate compound wells, which introduces the compound into the extracellular solution rapidly flowing over the cells. For recording $GABA_AR$ induced currents, cell arrays were voltage clamped at a hyperpolarizing holding potential of −50 mV. Prior to use on the automated patch clamp, cells were centrifuged at 380 g for 5 minutes and resuspended gently in ECS. This was repeated two more times before the cells were dispensed into the plate. GABA and muscimol were diluted to appropriate concentrations in ECS to appropriate concentrations before application and data recorded. FIG. 8 shows current recordings in the presence of 600 nM GABA and increasing concentrations of compounds applied together for 3 seconds using CD4+ T-cells isolated from ova s/c BALB/c mice spleen. The concentration-dependent current responses of CD4+ T-cells in the presence of 600 nM GABA and increasing concentration of compounds were carried out with an N of 16 and normalized to the current response of 600 nM GABA. Compound RJ-02-50 potentiated the GABA-induced membrane current more than SH-053-2'F'F—R—CH3-Acid. Importantly, GL-II-93 and RJ-03-30 evoked a very pronounced GABA-induced transmembrane current.

Example 24. In Vivo Modulation of Lung Cytokine Expression by Compounds

Figure 9:
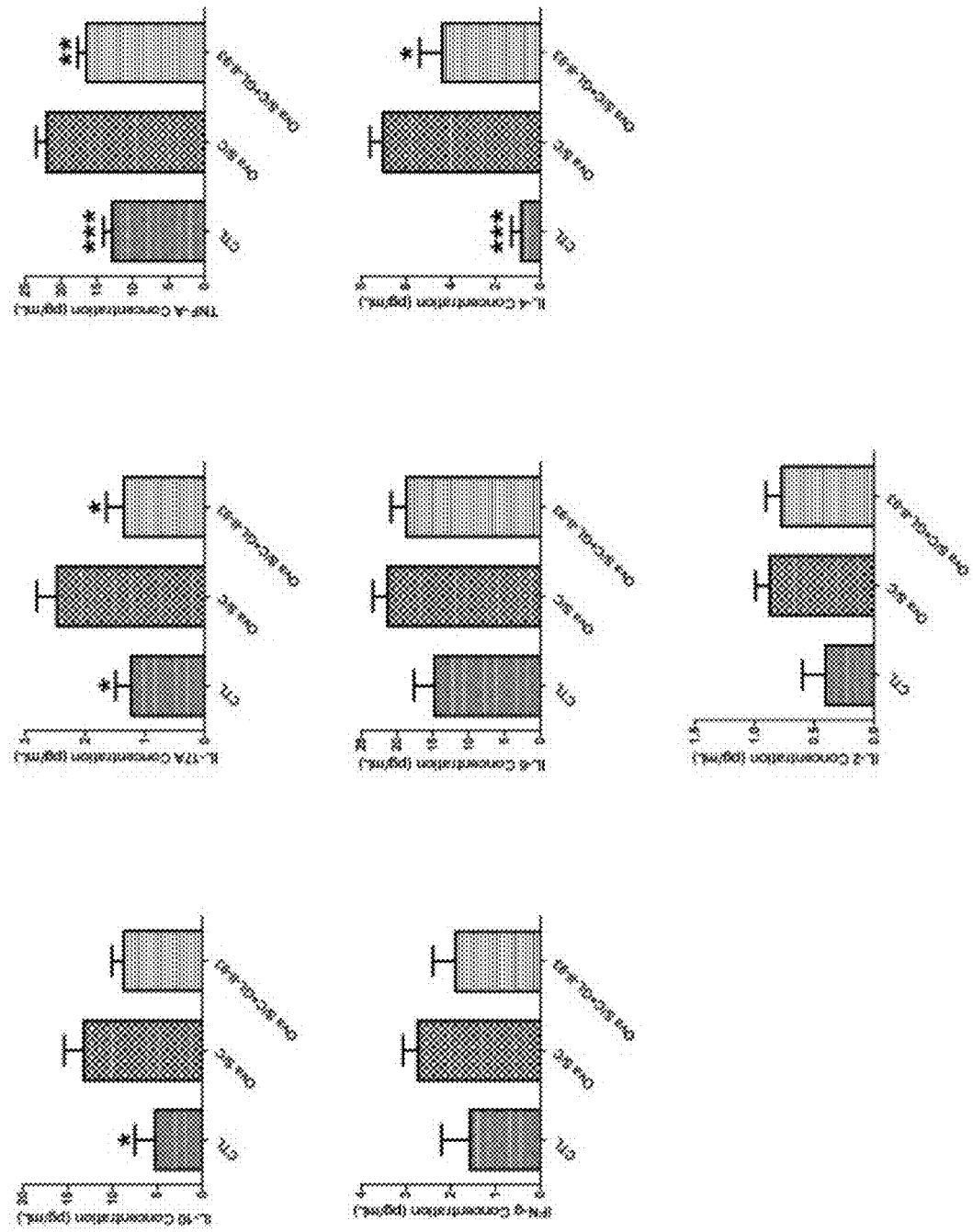
FIG. 9 shows anti-inflammatory properties of compounds in respect to cytokine production.

Anti-inflammatory properties of compounds in respect to cytokine production were investigated after the AHR measurement by harvesting the lungs of treated and non-treated Ova S/C mice (N=10). Whole lungs were homogenized in 200 μL of T-PER® tissue protein extraction reagent (Thermo Fisher Scientific Inc., Rockford, IL) containing 1× protease inhibitor cocktail using a hand-held tissue homogenizer. Homogenized lung samples were centrifuged at 10,000 RPM for 5 minutes to pellet cell/tissue debris. Tissue supernatant was collected for cytokine analysis using BD cytometric bead array mouse Th1/Th2/Th17 cytokine kit (BD Biosciences, San Jose, CA) following manufacturer's instruction. Data were analyzed using GraphPad Prism 4 (GraphPad Software, San Diego, CA) and expressed as mean±SEM. One-way analysis of variance (ANOVA) with Dunnet post hoc test was performed for statistical difference for multiple groups. FIG. 9 shows quantification of cytokine levels in the mouse lung. Among the cytokines tested IL-10, IL-17A, TNF-α and IL-4 were expressed significantly higher in the lungs of ova s/c mice in comparison to normal BALB/c mice. Data represent mean±SEM from 10 mice in each group. *, , and * indicate $p<0.05$, $p<0.01$, and $p<0.001$ significance. The ova s/c mice expressed higher levels of IFN-γ, IL-6, and IL-2 but the change was not significant in comparison to normal mice. Ova s/c mice treated with GL-II-93 exhibited reduced the levels of IL-17, TNFα, and TL-4 in the mouse lung.

Example 25. Absence of Mucus Hypersecretion Modulation by Compounds

Figure 10A:
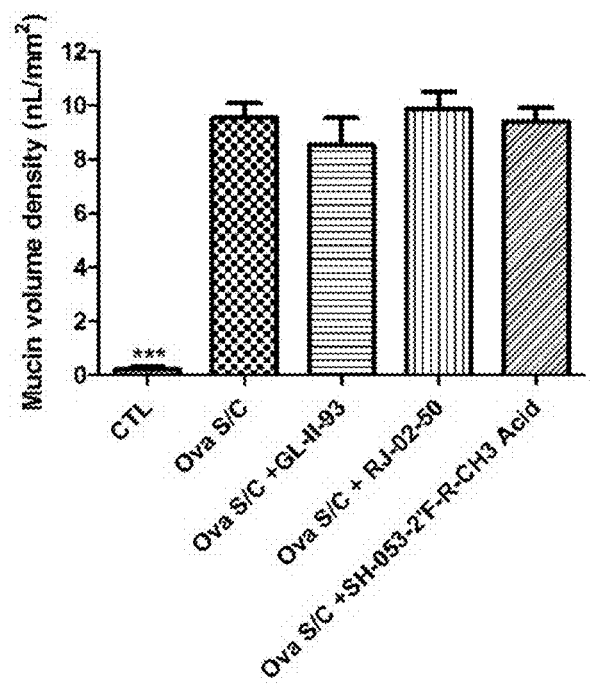
FIGS. 10A-10B show compound effects on mucin production.
Figure 10B:
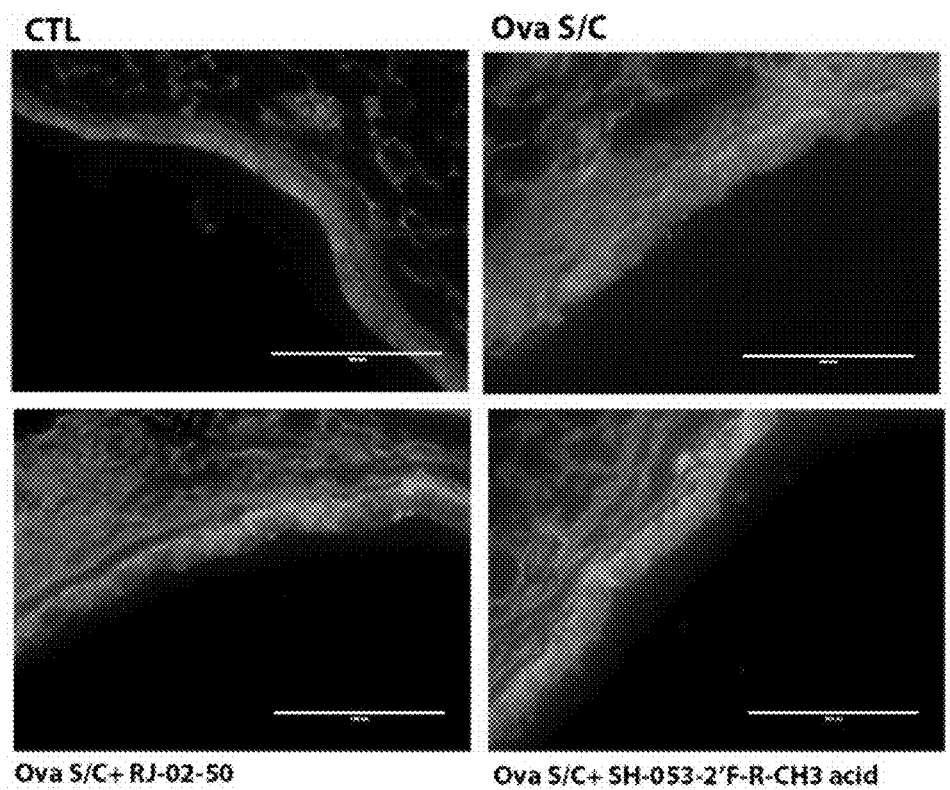

Pharmacodynamic effects of compounds in respect to mucus production were investigated after the AHR measurement by harvesting the lungs of treated and non-treated Ova S/C mice followed by formalin fixation and paraffin embedding. Sections were prepared from one lobe (including large and small airways) and processed for standard H&E (for general histopathology and inflammation) and PAS (for mucous cell; as cells/mm of basement membrane) staining. FIGS. 10A-10B show compound effects on mucin production: (A) Morphometric quantification of mucin volume density and (B) representative images of mucin (red) in the airway epithelium (green) with periodic acid fluorescent Schiff's stain. Balb/c mice were administered compounds at 100 mg/kg twice for five days. Data represent mean±SEM from 5-7 mice in each group. Scale bar represents 100 μm. GL-II-93, RJ-02-50 and SH-053-2'F—R—CH3 Acid did not change the production of mucin.

Example 26. Inhibition of Lung Cell Proliferation by Compounds

Figure 11:
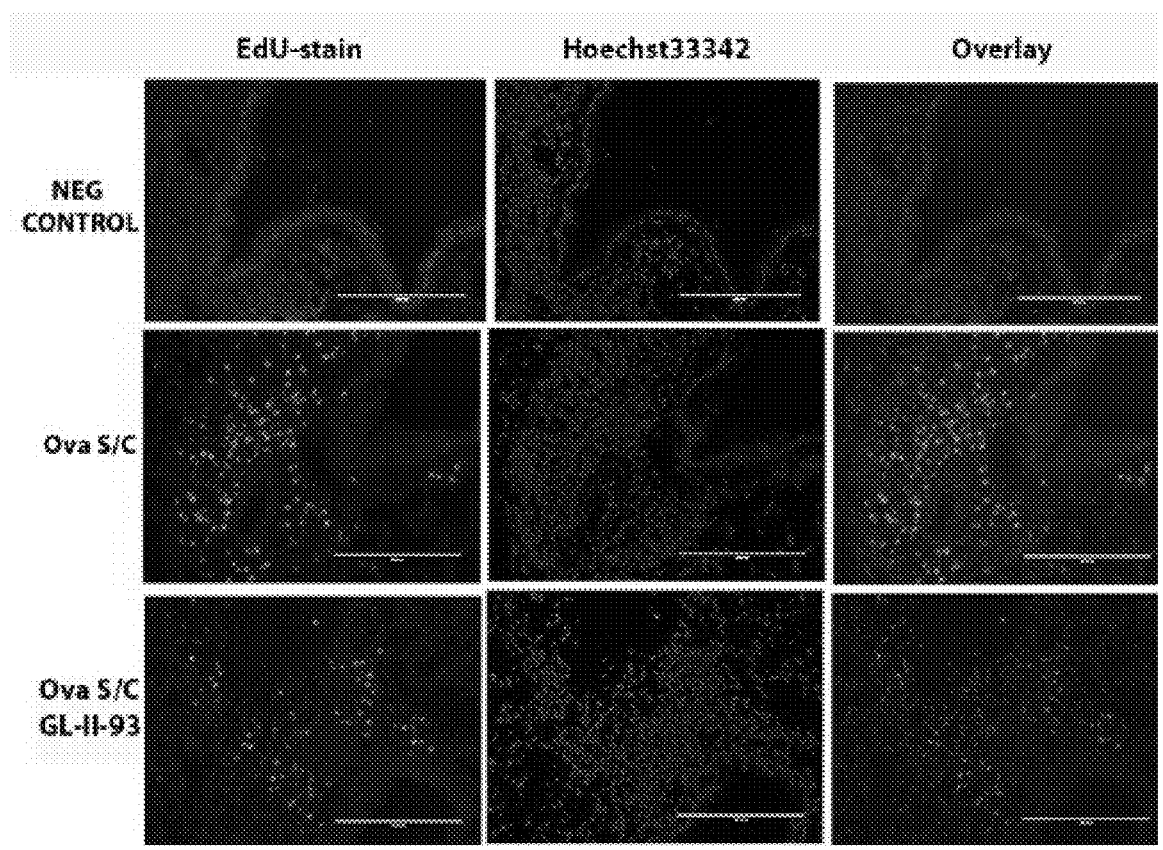
FIG. 11 shows proliferation of lung cells, either non-treated or treated with GL-II-93.

ASM hyperplasia was determined by incorporation of EdU into the DNA of newly formed cells. Herein, at the end of the ovalbumin sensitization and challenge protocol, mice received a single i.p. injection of EdU (Invitrogen, Carlsbad, CA) at a dose of 100 mg/kg. Mice were euthanized 4 hours after injection and the lungs formalin fixed, harvested and paraffin embedded. 6 μm sections of formalin fixed and paraffin embedded lung sections were mounted onto Fisher Superfrost Plus Slides. EdU staining was conducted using Click-iT™ EdU imaging kit (Invitrogen, Carlsbad, CA) according to manufacturer's instructions. Briefly lungs were deparaffinized in histoclear and rehydrated in graded ethanol. Tissue sections were washed twice with 3% bovine serum albumin (BSA) in PBS and permeablized with 0.5% Triton X-100 in PBS for 20 minutes. The sections were again washed twice with 3% BSA in PBS and then incubated with a Click-iT™ reaction cocktail containing Click-iT™ reaction buffer, CuSO4, Alexa Fluor® 488 Azide, and reaction buffer additive for 30 minutes in the dark. The sections were washed once more with 3% BSA in PBS. For DNA staining, sections were washed once with PBS and then incubated with 5 μg/mL Hoechst 33342 for 30 minutes. The slides were then washed twice with PBS and coverslipped with Permount mounting media. All steps were carried out at room temperature. FIG. 11 shows proliferation of lung cells. Lung sections of non-treated and GL-II-93 treated Ova s/c mice were analyzed for the incorporation of EdU, a thymidine analog that can be visualized after click chemistry with a fluorescent azide. For the negative control EdU was not injected resulting in no visible fluorescence. Non-treated Ova S/C mice showed a high proliferation rate in comparison to GL-II-93 treated animals. Nuclei specific Hoechst 33342 stain ensure similar cell density between the two sections that are compared in FIG. 11.

Example 27. Virus-Induced Asthma Model

Efficacy of $GABA_AR$ compounds in chronic lung disease will be studied in a virus induced asthma model. C57BL/6 mice (at 6-20 weeks of age; groups of 10) will be inoculated intranasally with 2×105 pfu SeV (Strain 52; ATCC) or UV-inactivated SeV (UV-SeV) (69), at day 0. Mice are monitored daily for weight and activity; with chronic disease being well established by day 49 post-inoculation (P-I). Four experimental groups will be arranged, with test compound (or vehicle) administered i.p. during days 49-56 P-I. For prophylactic studies, treatment would be administered during days 13-21, followed by disease measurement at days 49-56; to model a dosing regimen that corresponds to childhood treatment following RSV exposure (thus, investigating if immune modulation early after viral infection or during the acute post-infection phase can influence development of later inflammatory lung disease). Serial non-invasive AHR measurements (sRAW) in response to methacholine will be measured in all Groups on days 13, 49, and 56 PI. Following AHR measurements on day 56, animals will be euthanized and BALF, blood, and tissue samples will obtained. BALF will be collected in 1 ml PBS, centrifuged, and the cell supernatants collected for cytokine analysis as above. The cell pellet will be resuspended in RPMI and samples taken for differential cell counts (Diff-Quik) and flow cytometry. For flow cytometry, cell preparations will be stained with fluorophore labeled monoclonal antibodies to mouse CD1d (Invitrogen) and Mac-3 (BD) for M2 macrophages or $CD_3$ and NK1.1 (both Invitrogen) for NKT cells. Antibody labeled cells will be examined with a FACS Calibur instrument (BD Biosciences) and data analyzed with FlowJo software (Tree Star, Ashland, OR) (69, 70, 84). All other lung tissue and biochemical testing will be performed and data analyzed as in the OVA model.

Example 28. Chronic Obstructive Pulmonary Disease (COPD) Model

Efficacy of $GABA_AR$ compounds will be studied by lipopolysaccharide (LPS) lung challenge in mice as a model of human COPD. LPS is a proinflammatory stimulant that is present as a contaminant in cigarette smoke, air pollution, and organic dusts. In humans, chronic exposure to LPS-laden dusts results in decreased lung function. In the acute model, LPS induces a mixed inflammatory reaction with increases in neutrophils and increased tumor necrosis factor (TNF), IL-1, and other mediators in brochoalveolar fluid. Prior to administration, each test compound is diluted in a buffer solution vehicle (phosphate buffered saline, pH 7.4) and filter sterilized. Test compound is administered i.p. in a total volume of 100 ul, in each of the indicated days (thus 3 doses). Approximately one hour after the final i.p. compound administration, mice receive LPS intratracheally using a non-surgical procedure. Mice are first anesthetized by subcutaneous (s.c.) injection with ketamine hydrochloride and xylazine hydrochloride solution (Cat. no. K113; Sigma; 50 mg/kg ketamine HCl). LPS (Cat. no. L2880; Sigma, type O55:B5), dissolved in 50 μL sterile 0.9% NaCl, is instilled intratracheally (i.t.) (20 μg LPS/mouse) via a cannula and syringe (2×25 μl), followed by 100 μl air. Sham-treated mice are instilled i.t. with 50 μL sterile 0.9% NaCl. After i.t. treatment, mice are kept in an upright position for 10 minutes to allow the fluid to spread throughout the lungs. Mice are allowed to recover from anesthesia and the sacrificed 24 hours after using cervical $CO_2$ asphyxiation. Blood is collected via heart puncture in EDTA-containing tubes, immediately centrifuged (2000×g, 10 minutes, 4° C.) and plasma was stored at −80° C. Lungs tissue is removed and snap-frozen for RNA-isolation and MPO analysis. For immunohistochemical analyses lung tissue is placed in 10% phosphate-buffered formalin (pH 7.4).

Example 29. Immune Arthritis Model

Groups of 8-10 male DBA/1j mice (Jackson Laboratories, Bar Harbor, ME, USA) 8-10 weeks of age are immunized with 200 mg bovine collagen II (bCII, Chondrex, Redmond, WA, USA) in 50% complete Freund's adjuvant intradermally at the base of the tail. Mice are similarly boosted 21 days later with 100 mg of bCII in incomplete Freund's adjuvant. Groups of control mice are treated with sham immunizations without bCII. Food and water consumption, body weights, as well as clinically observable joint inflammation are measured throughout the treatment course. Beginning after the initial immunization, mice are administered $GABA_A$ receptor agents of the instant invention 3 times per week for 8 weeks. Compound dosing will be determined as described in Example 22. Serum collagen-specific IgG, IgG1, and IgG2a antibodies in individual control and experimental mice 8 weeks after the final immunization are characterized by microtiter plate ELISA. In the ELISA bCII is used as antigen for coating the plate wells and isotype-specific, fluorophore-conjugated rabbit anti-mouse antibodies are used to quantify primary antibody binding. Wells in the ELISA plates are read using a standard fluorescent plate reader. Compound efficacy will be evidenced by reduction of clinical joint inflammation and/or reduction in IgG antibody titers to bCII in the treated in comparison to control mice.

Example 30. Autoimmune Diabetes Model

Non-obese diabetic (NOD) mice have been used for 30 years in the study of diabetes. NOD mice are characterized by insulitis, a leukocytic infiltrate of the pancreatic islets. Decreases in pancreatic insulin content occur spontaneously in females at about 12 weeks of age and several weeks later in males. Diabetic mice are hypoinsulinemic and hyperglucagonemic, indicating a selective destruction of pancreatic islet beta cells. Compounds of the instant invention are dosed QD or BID for 28 days via one of the route of administration (PO, IP, IM, SC); control animals are similarly given vehicle doses. Doses are determined as described in Example 22. 8-10 mice are assigned per group. Animals are monitored twice per week for body weight, food consumption, water intake, and blood or urine glucose, are measured. Urine glucose can be determined using commonly available test strips (Bayer Diastix). Efficacy of compounds is evidenced by reduction in one or more of these clinical markers in the treated versus the control groups.

All patents, publications and references cited herein are hereby fully incorporated by reference. In case of conflict between the present disclosure and incorporated patents, publications and references, the present disclosure should control.

We claim:

1. A method for reducing airway constriction in a subject, wherein the method comprises administering to the subject in need thereof a therapeutically effective amount of a compound of formula (I):

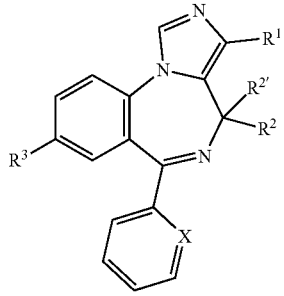

or a pharmaceutically acceptable salt or stereoisomer thereof,
wherein:
$R^1$ is C(O)OH;
$R^2$ is $C_{1-4}$ alkyl, $CF_3$, or $CCl_3$;
$R^{2'}$ is H, $C_{1-4}$ alkyl, $CF_3$, or $CCl_3$;
$R^3$ is Cl, Br, or cyclopropyl; and
X is CF, CCl, CBr, CI, or N.

2. The method of claim 1, wherein the compound, or stereoisomer thereof, is selected from the group consisting of:

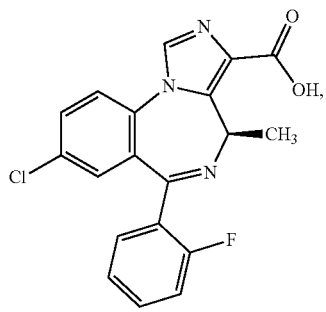

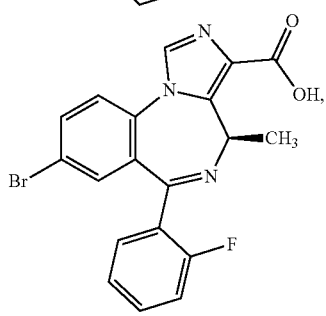

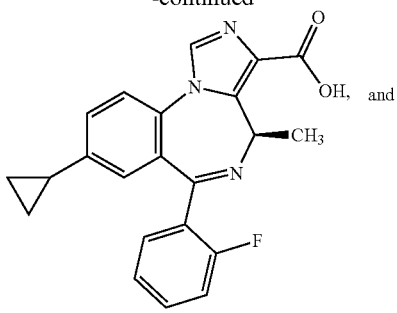

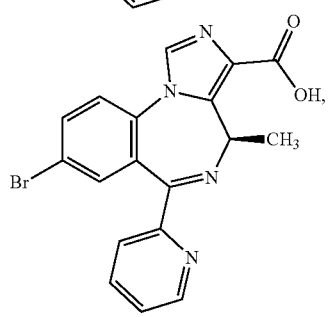

or a pharmaceutically acceptable salt thereof.

3. The method of claim 2, wherein the compound, or stereoisomer thereof, is:

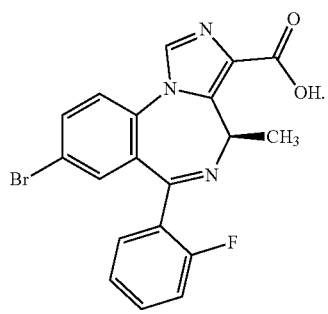 [SMILES: C[C@H]1N=C(c2ccccc2F)c2cc(Br)ccc2-n2cnc(C(=O)O)c21]

or a pharmaceutically acceptable salt thereof.

4. A method for reducing development of disease in a subject having risk factors associated with lung inflammation, wherein the method comprises administering to the subject in need thereof a therapeutically effective amount of a compound of formula (I):

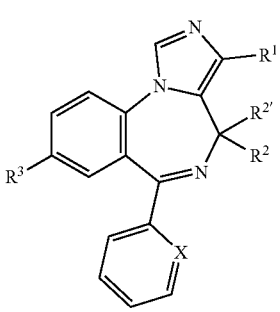

or a pharmaceutically acceptable salt or stereoisomer thereof, wherein:

R¹ is C(O)OH;

R² is $C_{1-4}$ alkyl, $CF_3$, or $CCl_3$;

R²' is H, $C_{1-4}$ alkyl, $CF_3$, or $CCl_3$;

R³ is Cl, Br, or cyclopropyl; and

X is CF, CCl, CBr, CI, or N.

5. The method of claim 4, wherein the compound, or stereoisomer thereof, is selected from the group consisting of:

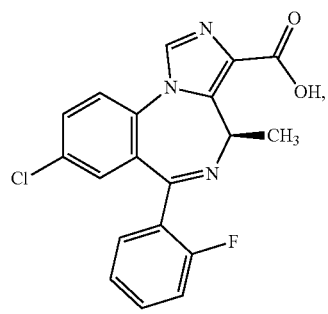

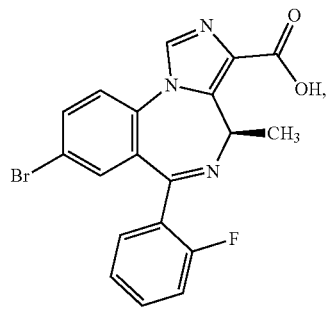

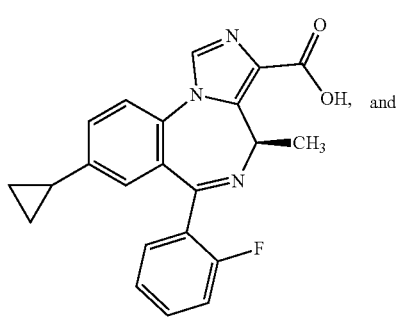

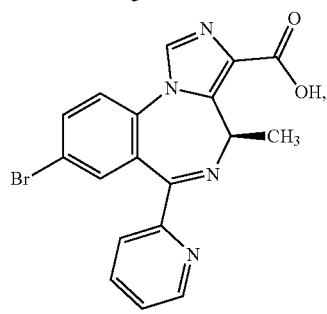

or a pharmaceutically acceptable salt thereof.

6. The method of claim 5, wherein the compound, or stereoisomer thereof, is:

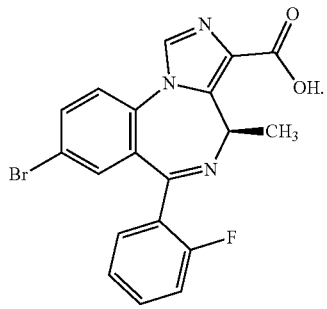 [SMILES: C[C@H]1N=C(c2ccccc2F)c2cc(Br)ccc2-n2cnc(C(=O)O)c21]

or a pharmaceutically acceptable salt thereof.

7. A method for reducing lung inflammation in a subject, wherein the method comprises administering to the subject in need thereof a therapeutically effective amount of a compound of formula (I):

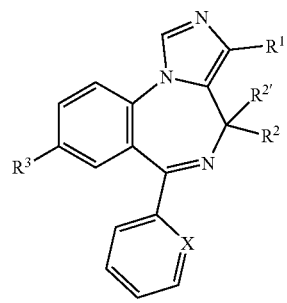

(I)

or a pharmaceutically acceptable salt or stereoisomer thereof, wherein:

R¹ is C(O)OH;

R² is $C_{1-4}$ alkyl, $CF_3$, or $CCl_3$;

R²' is H, $C_{1-4}$ alkyl, $CF_3$, or $CCl_3$;

R³ is Cl, Br, or cyclopropyl; and

X is CF, CCl, CBr, CI, or N.

8. The method of claim 7, wherein the compound, or stereoisomer thereof, is selected from the group consisting of:

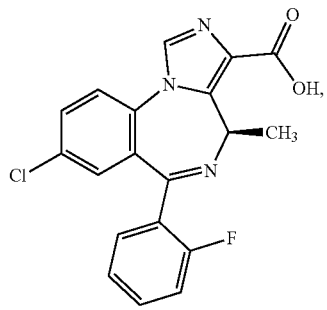

-continued

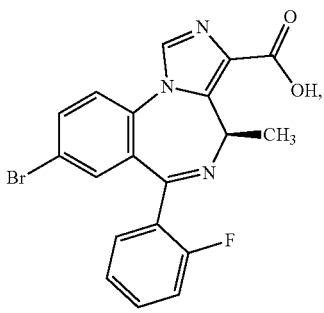

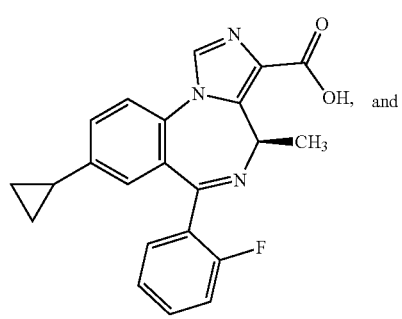

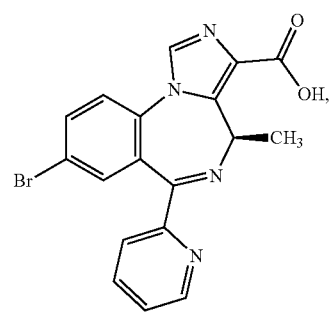

or a pharmaceutically acceptable salt thereof.

9. The method of claim 8, wherein the compound, or stereoisomer thereof, is:

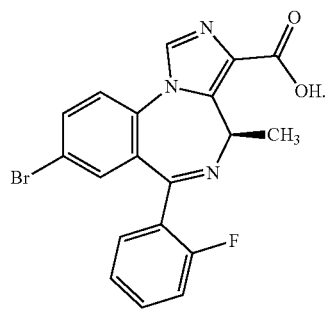 [SMILES: C[C@H]1N=C(c2ccccc2F)c2cc(Br)ccc2-n2cnc(C(=O)O)c21]

or a pharmaceutically acceptable salt thereof.

10. A method for treating lung disease in a subject, wherein the method comprises administering to the subject in need thereof a therapeutically effective amount of a compound of formula (I):

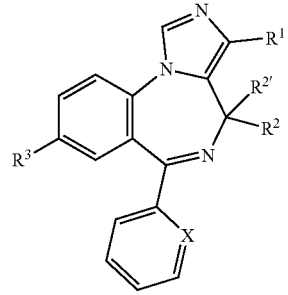

or a pharmaceutically acceptable salt or stereoisomer thereof, wherein:
$R^1$ is C(O)OH;
$R^2$ is $C_{1-4}$ alkyl, $CF_3$, or $CCl_3$;
$R^{2'}$ is H, $C_{1-4}$ alkyl, $CF_3$, or $CCl_3$;
$R^3$ is Cl, Br, or cyclopropyl; and
X is CF, CCl, CBr, CI, or N.

11. The method of claim 10, wherein the compound, or stereoisomer thereof, is selected from the group consisting of:

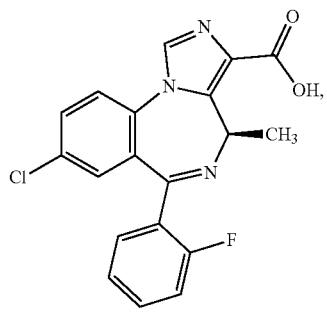

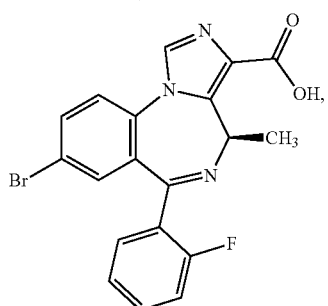

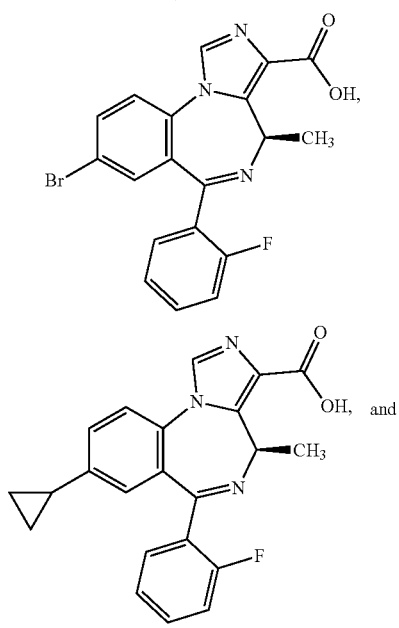

-continued
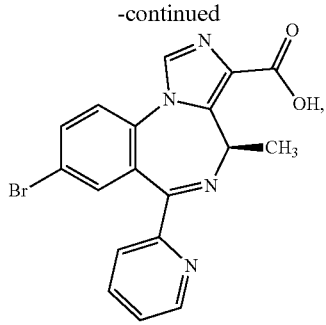
or a pharmaceutically acceptable salt thereof.
12. The method of claim 11, wherein the compound, or stereoisomer thereof, is:
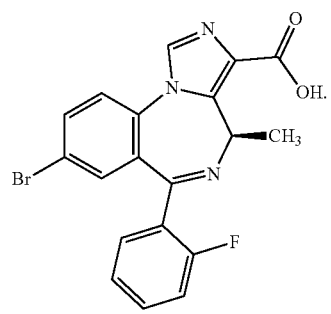 [SMILES: C[C@H]1N=C(c2ccccc2F)c2cc(Br)ccc2-n2cnc(C(=O)O)c21]
or a pharmaceutically acceptable salt thereof.
* * * * *